United States Patent [19]

Eberlein et al.

[11] Patent Number: 6,040,289
[45] Date of Patent: Mar. 21, 2000

[54] AMINO ACID DERIVATIVES, MEDICAMENTS CONTAINING SAID COMPOUNDS AND METHODS OF PRODUCING SAID COMPOUNDS

[75] Inventors: Wolfgang Eberlein; Wolfhard Engel; Klaus Rudolf, all of Biberach; Henri Doods, Warthausen; Heike-Andrea Wieland, Biberach; Klaus-Dieter Willim, Hochdorf, all of Germany

[73] Assignee: Dr. Karl Thomae GmbH, Biberach, Germany

[21] Appl. No.: 09/077,663

[22] PCT Filed: Nov. 26, 1996

[86] PCT No.: PCT/EP96/05214

§ 371 Date: May 29, 1998

§ 102(e) Date: May 29, 1998

[87] PCT Pub. No.: WO97/19914

PCT Pub. Date: Jun. 5, 1997

[30] Foreign Application Priority Data

Nov. 30, 1995 [DE] Germany .......................... 195 44 686

[51] Int. Cl.⁷ .......................... A61K 38/00; A01N 37/18
[52] U.S. Cl. .................................. 514/2; 564/123
[58] Field of Search .................. 564/123; 514/2

[56] References Cited

U.S. PATENT DOCUMENTS 5,616,620 4/1997 Rudolf et al. .
5,807,875 9/1998 Klaus et al. .

FOREIGN PATENT DOCUMENTS 0 230 037 7/1987 European Pat. Off. .
WO 94/17035 8/1994 WIPO .

OTHER PUBLICATIONS

Interactions of derivatives of guanidinophenylglycine and guanidinophenylalanine with trypsin and related enzymes. Tsunematsu, H. et al. J. Biochem. 88, 1773–1783 (1980).

Interactions of derivatives of guanidinophenylalanine and guanidinophenylglycine with streptomyces griseus trypsin. Hatanaka, Y. et al, Biochimica et Biophysica Acta 822 (1985) 274–279.

Beta–Napthylamides of Guanidinophenyl amino acids as substrates of aminopeptidases. Tsunematsu, H. et al. Chem. Pharm. Bull. 36(3) 1205–1209 (1988).

*Primary Examiner*—Gary L. Kunz
*Attorney, Agent, or Firm*—Robert P. Raymond; Anthony P. Bottino; Alan R. Stempel

[57] ABSTRACT

The invention relates to new amino acid derivatives of general formula

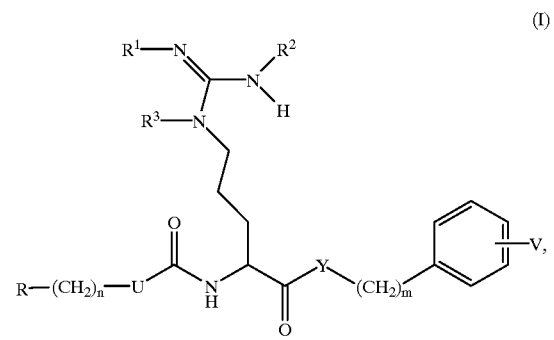

wherein R, U, V, Y, n, m and $R^1$ to $R^3$ are defined as in claim 1, their tautomers, diastereomers, enantiomers, mixtures thereof and salts thereof, particularly the physiologically acceptable salts thereof with inorganic or organic acids or bases, which have valuable pharmacological properties, particularly selective NPY-antagonistic properties, pharmaceutical compositions containing these compounds, the use thereof and processes for preparing them.

7 Claims, No Drawings

AMINO ACID DERIVATIVES, MEDICAMENTS CONTAINING SAID COMPOUNDS AND METHODS OF PRODUCING SAID COMPOUNDS

The invention relates to new amino acid derivatives of general formula

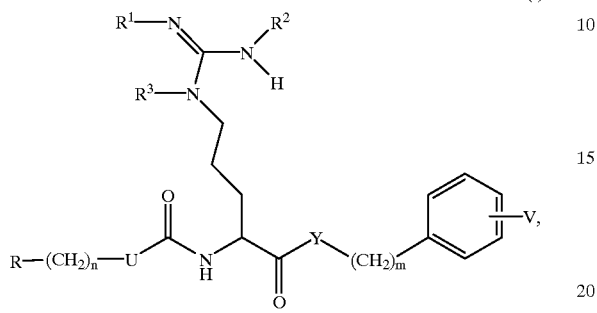

which have NPY-antagonistic properties, their tautomers, diastereomers, enantiomers, mixtures thereof and salts thereof, particularly the physiologically acceptable salts thereof with inorganic or organic acids or bases, pharmaceutical compositions containing these compounds, the use thereof and processes for preparing them.

Amino acid derivatives with NPY-antagonistic properties have already been described in WO 94/17035.

In general formula I above

R denotes a phenyl, 1-naphthyl or 2-naphthyl group, a 5-membered heteroaromatic ring linked via a carbon atom and containing a nitrogen, oxygen or sulphur atom or a nitrogen atom and an oxygen, sulphur or further nitrogen atom, whilst a nitrogen atom of an imino group may be substituted by an alkyl, alkoxycarbonylalkyl, carboxyalkyl, dialkylaminoalkyl, aminocarbonyl, alkylaminocarbonyl, dialkylaminocarbonyl or alkoxycarbonyl group, or a 6-membered heteroaromatic ring linked via a carbon atom, containing 1, 2 or 3 nitrogen atoms, whilst a 1,4-butadienylene group may be attached both to the 5-membered and to the 6-membered heteroaromatic rings via two adjacent carbon atoms and the bicyclic heteroaromatic rings thus formed may also be bound via a carbon atom of the 1,4-butadienylene group and the groups mentioned for R hereinbefore, including the mono- and bicyclic heteroaromatic rings in their carbon skeleton, may additionally be mono-, di- or at most trisubstituted by fluorine, chlorine or bromine atoms, by alkyl groups, cycloalkyl groups with 3 to 8 carbon atoms, alkoxy, phenyl, phenylalkoxy, trifluoromethyl, alkoxycarbonylalkyl, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, alkanoyl, cyano, trifluoromethoxy, trifluoromethylthio, trifluoromethylsulphynyl or trifluoromethylsulphonyl groups, whilst the substituents may be identical or different and the abovementioned benzoyl, benzoylamino and benzoylmethylamino groups in turn may additionally be substituted in the phenyl moiety by a fluorine, chlorine or bromine atom, an alkyl, trifluoromethyl, amino or acetylamino group, or the diphenylmethyl group, wherein the phenyl groups independently of one another may be mono- or disubstituted by fluorine, chlorine or bromine atoms, methyl, methoxy, hydroxycarbonylmethoxy, alkoxycarbonylmethoxy, hydroxy or trifluoromethyl groups, whilst the substituents in each case may be identical or different, n denotes the numbers 0, 1 or 2, U denotes a single bond, an oxygen atom or the —NH— group, $R^1$ denotes a branched or unbranched aliphatic alkylcarbonyl group containing 2 to 5 carbon atoms, which may be substituted in the alkyl moiety by an alkoxycarbonyl or phenylalkoxycarbonyl group, by a phenyl group or by a 5- or 6-membered heteroaromatic ring linked via a carbon atom, or a benzoyl group, wherein the phenyl moiety may also be replaced by a 5- or 6-membered heteroaromatic ring linked via a carbon atom, whilst the 5-membered heteroaromatic rings mentioned hereinbefore may contain a nitrogen, an oxygen or a sulphur atom or a nitrogen atom and an additional oxygen, sulphur or further nitrogen atom and may also be substituted by an alkyl group at a nitrogen atom, the 6-membered heteroaromatic rings may contain 1, 2 or 3 nitrogen atoms, and the phenyl groups mentioned hereinbefore may additionally be mono-, di- or at most tri-substituted, as may the heteroaromatic rings in their carbon skeleton, by fluorine, chlorine or bromine atoms, by alkyl groups, cycloalkyl groups with 3 to 8 carbon atoms, alkoxy, trifluoromethyl, alkoxycarbonylalkyl, carboxyalkyl, hydroxy, amino, acetylamino, propionylamino, aminocarbonyl, alkylaminocarbonyl, dialkylaminocarbonyl, alkanoyl, cyano, trifluoromethoxy, trifluoromethylthio, trifluoromethylsulphynyl or trifluoromethylsulphonyl groups, whilst the substituents may be identical or different, the aminocarbonyl group, which may be mono- or disubstituted at the nitrogen atom by alkyl, phenylalkyl, (1-naphthyl)alkyl, (2-naphthyl)alkyl, alkoxycarbonylalkyl, phenylalkoxycarbonylalkyl, phenoxycarbonylalkyl, carboxyalkyl, diphenylalkyl, phenyl, cycloalkyl or cycloalkylalkyl groups with 3 to 8 carbon atoms in the ring in each case, whilst the substituents may be identical or different and the abovementioned phenyl groups may in turn, independently of one another, be mono- or disubstituted by fluorine, chlorine or bromine atoms, methyl, methoxy, hydroxycarbonylmethoxy, alkoxycarbonylmethoxy, hydroxy or trifluoromethyl groups, an alkoxycarbonyl or phenylalkoxycarbonyl group, whilst the phenyl moiety in its turn may be mono- or disubstituted by fluorine, chlorine or bromine atoms, methyl, methoxy, hydroxycarbonylmethoxy, alkoxycarbonylmethoxy, hydroxy or trifluoromethyl groups and the substituents in each case may be identical or different, a phenyl group, a five-membered heteroaromatic ring bound via a carbon atom, which contains a nitrogen, oxygen or sulphur atom or a nitrogen atom and an oxygen, sulphur or further nitrogen atom, whilst a nitrogen atom of an imino group may be substituted by an alkyl group, or a 6-membered heteroaromatic ring linked via a carbon atom, which contains 1, 2 or 3 nitrogen atoms, whilst the phenyl group may additionally be mono-, di- or at most trisubstituted, as may the 5- and 6-membered heteroaromatic rings in their carbon skeleton, by fluorine, chlorine or bromine atoms, by alkyl groups, cycloalkyl groups with 3 to 8 carbon atoms, phenylalkyl, alkoxy, trifluoromethyl, alkoxycarbonylalkyl, carboxyalkyl, hydroxy, amino, acetylamino, propionylamino, aminocarbonyl, alkylaminocarbonyl, dialkylaminocarbonyl, alkanoyl, cyano, trifluoromethoxy, trifluoromethylthio, trifluoromethylsulphinyl or trifluoromethylsulphonyl groups and the substituents may be identical or different, or, if $R^2$ denotes a hydrogen atom, $R^1$ may also denote the methyl group, $R^2$ denotes a hydrogen atom, an alkyl or phenylalkyl group, which may also be mono- or disubstituted in the phenyl moiety by fluorine, chlorine or bromine atoms, alkyl, trifluoromethyl, amino or acetylamino groups, whilst the substituents may be identical or different, $R^3$ denotes a hydrogen atom or an alkyl group, Y denotes an oxygen atom or the —$NR^4$— group wherein
  $R^4$ denotes a hydrogen atom, a branched or unbranched alkyl group with 1 to 6 carbon atoms or the phenylmethyl group, m denotes the numbers 1 or 2 and V denotes a hydrogen atom, a fluorine, chlorine, bromine or iodine atom, a cyano, alkyl, hydroxy, alkoxy, phenylalkoxy alkylcarbonyl, dialkylamino, hydroxymethyl, hydroxyethyl, hydroxypropyl, hydroxybutyl, trifluoromethyl, trifluoromethoxy or trifluoromethylthio group or the group —$(CH_2)_o$—$Y^1$—W—$Y^2$, wherein
  o denotes the numbers 0, 1 or 2,
  W denotes the —$SO_2$— group or the group >C=X wherein
    X denotes an oxygen atom or one of the divalent groups =N—$CONH_2$ or =N—CN,
  Y1 denotes a single bond, an oxygen atom or the group —$NR^5$— wherein
    $R^5$ denotes a hydrogen atom or a straight-chained or branched alkyl group with 1 to 6 carbon atoms or
    $R^5$ together with the group $Y^2$, the enclosed nitrogen atom and the enclosed group >C=X forms a saturated heterocyclic ring with 5 to 7 ring members,
  $Y^2$ denotes a straight-chained or branched alkyl group with 1 to 10 carbon atoms optionally substituted by a hydroxy, alkoxycarbonyl or aminocarbonyl group, a cycloalkyl group with 4 to 10 carbon atoms, a straight-chained or branched alkoxy group with 1 to 5 carbon atoms, an aminoalkyl, alkylaminoalkyl, dialkylaminoalkyl, phenylmethoxy or 2-phenylethoxy group, a phenyl or phenylalkyl group with 1 to 3 carbon atoms in the alkyl moiety optionally mono-, di- or trisubstituted in the phenyl moiety by fluorine, chlorine or bromine atoms, by methyl, trifluoromethyl, cyano, amino, hydroxy, methoxy, acetyl, acetylamino, aminocarbonyl, methylaminocarbonyl or dimethylaminocarbonyl groups, whilst the substituents may be identical or different, or
  the —$NR^6R^7$ group wherein
    $R^6$ denotes a hydrogen atom, a straight-chained or branched alkyl group with 1 to 6 carbon atoms optionally substituted by a hydroxy, carboxy, alkoxycarbonyl or dialkylamino group with the proviso that the hydroxy group is not bound in the 1-position of the alkyl group, a cycloalkyl group with 4 to 8 carbon atoms or a phenyl, phenylmethyl, 2-phenylethyl or 3-phenylpropyl group optionally mono-, di- or trisubstituted in the phenyl moiety by fluorine, chlorine or bromine atoms, by methyl, trifluoromethyl, hydroxy, methoxy, amino, acetylamino, aminocarbonyl, methylaminocarbonyl, dimethylaminocarbonyl or cyano groups, whilst the substituents may be identical or different, or an alkanoyl, benzoyl, phenylalkanoyl, alkoxycarbonyl or aminocarbonyl group and
    $R^7$ has the meanings given for $R^6$ with the exception of a phenyl, alkanoyl, benzoyl, phenylalkanoyl, alkoxycarbonyl or aminocarbonyl group or
    $R^6$ and $R^7$ together denote an n-alkylene group with 4 to 6 carbon atoms or
    $R^7$ together with the group $R^5$ of the group —$NR^5$— mentioned for $Y^1$ hereinbefore denotes an unbranched alkylene group or oxoalkylene group with 2 to 4 carbon atoms, whilst all the abovementioned alkyl, cycloalkylalkyl, alkoxy, phenoxycarbonylalkyl, phenylalkoxy, phenylalkoxycarbonyl, phenylalkoxycarbonylalkyl, phenylalkanoyl, phenylalkyl, diphenylalkyl, naphthylalkyl, alkoxycarbonylalkyl, alkoxycarbonylmethoxy, carboxyalkyl, aminoalkyl, monoalkylamino, dialkylamino, alkylaminoalkyl, dialkylaminomethyl, dialkylaminoalkyl, alkylaminocarbonyl, dialkylaminocarbonyl, alkanoyl and alkoxycarbonyl groups, unless otherwise stated, may each contain 1 to 5 carbon atoms in the alkyl and alkoxy moieties.

In the definitions given for the groups mentioned hereinbefore:

for example R may denote the phenyl, diphenylmethyl, 2-pyridinyl, 3-pyridinyl, 4-pyridinyl, 2-thienyl, 3-thienyl, 2-furyl, 3-furyl, 1H-pyrrol-2-yl, 1H-pyrrol-3-yl, 1-methyl-1H-pyrrol-2-yl, 1-methyl-1H-pyrrol-3-yl, 1-naphthyl, 2-naphthyl, 1H-indol-2-yl, 1H-indol-3-yl, 1H-indol-4-yl, 1H-indol-5-yl, 1H-indol-6-yl, 1H-indol-7-yl, benzo[b]furan-2-yl, benzo[b]furan-3-yl, benzo[b]thiophen-2-yl, benzo[b]thiophen-3-yl, 2-quinolinyl, 3-quinolinyl, 4-quinolinyl, benzo[c]thiophen-1-yl, 1-isoquinolinyl, 3-isoquinolinyl, 4-isoquinolinyl, pyrazinyl, 2-pyrimidinyl, 4-pyrimidinyl, 5-pyrimidinyl, 3-pyridazinyl, 4-pyridazinyl, 2-imidazolyl, 4-imidazolyl, 1-H-benzimidazolyl-5-yl, 3-pyrazolyl, 4-pyrazolyl, 1,3-oxazol-2-yl, 1,3-oxazol-4-yl, 1,3-oxazol-5-yl, 3-isoxazolyl, 4-isoxazolyl, 5-isoxazolyl, 2-quinazolinyl, 4-quinazolinyl or 2-quinoxalinyl group, whilst these may additionally be substituted by the groups mentioned hereinbefore, V may denote an acetylaminomethyl, ethoxycarbonylaminomethyl, aminosulphonylaminomethyl, aminocarbonylaminomethyl, aminocarbonylmethyl, methylaminosulphonylmethyl, methoxycarbonylaminomethyl, methylaminocarbonylaminomethyl, benzoylaminomethyl, phenylaminocarbonylaminomethyl, aminosulphonylmethyl, ethylaminocarbonylaminomethyl, 1-methylethylaminocarbonylaminomethyl, [[amino (aminocarbonylimino)methyl]amino]methyl, ethoxycarbonylaminocarbonylaminomethyl, dimethylaminocarbonylaminomethyl, aminocarbonyloxymethyl, tert.butoxycarbonylaminomethyl, aminocarbonylaminocarbonylaminomethyl, [(amino (cyanimino)methyl]amino]methyl, methoxycarbonylmethyl, methylaminocarbonylmethyl, [[(dimethylamino)carbonyl]methylamino]methyl, [(aminocarbonyl)methylamino]-methyl, [[(methylamino)carbonyl]methylamino]methyl, [(methoxycarbonyl)methylamino]methyl, [[(carboxymethyl)amino]carbonyl]methyl, [[[bis(carboxymethyl)]amino]carbonyl]methyl, [[[bis(methoxycarbonylmethyl)]amino]carbonyl]methyl, [(ethoxycarbonylaminocarbonyl)methylamino]methyl, ethoxycarbonylmethylaminocarbonylaminomethyl, carboxymethylaminocarbonylaminomethyl, dimethylaminocarbonylmethyl, 2-(aminocarbonyl)-ethyl, (2-oxo-1-imidazolidinyl)methyl, 2-(methoxycarbonyl)-ethyl, [(4-amino-1,4-dioxobutyl)amino]methyl or 2-(aminocarbonylamino)ethyl group and $R^1$ may denote a methoxycarbonyl, ethoxycarbonyl, propyloxycarbonyl, butyloxycarbonyl, methoxycarbonylethylcarbonyl, aminocarbonyl, methylaminocarbonyl, ethylaminocarbonyl, dimethylaminocarbonyl, propylaminocarbonyl, butylaminocarbobyl, phenylaminocarbonyl, benzylaminocarbonyl, (2-phenylethyl)aminocarbonyl, (3-phenylpropyl)aminocarbonyl, (3,3-diphenylpropyl)aminocarbonyl, 1-naphthylmethylaminocarbonyl, 2-naphthylmethylaminocarbonyl, cyclohexylaminocarbonyl, 4-(4-methoxyphenyl)-butylaminocarbonyl, hydroxycarbonylethylaminocarbonyl, ethoxycarbonylethylaminocarbonyl, benzoyl, 4-fluorobenzoyl, nicotinoyl, isonicotinoyl, 2-thienyl, 3-thienyl, 2-furyl, 3-furyl, 1H-pyrrol-2-yl, 1H-pyrrol-3-yl, 1-methyl-1H-pyrrol-2-yl, 1-methyl-1H-pyrrol-3-yl, pyrazinyl, 2-pyrimidinyl, 4-pyrimidinyl, 5-pyrimidinyl, 3-pyridazinyl, 4-pyridazinyl, 2-imidazolyl, 4-imidazolyl, 3-pyrazolyl, 4-pyrazolyl, 1,3-oxazol-2-yl, 1,3-oxazol-4-yl, 1,3-oxazol-5-yl, 3-isoxazolyl, 4-isoxazolyl, 5-isoxazolyl, 2-thiazolyl, 4-methyl-2-thiazolyl, 5-methyl-2-thiazolyl, 4-(2-phenylethyl)-2-thiazolyl, 4-(3-phenylpropyl)-2-thiazolyl, 2-pyridinyl, 3-pyridinyl, 4-pyridinyl or 5-methyl-2-pyridinyl group.

The present invention relates to the racemates, if in compounds of general formula I the asymmetric carbon atom of the central amino acid is the only chiral element. However, the application also includes the individual diastereomers or the mixtures thereof which occur when a compound of general formula I contains two or more chiral elements. Particularly preferred are the compounds of general formula I which are in the (D) or (R) configuration with respect to the partial amino acid structure

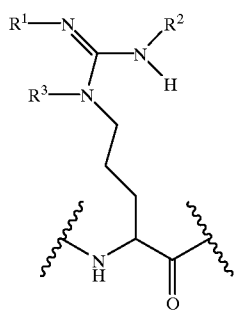

The compounds of general formula I have valuable pharmacological properties, based on their selective NPY-antagonistic properties. The invention further relates to pharmaceutical compositions containing these compounds, their use and the preparation thereof.

Preferred compounds of general formula I above are those wherein

R, n, U, $R^1$, $R^2$, $R^3$ and m are as hereinbefore defined,

Y denotes an oxygen atom or the —$NR^4$ group wherein $R^4$ denotes a hydrogen atom, the methyl or ethyl group, and V is bound in the 3- or 4-position of the benzene ring and denotes a hydrogen, fluorine, chlorine, bromine or iodine atom, a cyano, alkyl, hydroxy, alkoxy, phenylalkoxy, alkylcarbonyl, dialkylamino, hydroxymethyl, hydroxyethyl, hydroxypropyl, hydroxybutyl, trifluoromethyl, trifluoromethoxy, trifluoromethylthio group or the group —$(CH_2)_o$—$Y^1$—W—$Y^2$ wherein o, $Y^1$ and $Y^2$ are as hereinbefore defined and W denotes the carbonyl group, their tautomers, diastereomers, enantiomers and the salts thereof.

Particularly preferred compounds of general formula I above are those wherein

R denotes a phenyl, 1-naphthyl or 2-naphthyl group, a 5-membered heteroaromatic ring linked via a carbon atom, which contains a nitrogen, oxygen or sulphur atom or two nitrogen atoms, whilst a nitrogen atom of an imino group may be substituted by an alkyl group, or a 6-membered heteroaromatic ring linked via a carbon atom, which contains 1, 2 or 3 nitrogen atoms, whilst a 1,4-butadienylene group may be attached both to the 5-membered and to the 6-membered heteroaromatic rings via two adjacent carbon atoms and the bicyclic heteroaromatic rings thus formed may also be bound via a carbon atom of the 1,4-butadienylene group and the groups mentioned for R hereinbefore, including the mono- and bicyclic heteroaromatic rings in their carbon skeleton, may additionally be substituted by a fluorine, chlorine or bromine atom, by an alkyl group, a cycloalkyl group with 4 to 7 carbon atoms, an alkoxy, phenyl or trifluoromethyl group, or the diphenylmethyl group wherein the phenyl groups may be mono- or disubstituted independently of one another by fluorine, chlorine or bromine atoms, methyl, methoxy, hydroxycarbonylmethoxy, alkoxycarbonylmethoxy, hydroxy or trifluoromethyl groups, whilst the substituents in each case may be identical or different, n denotes the numbers 0, 1 or 2, U denotes a single bond, $R^1$ denotes a branched or unbranched aliphatic alkylcarbonyl group containing 2 to 5 carbon atoms, which may be substituted in the alkyl moiety by an alkoxycarbonyl or phenylalkoxycarbonyl group or by a phenyl group, or a benzoyl or pyridinylcarbonyl group, whilst the phenyl and pyridinyl moieties in the abovementioned groups may be substituted by a fluorine, chlorine or bromine atom, by an alkyl group, a cycloalkyl group with 4 to 7 carbon atoms, or by an alkoxy or trifluoromethyl group, the aminocarbonyl group, which may be mono- or disubstituted at the nitrogen atom by alkyl, phenylalkyl, (1-naphthyl)alkyl, (2-naphthyl)alkyl, alkoxycarbonylalkyl, carboxyalkyl, ω,ω- diphenylalkyl, phenyl, cycloalkyl or cycloalkylalkyl groups each with 3 to 8 carbon atoms in the ring, whilst the substituents may be identical or different and the phenyl groups in the abovementioned groups may in turn be substituted by a fluorine, chlorine or bromine atom, or by a methyl, methoxy, hydroxy or trifluoromethyl group, an alkoxycarbonyl or phenylalkoxycarbonyl group, which may be substituted in the phenyl moiety by a fluorine, chlorine or bromine atom, by a methyl, methoxy, hydroxy or trifluoromethyl group, a phenyl group or a five-membered heteroaromatic ring bound via a carbon atom, which contains a nitrogen, oxygen or sulphur atom or a nitrogen atom and an oxygen, sulphur or further nitrogen atom, whilst a nitrogen atom of an imino group may be substituted by an alkyl group, or a 6-membered heteroaromatic ring linked via a carbon atom, which contains 1, 2 or 3 nitrogen atoms, whilst the phenyl group may additionally be substituted, as may the 5- and 6-membered heteroaromatic rings in their carbon skeleton, by a fluorine, chlorine or bromine atom, by an alkyl group, by a cycloalkyl group with 3 to 6 carbon atoms, by a phenylalkyl, alkoxy, trifluoromethyl, hydroxy or amino group, or, if $R^2$ denotes a hydrogen atom, $R^1$ may also denote the methyl group, $R^2$ denotes a hydrogen atom, an alkyl or phenylalkyl group, the phenyl group of which may also be substituted by a fluorine, chlorine or bromine atom, an alkyl, trifluoromethyl, amino or acetylamino group, $R^3$ denotes a hydrogen atom or the methyl group, Y denotes the —$NR^4$— group wherein $R^4$ denotes a hydrogen atom, the methyl or ethyl group, m denotes the number 1 or 2 and V, which is bound in the 4 position of the benzene ring, denotes a hydrogen atom, a fluorine, chlorine or bromine atom, a cyano, alkyl, hydroxy, alkoxy, phenylalkoxy, hydroxymethyl, hydroxyethyl or trifluoromethyl group or the group —$(CH_2)_o$—$Y^1$—W—$Y^2$ wherein o denotes the number 0, 1 or 2, W denotes the carbonyl group, Y1 denotes a single bond, an oxygen atom or the group —$NR^5$, wherein $R^5$ denotes a hydrogen atom or a straight-chained or branched alkyl group with 1 to 4 carbon atoms or $Y^2$ denotes a straight-chained or branched alkyl group with 1 to 5 carbon atoms optionally substituted by a hydroxy, alkoxycarbonyl or aminocarbonyl group, an alkoxy group with 1 to 3 carbon atoms, an aminoalkyl, alkylaminoalkyl or dialkylaminoalkyl group or a phenyl or phenylalkyl group with 1 to 3 carbon atoms in the alkyl moiety optionally substituted in the phenyl moiety by a fluorine, chlorine or bromine atom, by a methyl, trifluoromethyl, cyano, amino, hydroxy or methoxy group or the —$NR^6R^7$ group wherein $R^6$ denotes a hydrogen atom, a straight-chained or branched alkyl group with 1 to 6 carbon atoms, a cycloalkyl group with 4 to 6 carbon atoms or a phenyl group optionally substituted by a fluorine, chlorine or bromine atom, by a methyl, trifluoromethyl, hydroxy or methoxy group, and $R^7$ has the meanings given for $R^6$ with the exception of a phenyl group, whilst all the abovementioned alkyl, alkoxy, phenylalkoxy, alkoxycarbonylalkyl, carboxyalkyl, dialkylaminoalkyl, alkylaminocarbonyl, dialkylaminocarbonyl, alkanoyl and alkoxycarbonyl groups, unless otherwise stated, may each contain 1 to 5 carbon atoms in the alkyl and alkoxy moieties, their tautomers, diastereomers, enantiomers and the salts thereof.

Most particularly preferred compounds of general formula I above are those wherein R denotes a 1-naphthyl, 2-naphthyl, 1H-pyrrol-2-yl, 1H-pyrrol-3-yl, 1H-indol-2-yl or 1H-indol-3-yl group optionally substituted in the carbon skeleton by an alkyl group or an alkoxy group with 1 to 3 carbon atoms or the diphenylmethyl group wherein the phenyl groups independently of one another may be substituted by a fluorine, chlorine or bromine atom, a hydroxy, methoxy or a methyl group, n denotes the numbers 0 or 1, U denotes a single bond, $R^1$ denotes a branched or unbranched aliphatic alkylcarbonyl group containing 2 to 5 carbon atoms, which may be substituted by an alkoxycarbonyl group with 1 to 4 carbon atoms in the alkoxy moiety, the aminocarbonyl group, which may be substituted at the nitrogen atom by one or two alkyl groups each with 1 to 5 carbon atoms, by a phenylalkyl group with 1 to 5 carbon atoms in the alkyl moiety, by an alkoxyphenylalkyl group with 1 to 3 carbon atoms in the alkoxy and 1 to 5 carbon atoms in the alkyl moiety, a (1-naphthyl)alkyl or (2-naphthyl)alkyl group with 1 to 3 carbon atoms in the alkyl moiety, an alkoxycarbonylalkyl group with 1 to 3 carbon atoms in the alkoxy and alkyl moieties, a carboxyalkyl group with 1 to 3 carbon atoms in the alkyl moiety, an o,o-diphenylalkyl group with 1 to 5 carbon atoms in the alkyl moiety, a phenyl or cycloalkyl group with 4 to 7 carbon atoms in the ring, an alkoxycarbonyl group with 1 to 5 carbon atoms in the alkoxy moiety or a phenylalkoxycarbonyl group with 1 to 3 carbon atoms in the alkoxy moiety, the phenyl, pyridinyl or thiazolyl group, which may be i substituted in each case by an alkyl group with 1 to 3 carbon atoms or a phenylalkyl group with 1 to 5 carbon atoms in the alkyl moiety, or, if $R^2$ denotes a hydrogen atom, $R^1$ may also denote the methyl group, $R^2$ denotes a hydrogen atom or an alkyl group with 1 to 3 carbon atoms optionally terminally substituted by a phenyl group, $R^3$ denotes a hydrogen atom or the methyl group, Y denotes an oxygen atom or the —$NR^4$ group wherein $R^4$ denotes a hydrogen atom, the methyl or ethyl group, m denotes the number 1 and V is bound in the 4 position of the benzene ring and denotes a hydrogen atom, an alkyl group with 1 to 3 carbon atoms, a hydrogen group, an alkoxy group with 1 to 3 carbon atoms or the group —$(CH_2)_o$—$Y^1$—W—$Y^2$ wherein o denotes the numbers 0 or 1, W denotes the carbonyl group, Y1 denotes a single bond, an oxygen atom or the group —$NR^5$, wherein $R^5$ denotes a hydrogen atom or the methyl group, $Y^2$ denotes the —$NR^6R^7$ group wherein R⁶ denotes a hydrogen atom or an alkyl group with 1 to 3 carbon atoms and R⁷ denotes a hydrogen atom, their tautomers, diastereomers, enantiomers and the salts thereof.

The following are mentioned as examples of particularly preferred compounds:

(1) (R)-N²-(diphenylacetyl)-N⁷-(methylaminocarbonyl)-N-[[-(methylaminocarbonyloxy)phenyl]methyl]-argininamide, (2) (R)-N-[[4-(aminocarbonylaminomethyl)phenyl]methyl]-N⁷-(butylaminocarbonyl)-N²-(diphenylacetyl)-argininamide, (3) (R)-N²-(diphenylacetyl)-N-[(4-hydroxyphenyl)methyl]-N⁷-(methylaminocarbonyl)-argininamide, (4) (R)-N⁷-(butylaminocarbonyl)-N²-(diphenylacetyl)-N-[(4-hydroxyphenyl)methyl]-argininamide, (5) (R)-N-[[4-(aminocarbonylaminomethyl)phenyl]methyl]-N²-(diphenylacetyl)-N⁷-(methylaminocarbonyl)-argininamide, (6) (R)-N-[[4-(aminocarbonylaminomethyl)phenyl]methyl]-N²-(diphenylacetyl)-N⁷-(ethylaminocarbonyl)-argininamide, (7) (R)-N²-(diphenylacetyl)-N⁷-(ethylaminocarbonyl)-N-[(4-hydroxyphenyl)methyl]-argininamide, (8) (R)-N-[[4-(aminocarbonylmethyl)phenyl]methyl]-N²-(diphenylacetyl)-N⁷-[(methylethyl)aminocarbonyl]-argininamide, (9) (R)-N²-(diphenylacetyl)-N-[(4-hydroxyphenyl)methyl]-N⁷-[(phenylmethyl)aminocarbonyl]-argininamide,

(10) (R)-N²-(diphenylacetyl)-N-[(4-hydroxyphenyl)methyl]-N⁷-(methoxycarbonyl)-argininamide,

(11) (R,S)-N²-(diphenylacetyl)-N-[(4-methoxyphenyl)methyl]-N⁷-(methylaminocarbonyl)-argininamide,

(12) (R)-N-[[4-(aminocarbonylmethyl)phenyl]methyl]-N²-(diphenylacetyl)-N⁷-(methylaminocarbonyl)-argininamide,

(13) (R)-N-[[4-(aminocarbonylaminomethyl)phenyl]methyl]-N²-(diphenylacetyl)-N⁷-[(phenylmethyl)aminocarbonyl]-argininamide,

(14) (R)-N⁷-(aminocarbonyl)-N²-(diphenylacetyl)-N-[(4-hydroxyphenyl)methyl]-N⁷'-(phenylmethyl)-argininamide,

(15) (R)-N⁷-(aminocarbonyl)-N²-(diphenylacetyl)-N-[(4-hydroxyphenyl)methyl]-argininamide,

(16) (R)-N⁷-(aminocarbonyl)-N²-(diphenylacetyl)-N-[(4-hydroxyphenyl)methyl]-N⁷'-methyl-argininamide,

(17) (R)-N⁷-(butoxycarbonyl)-N²-(diphenylacetyl)-N-[(4-hydroxyphenyl)methyl]-argininamide,

(18) (R)-N²-(diphenylacetyl)-N-[(4-hydroxyphenyl)methyl]-N⁷-(phenylmethoxycarbonyl)-argininamide,

(19) (P)-N-[[4-(aminocarbonylaminomethyl)phenyl]methyl]-N²-(diphenylacetyl)-N⁷-[[2-(ethoxycarbonyl)ethyl]aminocarbonyl]-argininamide,

(20) (R)-N-[[4-(aminocarbonylaminomethyl)phenyl]methyl]-N⁷-[[2-(carboxy)ethyl]aminocarbonyl]-N²-(diphenylacetyl)-argininamide,

(21) (R)-N²-(diphenylacetyl)-N-(phenylmethyl)-N⁷-(methoxycarbonyl)-argininamide,

(22) (R)-N²-(diphenylacetyl)-N⁷-(methylaminocarbonyl)-N-(phenylmethyl)-argininamide,

(23) (R)-N²-(diphenylacetyl)-N-(phenylmethyl)-N⁷-[(phenylmethyl)aminocarbonyl]-argininamide,

(24) (R)-N-[[4-(aminocarbonylaminomethyl)phenyl]methyl]-N²-[(1H-indol-3-yl)acetyl]-N⁷-(methylaminocarbonyl)-argininamide,

(25) (R)-N⁷-(dimethylaminocarbonyl)-N²-(diphenylacetyl)-N-[(4-hydroxyphenyl)methyl]-argininamide,

(26) (R)-N²-[(1H-indol-3-yl)acetyl]-N-[(4-methoxyphenyl)methyl]-N⁷-(methylaminocarbonyl)-argininamide,

(27) (R)-N²-[(1H-indol-3-yl)acetyl]-N-[(4-methoxyphenyl)methyl]-N⁷-[(3-phenylpropyl)aminocarbonyl]-argininamide,

(28) (R)-N²-(diphenylacetyl)-N-[(4-hydroxyphenyl)methyl]-N-methyl-N⁷-(methylaminocarbonyl)-argininamide,

(29) (R)-N²-(diphenylacetyl)-N-[(4-hydroxyphenyl)methyl]-N-methyl-N⁷-[(phenylmethyl)aminocarbonyl]-argininamide,

(30) (R)-N²-(diphenylacetyl)-N⁷-(methoxycarbonyl)-N-[(4-methoxyphenyl)methyl]-argininamide,

(31) (R)-N²-(diphenylacetyl)-N-[(4-methoxyphenyl)methyl]-N⁷-[(phenylmethyl)aminocarbonyl]-argininamide,

(32) (R)-N-[(4-hydroxyphenyl)methyl]-N²-[(6-methoxy-2-naphthyl)acetyl]-N⁷-(methylaminocarbonyl)-argininamide,

(33) (R)-N²-(diphenylacetyl)-N-[(4-hydroxyphenyl)methyl]-N⁷-[[4-(4-methoxyphenyl)butyl]aminocarbonyl]-argininamide,

(34) (R)-N²-(diphenylacetyl)-N⁷-[(3,3-diphenylpropyl)aminocarbonyl]-N-[(4-hydroxyphenyl)methyl]-argininamide,

(35) (R)-N⁷-(cyclohexylaminocarbonyl)-N²-(diphenylacetyl)-N-[(4-hydroxyphenyl)methyl]-argininamide,

(36) (R)-N²-(diphenylacetyl)-N-[(4-hydroxyphenyl)methyl]-N⁷-(phenylaminocarbonyl)-argininamide,

(37) (R)-N²-(diphenylacetyl)-N-[(4-hydroxyphenyl)methyl]-N⁷-[(2-naphthylmethyl)aminocarbonyl]-argininamide,

(38) (R,S)-N²-(diphenylacetyl)-N-[(4-hydroxyphenyl)methyl]-N⁵-methyl-N⁷-(methylaminocarbonyl)-argininamide,

(39) (R,S)-N²-(diphenylacetyl)-N⁵-methyl-N⁷-(methylaminocarbonyl)-N-[[4-(methylaminocarbonyloxy)phenyl]methyl]-argininamide,

(40) (R)-N²-(diphenylacetyl)-N-[(4-methylphenyl)methyl]-N⁷-(5-methyl-2-thiazolyl)-argininamide,

(41) (R)-N²-(diphenylacetyl)-N-[(4-hydroxyphenyl)methyl]-N⁷-(5-methyl-2-thiazolyl)-argininamide,

(42) (R)-N²-(diphenylacetyl)-N-[(4-hydroxyphenyl)methyl]-N⁷-phenyl-argininamide,

(43) (R)-N-[[4-(aminocarbonylaminomethyl)phenyl]methyl]-N²-(diphenylacetyl)-N⁷-(2-pyridinyl)-argininamide,

(44) (R)-N²-(diphenylacetyl)-N-[(4-hydroxyphenyl)methyl]-N⁷-(4-methyl-2-thiazolyl)-argininamide,

(45) (R)-N²-(diphenylacetyl)-N-[(4-methylphenyl)methyl]-N⁷-(4-methyl-2-thiazolyl)-argininamide,

(46) (R)-N²-(diphenylacetyl)-N-[(4-methylphenyl)methyl]-N⁷-(5-methyl-2-pyridinyl)-argininamide,

(47) (R)-N²-(diphenylacetyl)-N-[(4-hydroxyphenyl)methyl]-N⁷-(2-thiazolyl)-argininamide,

(48) (R)-N²-(diphenylacetyl)-N-[(4-hydroxyphenyl)methyl]-N⁷-(5-methyl-2-pyridinyl)-argininamide,

(49) (R)-N²-(diphenylacetyl)-N-methyl-N⁷-(4-methyl-2-thiazolyl)-N-(phenylmethyl)-argininamide,

(50) (R)-N²-(diphenylacetyl)-N⁷-[4-(3-phenylpropyl)-2-thiazolyl)-N-(phenylmethyl)-argininamide,

(51) (R)-N²-(diphenylacetyl)-N⁷-[4-(2-phenylethyl)-2-thiazolyl)-N-(phenylmethyl)-argininamide,

(52) (R)-N²-(diphenylacetyl)-N-[(4-hydroxyphenyl)methyl]-N⁷-methyl-argininamide,

(53) (R)-N²-(diphenylacetyl)-N⁷-[4-(2-phenylethyl)-2-thiazolyl)-N-[[4-(phenylmethoxy)phenyl]methyl]-argininamide,

(54) (R)-N²-(diphenylacetyl)-N-[[4-(phenylmethoxy)phenyl]-methyl]-N⁷-[4-(3-phenylpropyl)-2-thiazolyl]-argininamide,

(55) (R)-N²-(diphenylacetyl)-N⁷-(4-methyl-2-thiazolyl)-N-[[4-(phenylmethoxy)phenyl]methyl]-argininamide,

(56) (R,S)-N²-(diphenylacetyl)-N-[(4-hydroxyphenyl)methyl]-N⁷-[3-(methoxycarbonyl)-1-oxopropyl]-argininamide,

(57) (R)-N²-(diphenylacetyl)-N-[(4-hydroxyphenyl)methyl]-N⁷-[(4-pyridinyl)carbonyl]-argininamide,

(58) (R,S)-N-[[4-(aminocarbonylmethyl)phenyl]methyl]-N²-(diphenylacetyl)-N⁵-methyl-N⁷-(methylaminocarbonyl)-argininamide,

(59) (R)-N²-(diphenylacetyl)-N⁷-(4-methyl-2-thiazolyl)-N-methyl-N-[(4-(phenylmethoxy)phenyl]methyl]-argininamid and the salts thereof.

The compounds of general formula I and their precursors are prepared by methods known in principle, whilst processes derived from peptide chemistry (of for example Houben-Weyl, Methoden der Organischen Chemie, vol. 15/2) may particularly be used. The amino protecting groups used may be those described in Houben-Weyl, Methoden der Organischen Chemie, vol. 15/1, whilst urethane protecting groups, such as, for example, the fluorenylmethoxycarbonyl, phenylmethoxycarbonyl or tert.-butyloxycarbonyl group, are preferred. Any functional groups present in the side chain of the compounds of general formula I or in their precursors are additionally protected by suitable protecting groups to prevent side reactions (of for example: G. B. Fields et al., Int. J. Peptide Protein Res. 35, 161 (1990); T. W. Greene, Protective Groups in Organic Synthesis). Examples of side chain-protected amino acids of this kind include in particular Arg(NO₂), Arg(Mtr), Arg(di-Z), Arg(Pmc), Orn(Boc), Orn(Z), which are generally commercially obtainable, optionally in the form of their derivatives. Care should be taken in particular to ensure that so-called orthogonal combinations of protecting groups are used for protecting the α-amino and the side chain amino group, e.g.:

| Protection of the N (side chain) | Nᵃ-protection |
| --- | --- |
| p-toluenesulphonyl | phenylmethoxycarbonyl |
| | tert.butoxycarbonyl |
| phenylmethoxycarbonyl | (4-methoxyphenyl)methoxycarbonyl |
| | tert. butoxycarbonyl |
| | adamantyloxycarbonyl |
| | biphenylylisopropyloxycarbonyl |
| | isonicotinoyloxycarbonyl |
| | o-nitrophenylsulphenyl |
| | formyl |
| tert. butoxycarbonyl | phenylmethoxycarbonyl |
| | p-toluenesulphonyl |
| | o-nitrophenylsulphenyl |
| | biphenylylisopropyloxycarbonyl |
| | 9-fluorenylmethoxycarbonyl |
| acetyl, trifluoroacetyl, formyl, (2-chlorophenyl)-methoxycarbonyl, (4-chlorophenyl)methoxycarbonyl, 4-(nitrophenyl)methoxycarbonyl, phthaloyl | tert.butoxycarbonyl |

For the actual coupling the methods known from peptide chemistry (cf for example Houben-Weyl, Methoden der Organischen Chemie, vol. 15/2) are used. Preferably, carbodiimides, such as e.g. dicyclohexylcarbodiimide (DCC), diisopropylcarbodiimide (DIC) or ethyl-(3-dimethylaminopropyl)-carbodiimide, O-(1H-benzotriazol-1-yl)-N,N,N',N'-tetramethyluroniumhexafluorophosphate (HBTU) or -tetrafluoroborate (TBTU) or 1H-benzotriazol-1-yl-oxy-tris-(dimethylamino)-phosphoniumhexafluorophosphate (BOP), are used. If desired, it is also possible to suppress racemisation or speed up the reaction by the addition of 1-hydroxybenzotriazole (HOBt) or 3-hydroxy-4-oxo-3,4-dihydro-1,2,3-benzotriazine (HOObt). The couplings are normally carried out with equimolar amounts of the coupling components and the coupling reagent in solvents such as dichloromethane, tetrahydrofuran, acetonitrile, dimethylformamide (DMF), dimethylacetamide (DMA), N-methylpyrrolidone (NMP) or mixtures thereof and at temperatures of between −30 and +30° C., preferably −20 and +20° C. If necessary, N-ethyl-diisopropylamine (DIEA; Hünig base) is preferred as an additional auxiliary base.

The so-called "anhydride method" (cf. also: M. Bodanszky, "Peptide Chemistry", Springer-Verlag 1988, P. 58–59; M. Bodanszky, "Principles of Peptide Synthesis", Springer-Verlag 1984, P. 21–27) is used as another coupling method for synthesising compounds of general formula I. It is preferable to use the "mixed anhydride method" in the variant according to Vaughan (J. R. Vaughan Jr., J. Amer. Chem.Soc. 73, 3547 (1951)), in which the mixed anhydride is obtained from the optionally N²-protected α-amino acid and the monoisobutyl carbonate which are to be coupled, using isobutyl chlorocarbonate in the presence of bases such as 4-methylmorpholine or 4-ethylmorpholine. The preparation of this mixed anhydride and the coupling with amines are carried out in a one-pot method, using the abovementioned solvents and at temperatures between −20 and +20° C., preferably 0 and +20° C.

Any protecting groups present in the α-amino acid side chain and not wanted in the end product are finally cleaved after the synthesis of the N- and C-terminally substituted amino acid derivative with suitable reagents which are also in principle known from the literature, namely arylsulphonyl and hetarylsulphonyl protecting groups are preferably cleaved acidolytically, i.e. by the action of strong acids, preferably trifluoroacetic acid, nitro and arylmethoxycarbonyl protecting groups are cleaved hydrogenolytically, e.g. with hydrogen in the presence of palladium black and using glacial acetic acid as solvent. If the substrate contains functions which are sensitive to hydrogenolysis, e.g. halogen atoms, such as chlorine, bromine or iodine, a phenylmethanol or hetarylmethanol function or another benzylheteroatom bond, particularly a benzyl-oxygen bond, the cleaving of the nitro group may also be carried out non-hydrogenolytically, e.g. with zinc/2N trifluoroacetic acid (cf also: A. Turan, A. Patthy and S. Bajusz, Acta Chim. Acad. Sci. Hung., Tom. 85 (3), 327–332 [1975]; C. A. 83, 206526y [1975]), with tin(II)chloride in 60% aqueous formic acid (cf also: SUNSTAR KK, JA-A-3271-299), with zinc in the presence of acetic acid (cf also: A. Malabarba, P. Ferrari, G. Cietto, R. Pallanza and M. Berti, J. Antibiot. 42 (12) 1800–1816 (1989)) or excess aqueous 20% titanium(III) chloride in aqueous methanol and in the presence of aqueous ammonium acetate buffer at 24° C. (cf also: R. M. Freidinger, R. Hirschmann and D. F. Veber, J. Org. Chem. 43 (25), 4800–4803 [1978]).

The following processes are particularly suitable for preparing the compounds of general formula I according to the invention:

a) Coupling compounds of general formula II,

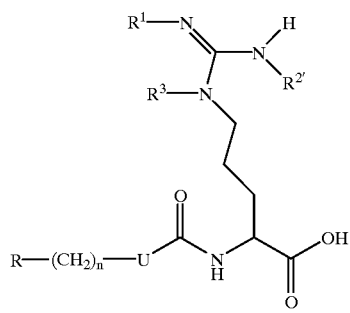

(II)

wherein

R, $R^1$, $R^3$, U and n are as hereinbefore defined and $R^{2\prime}$ has the meanings given for R2 hereinbefore or also denotes one of the protecting groups mentioned hereinbefore for the protection of the side chain of arginine, with compounds of general formula III,

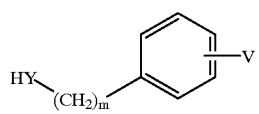

(III)

wherein m, V and Y have the meanings given hereinbefore, and, if necessary, subsequently cleaving protecting groups using the methods described hereinbefore.

The coupling is carried out using the methods known from peptide chemistry and described hereinbefore, particularly using DCC, DIC, HBTU, TBTU or BOP as reagents or using the mixed anhydride method.

If the starting compound II used is enantiomerically pure, then, if U does not represent an oxygen atom or an NH group, partial racemisation must be expected during the coupling step if triethylamine is used as the auxiliary base and dimethylformamide, dimethylacetamide or N-methylpyrrolidone is used as solvent and in some cases substantial or even quantitative racemisation must be expected.

For preparing compounds of general formula I wherein Y denotes an oxygen atom, the variant recommended by A. Hassner and V. Alexonian, Tetrahedron Letters 1978, 4475–4478, i.e. reaction at ambient temperature and in the presence of DCC and 4-(1-pyrrolidinyl)pyridine as base, has proved particularly successful.

b) For preparing compounds of general formula I wherein U has the meanings given hereinbefore with the exception of an oxygen atom and the —NH— group:

Coupling compounds of general formula IV,

(IV)

wherein

R and n are as hereinbefore defined, $U^1$ denotes a single bond and Nu a leaving group, for example the hydroxy group, a halogen atom, such as the chlorine, bromine or iodine atom, an alkylsulphonyloxy group with 1 to 10 carbon atoms, a phenylsulphonyloxy or naphthylsulphonyloxy group optionally mono-, di- or trisubstituted by chlorine or bromine atoms, by methyl or nitro groups, whilst the substituents may be identical or different, with α-amino acid derivatives of general formula V,

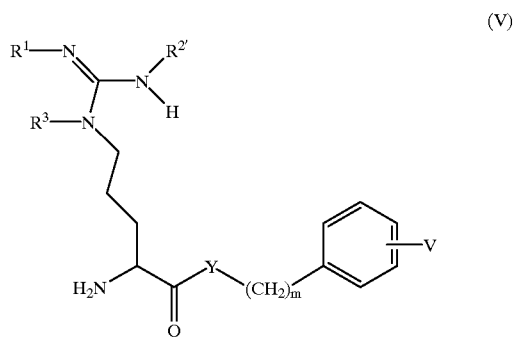

(V)

wherein $R^1$, $R^3$, Y, m and V are as hereinbefore defined and $R^{2\prime}$ has the meanings given for $R^2$ hereinbefore or also denotes one of the protecting groups mentioned hereinbefore for the protection of the side chain of arginine, and, if necessary, subsequently cleaving protecting groups using the methods described hereinbefore.

If in general formula IV Nu denotes the hydroxy group, the coupling methods known from peptide chemistry and discussed in detail above will be used, particularly using the abovementioned coupling reagents DCC, DIC, HBTU, TBTU or BOP, or the mixed anhydride method will be used.

If in general formula IV Nu denotes a halogen atom, an alkyl or arylsulphonyloxy group, the reaction is carried out under Schotten-Baumann or Einhorn conditions, i.e. the components are reacted in the presence of at least one equivalent of an auxiliary base at temperatures of between −50° C. and +120° C., preferably −10° C. and +30° C., and optionally in the presence of solvents. Examples of preferred auxiliary bases include alkali and alkaline earth hydroxides, for example sodium hydroxide, potassium hydroxide or barium hydroxide, alkali metal carbonates, e.g. sodium carbonate, potassium carbonate or caesium carbonate, alkali metal acetates, e.g. sodium or potassium acetate, and tertiary amines, for example pyridine, 2,4,6-trimethylpyridine, quinoline, triethylamine, N-ethyl-diisopropylamine, N-ethyl-dicyclohexylamine, 1,4-diazabicyclo[2,2,2]octane or ],8-diazabicyclo[5,4,0]undec-7-ene, preferred solvents include for example dichloromethane, tetrahydrofuran, 1,4-dioxan, acetonitrile, dimethylformamide, dimethylacetamide, N-methyl-pyrrolidone or mixtures thereof; if alkali or alkaline earth hydroxides, alkali metal carbonates or acetates are used as auxiliary bases, water may also be added to the reaction mixture as a cosolvent.

c) For preparing compounds of general formula I wherein Y denotes an oxygen atom:

Transesterifying amino acid esters of general formula VI,

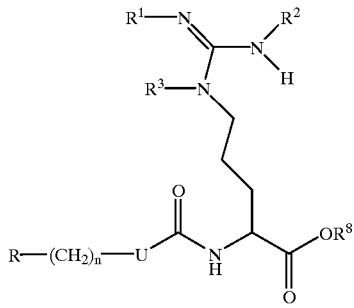

(VI)

wherein

R, $R^1$, $R^2$, $R^3$, U and n are as hereinbefore defined and $R^8$ denotes an alkyl group with 1 to 4 carbon atoms, with an alcohol of general formula VII,

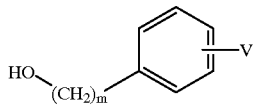

(VII)

wherein m and V are as hereinbefore defined.

The transesterification may be catalysed with an acid or alkaline catalyst (cf. also: J. March, "Advanced Organic Chemistry", John Wiley & Sons, Third Edition, 1985, P. 351–352). Preferred alkaline catalysts are the corresponding alkali metal alkoxides which are easily obtained from the alcohols of general formulae VII or $R^8OH$, e.g. lithium, sodium or potassium alkoxides; preferred acid catalysts include, in addition to anhydrous hydrogen chloride, in particular, sulphuric acid, p-toluene-sulphonic acid, naphthalene-1- or -2-sulphonic acid or acid ion exchanger freshly charged with hydrogen ions, e.g. Wofatit KPS z.A. The equilibrium between the two esters in the equation is shifted in the right direction in this process by distilling off the more volatile alcohol $R^8OH$.

With alkaline catalysis, if the starting compound VI used was enantiomerically pure, the end product of general formula I is obtained as a racemate.

d) For preparing compounds of general formula I wherein Y denotes an oxygen atom:

Reacting salts, preferably alkali metal salts, of the carboxylic acids of general formula II,

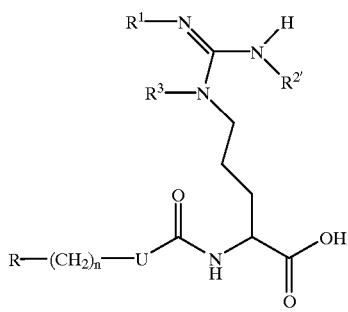

(II)

wherein

R, $R^1$, $R^3$, U and n are as hereinbefore defined and $R^{2'}$ has the meanings given for $R^2$ hereinbefore or also denotes one of the protecting groups mentioned hereinbefore for the protection of the side chain of arginine, with compounds of general formula VIII,

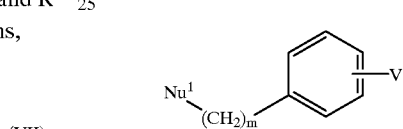

(VIII)

wherein m and V are as hereinbefore defined and $Nu^1$ denotes a leaving group, for example a halogen atom, such as the chlorine, bromine or iodine atom, an alkylsulphonyloxy group with 1 to 10 carbon atoms, a phenylsulphonyloxy or naphthylsulphonyloxy group optionally mono-, di- or trisubstituted by chlorine or bromine atoms, or by methyl or nitro groups, whilst the substituents may be identical or different, and, if necessary, subsequently cleaving protecting groups using the methods described hereinbefore.

The reaction is carried out in a suitable solvent, preferably in the presence of dipolar aprotic solvents such as dimethylsulphoxide, hexamethylphosphotriamide, 1,3-dimethyl-2-imidazolidinone, dimethylacetamide, dimethylformamide or N-methyl-2-pyrrolidinone at temperatures of between −10° C. and +50° C., but preferably at ambient temperature. The alkali metal salts of the carboxylic acids of general formula II are preferably produced in situ by the action of alkali metal carbonates, e.g. potassium or caesium carbonate, alkali metal hydroxides, e.g. sodium hydroxide, or alkali metal hydrides, e.g. sodium hydride, on the compounds of general formula II, before the compounds of general formula VIII are added (cf. also: J. E. Schaw, D. C. Kunerth and J. J. Sherry, Tetrahedron Letters 1973, 689–692; A. M. MacLeod, K. J. Merchant, M. A. Cascieri, P. Sadowski, E. Ber, C. J. Serain and R. Baker, J. Med. Chem. 36, 2044–2045 (1993); A. Rosowsky, R. A. Forsch, Ch. -P. Yu, H. Lazarus and G. P. Beardsley, J. Med. Chem. 27, 605–609 (1984)).

e) Reacting compounds of general formula IX,

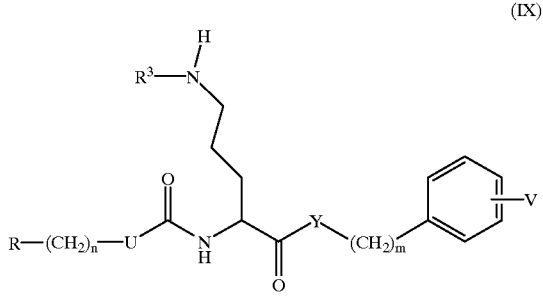

(IX)

wherein
R, $R^3$, U, V, Y, m and n are as hereinbefore defined,
with carbonic acid derivatives of general formula X,

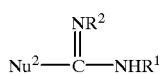

(X)

wherein
$R^1$ and $R^2$ are as hereinbefore defined and $Nu^2$ is a leaving group, for example an alkoxy, alkylthio, alkylsulphynyl or alkylsulphonyl group each with 1 to 10 carbon atoms in the alkyl moiety, e.g. the methoxy, ethoxy, methylthio, ethylthio, methylsulphynyl, ethylsulphynyl, propylsulphynyl, isopropylsulphynyl, methylsulphonyl or ethylsulphonyl group, 44444the chlorine atom, the $SO_2H$, $SO_3H$ or $OPOCl_2$ group, or the group of general formula XI,

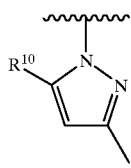

(XI)

wherein
$R^9$ and $R^{10}$, which may be identical or different, denote hydrogen atoms or alkyl groups with 1 to 3 carbon atoms.

Occasionally, for example if $Nu^2$ is an alkoxy group, it is advantageous to use, instead of the compounds of general formula X, the inorganic acid salts thereof, e.g. the neutral sulphates or the hydrochlorides thereof.

The reactions are carried out analogously to processes known from the literature (cf. G. B. L. Smith, J. Amer. Chem. Soc. 51, 476 [1929]; B. Rathke, Chem. Ber. 17, 297 [1884]; R. Phillips and H. T. Clarke, J. Amer. Chem. Soc. 45, 1755 [1923]; S. J. Angyal and W. K. Warburton, J. Amer. Chem. Soc. 73, 2492 [1951]; H. Lecher and F. Graf, Chem. Ber. 56, 1326 [1923]; J. Wityak, S. J. Gould, S. J. Hein and D. A. Keszler, J. Org. Chem. 52, 2179 [1987]; T. Teraji, Y. Nakai, G. J. Durant, WO-A-81/00109, Chem. Abstr. 94, 192336z [1981]; C. A. Maryanoff, R. C. Stanzione, J. N. Plampin and J. E. Mills, J. Org. Chem. 51, 1882–1884 [1986]; A. E. Miller and J. J. Bischoff, Synthesis 1986, 777; R. A. B. Bannard, A. A. Casselman, W. F. Cockburn and G. M. Brown, Can. J. Chem. 36, 1541 [1958]; Aktieselskabet Grea, Copenhagen, DE 28 26 452-C2; K. Kim, Y-T. Lin and H. P. Mosher, Tetrah. Letters, 29, 3183–3186 [1988]; H. B. Arzeno et al., Syhth. Commun. 20, 3433–3437 [1990]; H. Bredereck and K. Bredereck, Chem. Ber. 94, 2278 [1961]; H. Eilingsfeld, G. Neubauer, M. Seefelder and H. Weidinger, Chem. Ber. 97, 1232 [1964]; P. Pruszynski, Can. J. Chem. 65, 626 [1987]; D. F. Gavin, W. J. Schnabel, E. Kober and M. A. Robinson, J. Org. Chem. 32, 2511 [1967]; N. K. Hart, S. R. Johns, J. A. Lamberton and R. I. Willing, Aust. J. Chem. 23, 1679 [1970]; CIBA Ltd., Belgian Patent 655 403; Chem. Abstr. 64, 17481 [1966]; J. P. Greenstein, J. Org. Chem. 2, 480 [1937]; F. L. Scott and J. Reilly, J. Amer. Chem. Soc. 74, 4562 [1952]; W. R. Roush and A. E. Walts, J. Amer. Chem. Soc. 106, 721 [1984], M. P. Bernatowicz, Y. Wu and G. R. Matsueda, J. Org. Chem. 57, 2497–2502 [1992]; H. Tsunematsu, T. Imamura and P. Makisumi, J. Biochem. 94, 123–128 [1983]) at temperatures of between 0° C. and +100° C., preferably +40° C. and +80° C., and using inert solvents, for example dichloromethane, tetrahydrofuran, 1,4-dioxan, acetonitrile, dimethylformamide, dimethylacetamide, N-methylpyrrolidone or mixtures thereof and—depending on the nature of the $Nu^2$ group—often in the presence of auxiliary bases, particularly alkali metal carbonates such as sodium or potassium carbonate, or tertiary amines, preferably N-ethyldiisopropylamine or triethylamine.

f) Reacting the uronium salts or thiuronium salts of general formula XII,

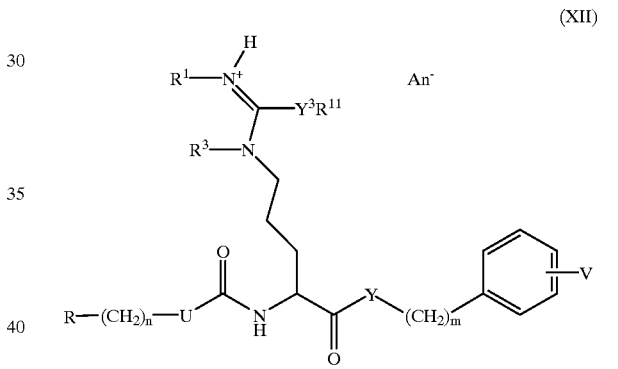

(XII)

wherein
R, $R^1$, $R^3$, U, V, Y, n and m are as hereinbefore defined, $R^{11}$ denotes an alkyl group with 1 to 4 carbon atoms or the phenyl group, $Y^3$ denotes the oxygen or sulphur atom and $An^-$ denotes a monovalent anion, for example a chloride, bromide, iodide, methylsulphate, methanesulphonate or toluenesulphonate anion and ½ $SO_4^{2-}$, or the corresponding free isoureas or isothioureas
with amines of general formula XIII,

$R^2$—$NH_2$ (XIII)

wherein $R^2$ is as hereinbefore defined.

The reaction is carried out at temperatures of between 0 and 110° C., preferably between +15 and +60° C., and optionally in a suitable solvent, for example in water, dimethylformamide, dimethylacetamide, dimethylsulphoxide, N-methylpyrrolidone, tetrahydrofuran, dioxan, an alcohol such as methanol or ethanol or in a mixture thereof, whilst the compounds of general formula I are obtained directly as salts with the acid HAn. If instead of the uronium salts or thiuronium salts XII the fundamental bases, the corresponding free isoureas or isothioureas are used in the reaction, 1 equivalent of a weak acid, preferably acetic acid, must be added to the mixture.

g) For preparing compounds of general formula I wherein U denotes the oxygen atom or the —NH group:
Reacting isocyanates of general formula XIV,

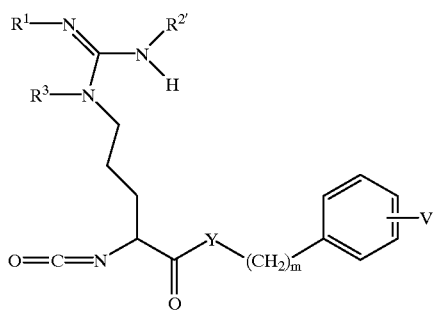

(XIV)

wherein
$R^1$, $R^3$, V, Y and m are as hereinbefore defined and $R^{2'}$ has the meanings given for $R^2$ hereinbefore or also denotes one of the protecting groups mentioned hereinbefore for the protection of the side chain of arginine,
with compounds of general formula XV,

R—$(CH_2)_n$—$U^2$—H           (XV)

wherein
R and n are as hereinbefore defined and $U^2$ denotes the oxygen atom or the —NH— group, and, if necessary, subsequently cleaving protecting groups using the methods described hereinbefore.

The reaction is carried out at temperatures of between 0° C. and 150° C., preferably between 20° C. and 100° C., and optionally in the presence of anhydrous solvents, e.g. tetrahydrofuran, 1,4-dioxan, dimethylformamide, dimethylacetamide, N-methyl-2-pyrrolidone or 1,3-dimethyl-2-imidazolidinone or mixtures thereof.

h) For preparing compounds of general formula I wherein U represents the —NH— group:
Reacting isocyanates of general formula XVI,

R—$(CH_2)_n$—N=C=O           (XVI)

wherein
R and n are as hereinbefore defined,
with α-amino acid derivatives of general formula V,

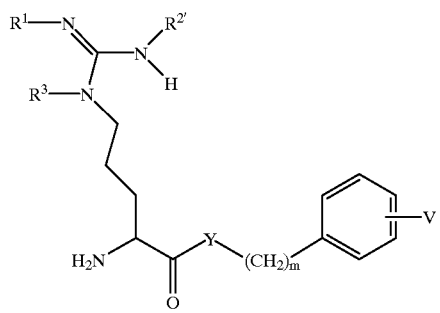

(V)

wherein
$R^1$, $R^3$, Y, m and V are as hereinbefore defined and $R^{2'}$ has the meanings given for $R^2$ hereinbefore or also denotes one of the protecting groups mentioned hereinbefore for the protection of the side chain of arginine, and, if necessary, subsequently cleaving protecting groups using the methods described hereinbefore.

The reaction is carried out at temperatures of between 0 and 150° C., preferably at temperatures of between 20 and 100° C., and optionally in the presence of anhydrous solvents, e.g. tetrahydrofuran, 1, 4-dioxan, dimethylformamide, dimethylacetamide, N-methyl-2-pyrrolidone or 1,3-dimethyl-2-imidazolidinone.

i) For preparing compounds of general formula I wherein V denotes the group —$(CH_2)_o$—$Y^1$—W—$Y^2$ wherein
o and W are as hereinbefore defined,
$Y^1$ represents the oxygen atom or the group —$NR^5$, in which
$R^5$ denotes a hydrogen atom or a straight-chained or branched alkyl group with 1 to 6 carbon atoms, and
$Y^2$ denotes a straight-chained or branched alkyl group with 1 to 10 carbon atoms optionally substituted by a hydroxy, alkoxycarbonyl or aminocarbonyl group, a cycloalkyl group with 4 to 10 carbon atoms, a straight-chained or branched alkoxy group with 1 to 5 carbon atoms, an aminoalkyl, alkylaminoalkyl, dialkylaminoalkyl, phenylmethoxy or 2-phenylethoxy group, a phenyl or phenylalkyl group with 1 to 3 carbon atoms in the alkyl moiety optionally mono-, di- or trisubstituted in the phenyl moiety by fluorine, chlorine or bromine atoms, by methyl, trifluoromethyl, cyano, amino, hydroxy, methoxy, acetyl, acetylamino, aminocarbonyl, methylaminocarbonyl or dimethylaminocarbonyl groups, or
the —$NR^6R^7$ group wherein
$R^6$ denotes a hydrogen atom, a straight-chained or branched alkyl group with 1 to 6 carbon atoms optionally substituted by a hydroxy, carboxy, alkoxycarbonyl or dialkylamino group with the proviso that the hydroxy group is not bound in the 1-position of the alkyl group, a cycloalkyl group with 4 to 8 carbon atoms or a phenyl, phenylmethyl, 2-phenylethyl or 3-phenylpropyl group optionally mono-, di- or trisubstituted in the phenyl moiety by fluorine, chlorine or bromine atoms, by methyl, trifluoromethyl, hydroxy, methoxy, amino, acetylamino, aminocarbonyl, methylaminocarbonyl, dimethylaminocarbonyl or cyano groups, whilst the substituents may be identical or different, or an alkanoyl, benzoyl, phenylalkanoyl, alkoxycarbonyl or aminocarbonyl group and
$R^7$ has the meanings given for R6 with the exception of a phenyl, alkanoyl, benzoyl, phenylalkanoyl, alkoxycarbonyl or aminocarbonyl group:
Transforming compounds of general formula XVII,

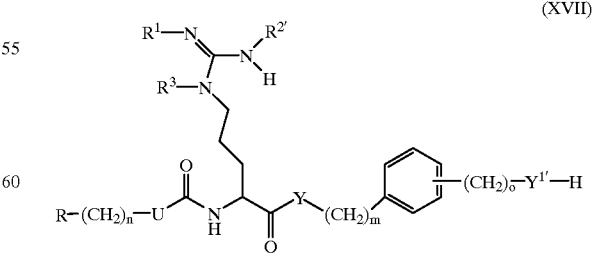

(XVII)

wherein
m, n, o, R, $R^1$, $R^3$, U and Y are as hereinbefore defined,
$R^{2'}$ has the meanings given for $R^2$ hereinbefore or also denotes one of the protecting groups mentioned hereinbefore for the protection of the side chain of arginine and $Y^{1'}$ denotes the oxygen atom or the group —$NR^5$, wherein $R^5$ represents the hydrogen atom or a straight-chained or branched alkyl group with 1 to 6 carbon atoms, at the ($Y^{1'}$—H) function and, if necessary, subsequently cleaving protecting groups using the methods described hereinbefore and/or further transforming the group V obtained in the first instance.

The transformation at the ($Y^{1'}$—H) function may, depending on the reagent used, be carried out either without a solvent or in a suitable solvent, e.g. in water, alcohols such as methanol, ethanol or propanol, in N-methylpyrrolidinone, dimethylformamide or dimethylacetamide or mixtures thereof, optionally in the presence of inorganic acids, for example hydrochloric acid or sulphuric acid, organic or inorganic bases, for example triethylamine, Hünig base or sodium carbonate, and may optionally be followed by treatment with ammonia, with inorganic acids such as hydrochloric acid or sulphuric acid or with organic acids such as trifluoroacetic acid at temperatures of between 0 and 150° C., preferably between 20 and 100° C.

Preferably
- by reacting compounds of general formula XVII wherein $Y^{1'}$ is the —$NR^5$ group, whilst $R^5$ represents the hydrogen atom or a straight-chained or branched alkyl group with 1 to 6 carbon atoms, with alkali metal cyanates, e.g. sodium cyanate, in the presence of inorganic acids, e.g. hydrochloric acid, compounds of general formula I are obtained wherein V denotes the group —$(CH_2)_o$—$NR^5$—CO—$NH_2$, whilst o is as hereinbefore defined and $R^5$ represents a hydrogen atom or a straight-chained or branched alkyl group with 1 to 6 carbon atoms (cf. also: Org. Synth., Coll. Vol. IV, P. 515),
- by reaction with acetic anhydride in alcohols, e.g. in ethanol, compounds of general formula I are obtained wherein V denotes the group —$(CH_2)_o$—$NR^5$—CO—$CH_3$, whilst o is as hereinbefore defined and $R^5$ represents a hydrogen atom or a straight-chained or branched alkyl group with 1 to 6 carbon atoms,
- by reaction with ethyl chlorocarbonate in the presence of triethylamine, compounds of general formula I are obtained wherein V denotes the group —$(CH_2)_o$—$NR^5$—CO—$OC_2H_5$, whilst o is as hereinbefore defined and $R^5$ represents a hydrogen atom or a straight-chained or branched alkyl group with 1 to 6 carbon atoms,
- by reaction with N-(tert.butyl)-chlorsulphonic acid amide, compounds of general formula I are obtained wherein V represents the group —$(CH_2)_o$—$NR^5$—$SO_2$—NH—$C(CH_3)_3$, and by subsequent treatment with trifluoroacetic acid, compounds of general formula I are obtained wherein V denotes the group —$(CH_2)_o$—$NR^5$—$SO_2$—$NH_2$, whilst o is as hereinbefore defined and $R^5$ represents a hydrogen atom or a straight-chained or branched alkyl group with 1 to 6 carbon atoms, whilst it should be noted that if the group $R^{2'}$ denotes the Pmc protecting group, this is also removed,
- by reaction with benzoyl chloride, compounds of general formula I are obtained wherein V represents the group —$(CH_2)_o$—$NR^5$—CO—$C_6H_5$, whilst o is as hereinbefore defined and $R^5$ represents a hydrogen atom or a straight-chained or branched alkyl group with 1 to 6 carbon atoms,
- by reaction with methyl isocyanate, compounds of general formula I are obtained wherein V represents the group —$(CH_2)_o$—$NR^5$—CO—NH—$CH_3$, whilst o is as hereinbefore defined and $R^5$ represents a hydrogen atom or a straight-chained or branched alkyl group with 1 to 6 carbon atoms,
- by reaction with dimethylcarbamoyl chloride, compounds of general formula I are obtained wherein V represents the group —$(CH_2)_o$—$NR^5$—CO—$N(CH_3)_2$, whilst o is as hereinbefore defined and $R^5$ represents a hydrogen atom or a straight-chained or branched alkyl group with 1 to 6 carbon atoms,
- by reaction with nitrobiuret, compounds of general formula I are obtained wherein V represents the group —$(CH_2)_o$—$NR^5$—CO—NH—CO—$NH_2$, whilst o is as hereinbefore defined and R5 denotes a hydrogen atom or a straight-chained or branched alkyl group with 1 to 6 carbon atoms, (see also: T. L. Davis et al, J. Am. Chem. Soc. 51, 1801–1806 (1929)) and
- by reacting compounds of general formula XVII wherein $Y^{1'}$ denotes the oxygen atom with phenyl chlorocarbonate and subsequent aminolysis, compounds of general formula I are obtained wherein V denotes the group —$(CH_2)_o$—O—CO—$NH_2$, whilst o is as hereinbefore defined (see also: G. R. Allen, Jr., J. F. Poletto and M. J. Weiss, J. Org. Chem. 30, 2897–2904 (1965)).

j) For preparing compounds of general formula I wherein $R^1$ denotes a branched or unbranched aliphatic alkylcarbonyl group containing 2 to 5 carbon atoms, which may be substituted in the alkyl moiety by an alkoxycarbonyl or phenylalkoxycarbonyl group, by a phenyl group or by a 5- or 6-membered heteroaromatic ring linked via a carbon atom, or a benzoyl group wherein the phenyl moiety may also be replaced by a 5- or 6-membered heteroaromatic ring linked via a carbon atom, whilst the abovementioned 5-membered heteroaromatic rings may contain a nitrogen, an oxygen or sulphur atom or a nitrogen atom and an additional oxygen, sulphur or further nitrogen atom and may also be substituted at a nitrogen atom by an alkyl group, the 6-membered heteroaromatic rings contain 1, 2 or 3 nitrogen atoms, and the abovementioned phenyl groups may additionally be mono-, di- or at most trisubstituted, as may the heteroaromatic rings in their carbon skeleton, by fluorine, chlorine or bromine atoms, by alkyl groups, cycloalkyl groups with 3 to 8 carbon atoms, alkoxy, trifluoromethyl, alkoxycarbonylalkyl, carboxyalkyl, hydroxy, amino, acetylamino, propionylamino, aminocarbonyl, alkylaminocarbonyl, dialkylaminocarbonyl, alkanoyl, cyano, trifluoromethoxy, trifluoromethylthio, trifluoromethylsulphynyl or trifluoromethylsulphonyl groups, whilst the substituents may be identical or different:

Reacting compounds of general formula XVIII,

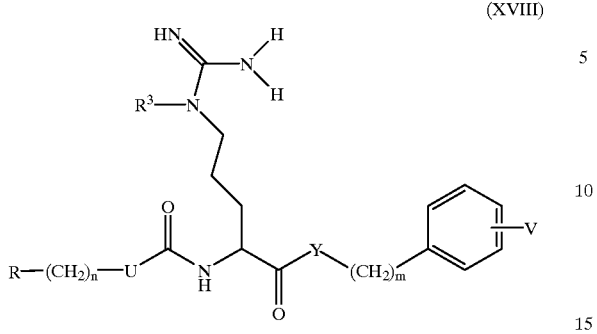

(XVIII)

wherein R, R³, U, V, Y, n and m are as hereinbefore defined, with a compound of general formula XIXa,

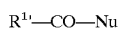 (XIXa)

wherein R¹ denotes a branched or unbranched aliphatic alkyl group containing 1 to 4 carbon atoms, which may be substituted by an alkoxycarbonyl or phenylalkoxycarbonyl group, by a phenyl group or by a 5- or 6-membered heteroaromatic ring linked via a carbon atom, a phenyl group or a 5- or 6-membered heteroaromatic ring linked via a carbon atom, whilst the abovementioned 5-membered heteroaromatic rings may contain a nitrogen, an oxygen or a sulphur atom or a nitrogen atom and an additional oxygen, sulphur or further nitrogen atom and may also be substituted at a nitrogen atom by an alkyl group, the 6-membered heteroaromatic rings may contain 1, 2 or 3 nitrogen atoms, and the abovementioned phenyl groups and all the heteroaromatic rings in their carbon skeleton may additionally be mono-, di- or at most trisubstituted by fluorine, chlorine or bromine atoms, by alkyl groups, cycloalkyl groups with 3 to 8 carbon atoms, alkoxy, trifluoromethyl, alkoxycarbonylalkyl, carboxyalkyl, hydroxy, amino, acetylamino, propionylamino, aminocarbonyl, alkylaminocarbonyl, dialkylaminocarbonyl, alkanoyl, cyano, trifluoromethoxy, trifluoromethylthio, trifluoromethylsulphynyl or trifluoromethylsulphonyl groups, whilst the substituents may be identical or different, and Nu denotes a leaving group, for example the hydroxy group, a halogen atom, such as the chlorine, bromine or iodine atom, an alkylsulphonyloxy group with 1 to 10 carbon atoms, a phenylsulphonyloxy or naphthylsulphonyloxy group optionally mono-, di- or trisubstituted by chlorine or bromine atoms, or by methyl or nitro groups, whilst the substituents may be identical or different.

The reaction is preferably carried out in aprotic solvents, for example in tetrahydrofuran, dioxan, acetonitrile, dimethylformamide, dimethylacetamide, hexamethylphosphotriamide, sulfolane, 1,3-dimethyl-2-imidazolidinone, 1,3-dimethyl-3,4,5,6-tetrahydro-2(1H)-pyrimidinone or mixtures thereof, in the presence of tertiary amines, for example pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, and at temperatures of between −20° C. and +60° C., most preferably between +15° C. and +30° C. Any acylatable functions present in group V are included in this reaction. Any reaction products diacylated in the guanidino function of the side chain and obtained as by-products can generally be separated quite easily using conventional chromatographic methods.

k) For preparing compounds of general formula I wherein R¹ denotes the aminocarbonyl group, which may be mono- or disubstituted at the nitrogen atom by alkyl, phenylalkyl, (1-naphthyl)alkyl, (2-naphthyl)alkyl, alkoxycarbonylalkyl, phenylalkoxycarbonylalkyl, phenoxycarbonylalkyl, diphenylalkyl, phenyl, cycloalkyl or cycloalkylalkyl groups each with 3 to 8 carbon atoms in the ring, whilst the substituents may be identical or different and the abovementioned phenyl groups may in turn, independently of one another, be mono- or disubstituted by fluorine, chlorine or bromine atoms, methyl, methoxy, alkoxycarbonylmethoxy, hydroxy or trifluoromethyl groups:

Reacting compounds of general formula XVIII,

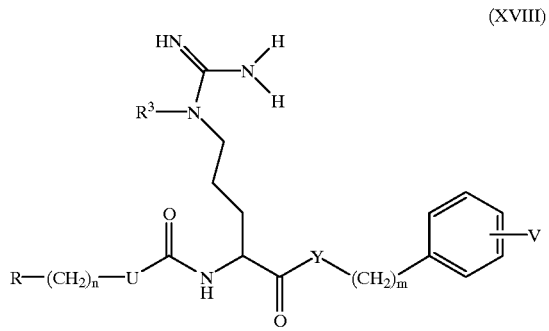

(XVIII)

wherein R, R³, U, V, Y, n and m are as hereinbefore defined, with a compound of general formula XIXb,

 (XIXb)

wherein R¹''' denotes an alkyl, phenylalkyl, (1-naphthyl)alkyl, (2-naphthyl)alkyl, alkoxycarbonylalkyl, phenylalkoxycarbonylalkyl, phenoxycarbonylalkyl, diphenylalkyl, phenyl, cycloalkyl or cycloalkylalkyl groups each with 3 to 8 carbon atoms in the cycloalkane ring may be mono- or disubstituted [sic], whilst the substituents may be identical or different and the abovementioned phenyl groups may in turn be mono- or disubstituted independently of one another by fluorine, chlorine or bromine atoms, methyl, methoxy, alkoxycarbonylmethoxy, hydroxy or trifluoromethyl groups, and Nu denotes a leaving group, for example the hydroxy group, a halogen atom, such as the chlorine, bromine or iodine atom, an alkylsulphonyloxy group with 1 to 10 carbon atoms, a phenylsulphonyloxy or naphthylsulphonyloxy group optionally mono-, di- or trisubstituted by chlorine or bromine atoms or by methyl or nitro groups, whilst the substituents may be identical or different.

The reaction is preferably carried out in aprotic solvents, for example in tetrahydrofuran, dioxan, acetonitrile, dimethylformamide, dimethylacetamide, hexamethylphosphotriamide, sulfolane, 1,3-dimethyl-2- imidazolidinone, 1,3-dimethyl-3,4,5,6-tetrahydro-2(1H)-pyrimidinone or mixtures thereof, in the presence of tertiary amines, for example pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, and at temperatures of between −20° C. and +60° C., most preferably between +15° C. and +30° C. Any acylatable functions present in group V are included in this reaction. Any reaction products obtained as by-products which are diacylated in the guanidino function of the side chain can generally be separated off quite easily using conventional chromatographic methods.

l) For preparing compounds of general formula I wherein
R¹ denotes an alkoxycarbonyl or phenylalkoxycarbonyl group, whilst the phenyl moiety may in its turn be mono- or disubstituted by fluorine, chlorine or bromine atoms, methyl, methoxy, alkoxycarbonylmethoxy, hydroxy or trifluoromethyl groups and the substituents in each case may be identical or different:
Reacting compounds of general formula XVIII,

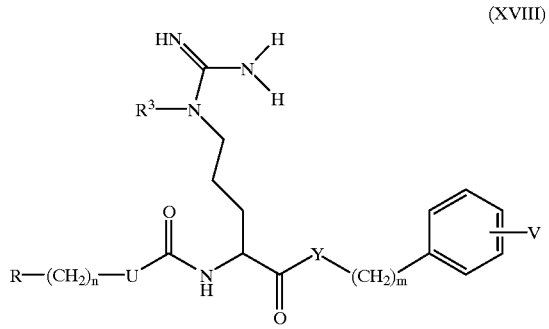

wherein R, R³, U, V, Y, n and m are as hereinbefore defined, with a compound of general formula XIXc,

R¹'''—O—CO—Cl (XIXC)

wherein R¹'''
denotes an alkyl or phenylalkyl group, in which the phenyl moiety may in its turn be mono- or disubstituted by fluorine, chlorine or bromine atoms, methyl, methoxy, alkoxycarbonylmethoxy, hydroxy or trifluoromethyl groups, whilst the substituents in each case may be identical or different,
and Nu denotes a leaving group, for example the hydroxy group, a halogen atom, such as the chlorine, bromine or iodine atom, an alkylsulphonyloxy group with 1 to 10 carbon atoms, a phenylsulphonyloxy or naphthylsulphonyloxy group optionally mono-, di- or trisubstituted by chlorine or bromine atoms, or by methyl or nitro groups, whilst the substituents may be identical or different.

The reaction is preferably carried out in aprotic solvents, for example in tetrahydrofuran, dioxan, acetonitrile, dimethylformamide, dimethylacetamide, hexamethyl phosphotriamide, sulfolane, 1,3-dimethyl-2-imidazolidinone, 1,3-dimethyl-3,4,5,6-tetrahydro-2(1H)-pyrimidinone or mixtures thereof, in the presence of tertiary amines, for example pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]undec-7-ene, and at temperatures of between −20° C. and +60° C., most preferably between +15° C. and +30° C. Any acylatable functions present in group V are included in this reaction. Any reaction products obtained as by-products which are diacylated in the guanidino function of the side chain can generally be separated off quite easily using conventional chromatographic methods.

m) For preparing the compounds of general formula XX covered by general formula I

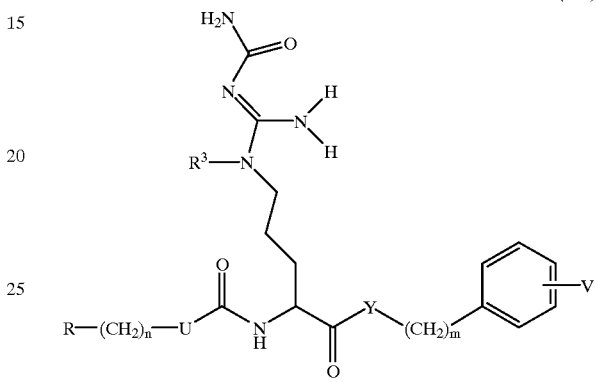

wherein R, R², R³, U, V, Y, n and m are as hereinbefore defined:

Partial hydrolysis of cyanoguanidines of general formula XXI,

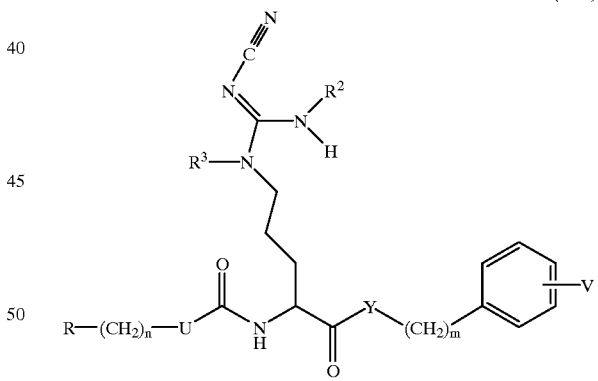

wherein R, R², R³, U, V, Y, n and m are as hereinbefore defined, by the action of strong aqueous acids, preferably aqueous trifluoroacetic acid, at temperatures of between 0° C. and +70° C., preferably +15° C. and +45° C. (see also: P. Theobald, J. Porter, C. Rivier, A. Corrigan, W. Hook, R. Siraganian, M. Perrin, W. Vale and J. Rivier, J. Med. Chem. 34, 2395–2402 (1991); P. J. Garratt, P. N. Thorn and R. Wrigglesworth, Tetrahedron 49, 6885–6898 (1993)). Water-miscible cosolvents, for example tetrahydrofuran or dioxan, may be added to the reaction mixture, but the reaction will also succeed in the absence of any additional solvents.

n) For preparing the compounds of general formula XXII covered by general formula I,

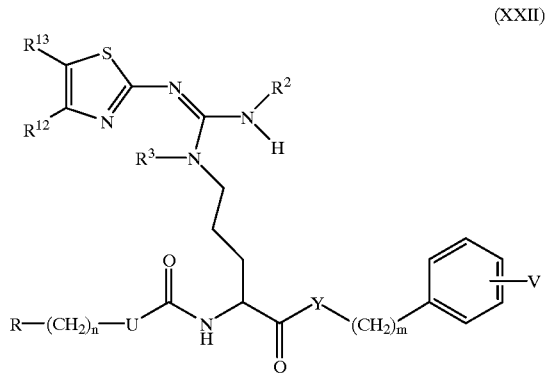
(XXII)

wherein R, $R^2$, $R^3$, U, V, Y, m and n are as hereinbefore defined and $R^{12}$ and $R^{13}$ independently of one another represent a hydrogen atom, an alkyl group with 1 to 5 carbon atoms, a cycloalkyl group with 3 to 8 carbon atoms or a phenylalkyl group with 1 to 5 carbon atoms in the alkyl moiety, whilst these groups may be identical or different:

Converting cyanoguanidines of general formula XXI,

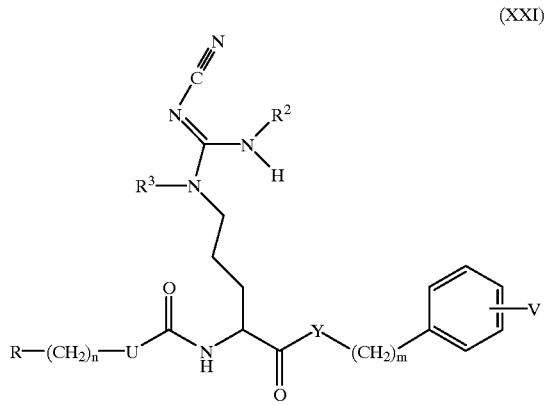
(XXI)

wherein R, $R^2$, $R^3$, U, V, Y, n and m are as hereinbefore defined, into aminothiocarbonylguanidines of general formula XXIII,

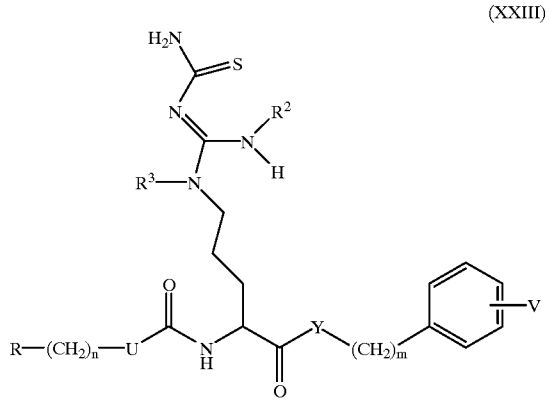
(XXIII)

wherein R, $R^2$, $R^3$, U, V, Y, n and m are as hereinbefore defined, and subsequently reacting with α-halocarbonyl compounds of general formula XXIV, $$R^{12}\text{—CO—CH(Hal)—}R^{13} \quad (XXIV)$$

wherein $R^{12}$ and $R^{13}$ independently of one another represent a hydrogen atom, an alkyl group with 1 to 5 carbon atoms, a cycloalkyl group with 3 to 8 carbon atoms or a phenylalkyl group with 1 to 5 carbon atoms in the alkyl moiety, whilst these groups may be identical or different, and Hal denotes a halogen atom, for example a chlorine, bromine or iodine atom, under the conditions of a thiazole synthesis according to Hantzsch. If for example a chloromethylketone of general formula $R^{12}$—CO—$CH_2$—Cl, wherein $R^{12}$ is as hereinbefore defined, is used as the halocarbonyl compound, thiazoles of general formula XXIIa are obtained,

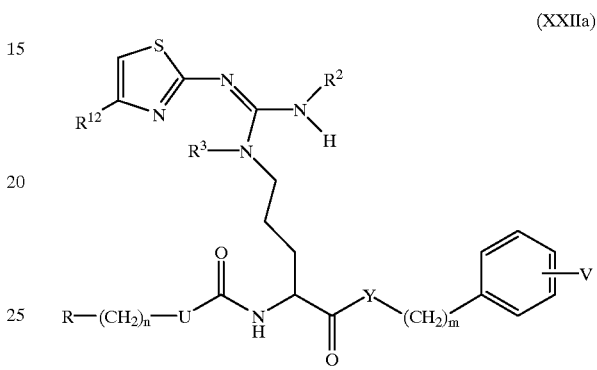
(XXIIa)

but if an α-haloaldehyde of general formula $R^{13}$—CHHal—CH=O wherein $R^{13}$ is as hereinbefore defined is used, or more appropriately a mixture of an aldehyde of general formula $R^{13}$—$CH_2$—CH=O and iodine is used, which in situ forms the α-iodoaldehyde required, thiazoles of general formula XXIIb are obtained.

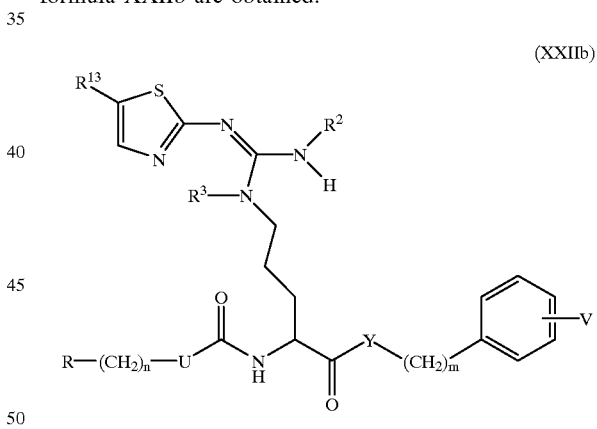
(XXIIb)

The conversion of the cyanoguanidines of general formula XXI into the aminothiocarbonylguanidines of general formula XXIII is most easily carried out by treating with hydrogen sulphide at temperatures of between ambient temperature and 100° C., preferably between 40° C. and 80° C. (cf. also: F. Kurzer, J.Chem. Soc. 1955, 1–6; Org. Synth., Coll. Vol. 4, 502–504 (1963)). Pyridine is the preferred solvent for this reaction. The reaction of the aminothiocarbonyl compounds of general formula XXIII to obtain the thiazoles of general formula XXII is preferably carried out in boiling acetone and first yields the hydrohalic acid salts of the thiazoles of general formula XXII, which are only converted into the free bases in the course of working up, particularly during column or flash chromatography in the presence of ammonia-containing eluants. The reaction may, however, also be carried out in the presence of weak inorganic bases, particularly sodium hydrogen carbonate, and then directly yields the free bases of general formula XXII.

o) For preparing compounds of general formula I wherein U denotes the oxygen atom:

Aminolysis of chlorocarbonates of general formula XXV,

$$R—(CH_2)_n—O—CO—Cl \qquad (XXV)$$

wherein

R and n are as hereinbefore defined, with α-amino acid derivatives of general formula XXVI,

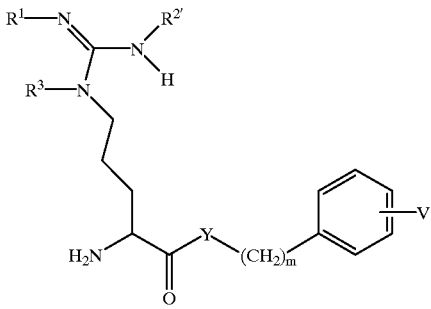

(XXVI)

wherein $R^1$, $R^3$, V, Y and m are as hereinbefore defined and $R^{2''}$ has the meanings given for $R^2$ hereinbefore or also denotes one of the protecting groups mentioned hereinbefore for protecting the side chain of arginine which are orthogonal to carbamates and, if necessary, subsequently cleaving protecting groups using the methods described hereinbefore.

The reaction is carried out at temperatures of between 0 and 150° C., preferably at temperatures of between 20 and 100° C., and optionally in the presence of anhydrous solvents, e.g. tetrahydrofuran, 1,4-dioxan, dimethylformamide, dimethylacetamide, N-methyl-2-pyrrolidone or 1,3-dimethyl-2-imidazolidinone or mixtures thereof, and in the presence of auxiliary bases. The auxiliary bases used may be alkali metal carbonates, e.g. sodium carbonate, potassium carbonate or caesium carbonate, alkali metal acetates, e.g. sodium or potassium acetate, but preferably tertiary amines, for example pyridine, 2,4,6-trimethylpyridine, quinoline, triethylamine, N-ethyl-diisopropylamine, N-ethyl-dicyclohexylamine, 1,4-diazabicyclo[2,2,2]octane or 1,8-diazabicyclo[5,4,0]-undec-7-ene.

The amino acid derivatives of general formula I according to the invention contain at least one chiral centre. If in addition the group R is prochiral or chiral, the compounds may occur in the form of two diastereomeric pairs of antipodes. The invention includes the individual isomers as well as the mixtures thereof.

The diastereomers are separated on the basis of their different physico-chemical properties, e.g. by fractional crystallisation from suitable solvents, by high pressure liquid or column chromatography using chiral or preferably achiral stationary phases.

The racemates of general formula I may be separated for example by HPLC on suitable chiral stationary phases (e.g. Chiral AGP, Chiralpak AD). Racemates which contain a basic function may also be separated by means of the diastereomeric, optically active salts which are formed on reacting with an optically active acid, for example (+)-or (−)-tartaric acid, (+) or (−)-diacetyltartaric acid, (+) or (−)-monomethyl tartrate or (+)-camphorsulphonic acid.

According to a conventional method of isomer separation the racemate of a compound of general formula I is reacted with one of the abovementioned optically active acids in equimolar amounts in a solvent and the crystalline, diastereomeric, optically active salts obtained are separated using their differences in solubility. This reaction may be carried out in any kind of solvent provided that it exhibits a sufficient difference in terms of the solubility of the salts. Preferably, methanol, ethanol or the mixtures thereof are used, for example in a ratio by volume of 50:50. Then each of the optically active salts is dissolved in water, neutralised with a base, such as sodium carbonate or potassium carbonate, sodium hydroxide solution or potassium hydroxide solution and the corresponding free compound is obtained in the (+) or (−) form.

Only the (R)-enantiomer or a mixture of two optically active, diastereomeric compounds of general formula I is obtained by carrying out the above-described syntheses with a reaction component containing the corresponding (R)-configured amino acid.

The starting materials of general formulae III, IV, VI, VII, VIII, IX, X, XI, XIII, XV, XVI, XIXa, XIXb, XIXc, XXIV, XXV required for synthesising the compounds of general formula I and the amino acids used are commercially obtainable or may be prepared by methods known from the literature. The acids II are obtained for example under the conditions of a Schotten-Baumann or Einhorn reaction from the corresponding α-amino acids and compounds of general formulae IV, XVI or XXV (cf. also: M. Bodanszky and A. Bodanszky, "The Practice of Peptide Synthesis", Springer Verlag 1984, P. 9 to 31).

Isocyanates of general formula XIV may readily be prepared from α-amino acid derivatives of general formula V or from the hydrochlorides thereof by reacting with phosgene, diphosgene or triphosgene in the presence of pyridine (cf. also: J. P. Nowick, N. A. Powell, T. M. Nguyen and G. Noronha, J. Org. Chem. 57, 7364–7366 [1992]).

The starting compounds of general formula V may in turn be obtained from amino acids suitably protected at the α-amino group as described hereinbefore and compounds of general formula III analogously to method a). The compounds required as starting materials, uronium salts of general formula XII, are most easily obtained by adding $R^{11}OH$ alcohols to the corresponding cyanamides, for example using potassium cyanide (cf. also: A. Donetti et al., Tetrah. Lett. 1969, 3327–3328; A. Donetti et al., J. Org. Chem. 37, 3352–3353 (1972); M. Okahara et al., Tetrah. Lett. 1981, 4105–4106) or sodium methoxide (cf. also: F. C. Schaefer et al., J. Org. Chem. 26, 412–418 (1961); R. M. Giuliano et al., J. Org. Chem. 51, 2304–2307 (1986); F. H. P. Hurd et al., J. Chem Soc. 1949, 1732–1738)) as catalysts, the thiuronium salts of general formula XII are obtained from corresponding thioureas by reaction with alkylating agents of type $R^{11}$—X, wherein X denotes, for example, the iodine atom or the groups $OSO_2CH_3$ or $OSO_2C_6H_4CH_3$ (p). The starting compounds of general formula XVII can easily be produced from precursors which carry, instead of the terminal group —$(CH_2)_o$—$Y^1$—H of general formula XVII, an end group —$(CH_2)_o$—$Y^1$—Pg characterised by readily cleavable protecting groups Pg, e.g. tert.butoxycarbonyl or phenylmethoxycarbonyl, or precursor groups, for example —$(CH_2)_{o-1}$-C≡N or —$(CH_2)_oNO_2$. The preparation of the starting compounds of general formula XVIII is described in WO 94/17035 and in German Patent Application P 44 25 545.4 or may be carried out by analogous methods. Processes for preparing the cyanoguanidines of general formula XXI required as starting compounds are also discussed in WO 94/17035. Finally, the starting compounds of general formula XXV may be obtained in the same way as the starting compounds of general formula V.

The compounds of general formula I obtained may be converted into their physiologically acceptable salts with inorganic or organic acids, particularly for pharmaceutical applications. Examples of acids for this purpose include hydrochloric acid, hydrobromic acid, phosphoric acid, nitric acid, sulphuric acid, methanesulphonic acid, p-toluenesulphonic acid, acetic acid, fumaric acid, succinic acid, lactic acid, mandelic acid, malic acid, citric acid, tartaric acid or maleic acid.

Moreover, the new compounds of formula I thus obtained, if they contain a carboxy group, may subsequently, if desired, be converted into the addition salts thereof with inorganic or organic bases, particularly, for pharmaceutical use, into the physiologically acceptable addition salts thereof. Suitable bases include for example sodium hydroxide, potassium hydroxide, ammonia, cyclohexylamine, dicyclohexylamine, ethanolamine, diethanolamine and triethanolamine.

The new compounds of general formula I and the physiologically acceptable salts thereof have NPY-antagonistic properties and exhibit good affinities in NPY-receptor binding studies. The compounds exhibit NPY-antagonistic properties both in vivo and in vitro in the pharmacological test systems described hereinafter.

To demonstrate the affinity of compounds of general formula I for human NPY-receptors and their antagonistic properties the following experiments were carried out:

A. Binding studies with SK—N—MC cells (expressing the human $Y_1$-receptor)

The cells are detached by a mixture of 0.02% EDTA in PBS and resuspended in 10 ml of incubation medium (MEM/25 mM Hepes+0,5% BSA, 50 mM PMSF, 0,1% bacitracin, 3,75 mM $CaCl_2$) per approx. 40 million cells. After 5 min centrifugation (150×g) the pellet is resuspended in the same volume and after another washing step resuspended in 10 ml of incubation medium, counted and diluted down to 1.25 million cells/ml. Then 200 ul of a suspension of 1.25 million cells/ml are incubated for 3 hours at ambient temperature with 25 ul of a 300 pM solution of $[^{125}I]$-Bolton-Hunter-NPY and increasing concentrations ($10^{-11}$ to $10^{-6}$ M) of the test substances, maintaining a total volume of 250 ul. The incubation is ended by centrifugation (10 min at 3000×g and 4° C.). After washing once with PBS the radioactivity of the pellet is measured in the gamma-counter. The radioactivity thus obtained represents the sum of specific and non-specific binding of $[^{125}I]$-Bolton-Hunter-NPY. The amount of non-specific binding is defined as the radioactivity which is bound in the presence of 1 uM NPY. The $IC_{50}$ values of the unlabelled test substances are determined graphically. They represent the concentration of the relevant test substance at which the specific binding of $[^{125}I]$-Bolton-Hunter-NPY to the NPY—$Y_1$ receptor is inhibited by 50%.

The compounds of general formula I have $IC_{50}$-values of <7,000 nM in the test described.

B. In vitro NPY-antagonism

Male rats (CHbb: THOM, 300 to 350 g) are given heparin (100 IU, i.v.) and the animals are then killed by a blow to the back of the neck. The abdomen is opened up along the centre of the body and the left kidney is removed, after the insertion of catheters in the renal artery, the renal vein and the ureter. The isolated kidney is immediately perfused with a modified Krebs-Ringer solution (4 ml/minute) of the following composition:

| | |
|---|---|
| NaCl | 118.0 mmol/l |
| $KH_2PO_4$ | 1.2 mmol/l |
| KCl | 4.8 mmol/l |
| $HgSO_4$ | 1.2 mmol/l |
| $CaCl_2$ | 2.5 mmol/l |
| $NaHCO_3$ | 25.0 mmol/l |
| Glucose | 6.5 mmol/l |

A mixture of 95% $O_2$/5% $CO_2$ is passed through the solution which is maintained at a temperature of 37° C. The perfusion pressure is measured continuously using a pressure recorder. After a 60-minute stabilising period the perfusion rate is adjusted so as to achieve a perfusion pressure of about 100 mm Hg. After another 30 minutes the experiment is started and NPY (1 mM) is administered as a bolus (0.1 ml) at 15 minute intervals until the pressure increase observed achieves a constant value. The compounds to be investigated are administered as a continuous infusion over a period of 5 minutes and then NPY is injected. After a 30-minute washing-out period the next-highest concentration of the test substance is investigated. For each test, 3 to 5 different concentrations of the relevant compound are tested. Concentration-activity-curves can be drawn by plotting the percentage inhibition of the NPY activity against the logarithm of the concentration (mol/l) of the compound.

The compounds of general formula I exhibit NPY-antagonistic properties in the in-vitro test model described, in a dosage range of between $10^{-8}$ and $10^{-5}$ M.

C. In-vivo-NPY antagonism

Male rats with normal blood pressure (Chbb:THOM, 300 to 350 g) are anaesthetised with sodium hexobarbital (150 mg/kg, i.p.). After intubation of the trachea the animals are pithed by the insertion of a blunt needle through the eye into the central canal of the spinal cord. The animals are ventilated with oxygen-enriched ambient air using a ventilator pump (20 strokes per minute). A cannula is inserted into the left carotid artery and the arterial blood pressure is measured using a pressure transducer (Braun Melsungen Combitrans) attached to a recording instrument. For injection purposes a catheter is inserted in the left jugular vein, through which heparin is administered (200 IU/kg, i.v.). After the blood pressure has been stabilised the animals are given 2 bolus injections of NPY (10 mg/kg, i.v.) at an interval of 15 minutes. The mean increase in diastolic blood pressure serves as a reference value (=100%). The test substances are injected in increasing doses (4 to 6 doses) at 15 minute intervals. One minute after the administration of the test substance NPY is given.

The antagonistic activity of the test substances is determined by plotting the percentage inhibition of the NPY-induced blood pressure effects against the logarithm of the concentration of active substance.

The compounds of general formula I display NPY-antagonistic properties in the in vivo test model after intravenous administration in a dosage range of 0.001 to 10 mg/kg.

In view of their pharmacological properties the compounds of general formula I and the physiologically acceptable salts thereof are thus suitable for treating cardiovascular diseases, e.g. for treating arterial hypertension, hypertensive crisis, stress-induced high blood pressure triggered, for example, by the environment, by physical exertion or cold irritation, chronic cardiac insufficiency, coronary heart disease, such as angina pectoris, myocardial infarct and syndrome X, and also for treating subarachnoid bleeding, vascular-hypertrophic changes, e.g. restenosis after coronary angioplasty (PCTA), cerebral and coronary vasospasms, e.g. stroke, chronic kidney failure, hyperthyroidism, obesity and diabetes, epileptic diseases and for diagnosing, evaluating the prognosis of and treating tumoral diseases, for example pheochromocytomas, neuro(fibro)blastomas, ganglioneuromas, ganglioneuroblastomas, rhabdomyosarcomas, malignant ectomesenchymomas, anaplastic astrocytomas or haemangioblastomas.

The dosage required to achieve the corresponding effect is appropriately, for intravenous administration, 0.01 to 3 mg/kg of body weight, preferably 0.1 to 1 mg/kg of body weight, and for oral administration 0.1 to 10 mg/kg of body weight, preferably 1 to 10 mg/kg of body weight, 1 to 3× a day.

For this purpose the compounds of general formula I prepared according to the invention, optionally in conjunction with other active substances, such as e.g. hypotensive agents, ACE-inhibitors, diuretics and/or calcium antagonists, together with one or more inert conventional carriers and/or diluents, e.g. with corn starch, lactose, glucose, microcrystalline cellulose, magnesium stearate, polyvinyl pyrrolidone, citric acid, tartaric acid, water, water/ethanol, water/glycerol, water/sorbitol, water/polyethyleneglycol, propyleneglycol, cetylstearylalcohol, carboxy-methylcellulose or fatty substances such as hard fat or suitable mixtures thereof, may be incorporated in conventional galenic preparations such as plain or coated tablets, capsules, powders, suspensions or suppositories.

Additional active substances for the abovementioned combinations might thus include, for example, bendroflumethiazide, chlorothiazide, hydrochlorothiazide, spironolactone, benzthiazide, cyclothiazide, ethacrinic acid, furosemide, metoprolol, prazosine, atenolol, propranolol, (di)hydralazine-hydrochloride, diltiazem, felodipine, nicardipine, nifedipine, nisoldipine, nitrendipine, captopril, enalapril, lisinopril, cilazapril, quinapril, fosinopril and ramipril. The dosage for these active substances is conveniently from ⅕ of the minimum dose normally recommended up to ¼ of the normally recommended dose, i.e. for example 15 to 200 mg of hydrochlorothiazide, 125 to 2000 mg of chlorothiazide, 15 to 200 mg of ethacrinic acid, 5 to 80 mg of furosemide, 20 to 480 mg of propranolol, 5 to 60 mg of felodipine, 5 to 60 mg of nifedipine or 5 to 60 mg of nitrendipine.

The invention further relates to the use of the compounds of general formula I as valuable adjuvants for the production and purification (by affinity chromatography) of antibodies and, after suitable radiolabelling, for example by direct labelling with $^{125}I$ or $^{131}I$ or by tritiation of suitable precursors, for example by replacing halogen atoms with tritium, in RIA and ELISA assays and as a diagnostic or analytical aid in neutrotransmitter research.

The Examples which follow are intended to illustrate the invention:

Preliminary remarks:

"Mp." denotes "melting point", "D." denotes "decomposition". For all the compounds there are satisfactory elemental analyses, IR, UV, $^1$H-NMR and generally also mass spectra. Unless otherwise stated, $R_f$ values were determined using ready-made silica gel TLC plates 60 $F_{254}$, layer thickness 0.25 mm (E. Merck, Darmstadt, serial no. 1.05729) and an eluant consisting of ethyl acetate/methanol=1/1 (v/v) (variant A) or n-butanol/glacial acetic acid/water=4/1/1 (v/v/v) (variant B), without chamber saturation. If the configuration is not specified in detail it is unclear whether it is the (R)-enantiomer or whether partial or even total racemisation has occurred.

EXAMPLE 1

(R)-N$^2$-(diphenylacetyl)-N$^7$-(methylaminocarbonyl)-N-[[4-(methylaminocarbonyloxy)phenyl]methyl]-argininamide-acetate a) (R)-N$^2$-(tert.-butoxycarbonyl)-N$^7$-(methylaminocarbonyl)-N-[[4-(methylaminocarbonyloxy)phenyl]methyl]-N$^{7'}$-nitro-argininamide To a solution of 4.2 g (0.01 mol) of (R)-N$^2$-(tert.-butoxycarbonyl)-N-[(4-hydroxyphenyl)methyl]-N$^7$-nitro-argininamide in a mixture of 100 ml of anhydrous tetrahydrofuran and 20 ml of dimethylformamide were added successively 3.5 g (0.0346 mol) of triethylamine and 1.7 g (0.0298 mol) of methylisocyanate and the mixture was then heated to 75° C. for 3 hours with stirring. The solvent was distilled off in vacuo, the oily residue remaining was purified by column chromatography on silica gel (for analysis, Baker, 30–60 μm) using first ethyl acetate, then ethyl acetate/methanol/cyclohexane/conc. aqueous ammonia=85/5/10/1 (v/v/v/v) as eluant. After the relevant fractions had been worked up in the usual way 0.9 g (17% of theory) of colourless crystals were obtained, mp. 177–178° C. IR (KBr): 1710.8 (urethane/urea-CO) cm$^{-1}$ ESI-MS: $(M+H)^+ = 539$
$(M+Na)^+ = 561$
$(M+NH_4)^+ = 556$ b) (R)-N$^2$-(diphenylacetyl)-N$^7$-(methylaminocarbonyl)-N-[[4-(methylaminocarbonyloxy)phenyl]methyl]-N$^{7'}$-nitro-argininamide The solution of 0.9 g (1.672 mmol) of (R)-N$^2$-(tert.-butoxycarbonyl)-N$^7$-(methylaminocarbonyl)-N-[[4-(methylaminocarbonyloxy)phenyl]methyl]-N$^{7'}$-nitro-argininamide in 10 ml of trifluoroacetic acid was stirred for 30 minutes at ambient temperature, then evaporated down in vacuo. The residue remaining was taken up in 10 ml of dimethylformamide, mixed successively with 2 ml of diisopropylethylamine and 0.4 g (1.72 mmol) of diphenylacetylchloride and stirred for 2 hours at ambient temperature. The solvent was eliminated in vacuo, the oily residue remaining was stirred into water, suction filtered and recrystallised from hot acetonitrile. 0.7 g (66% of theory) of slightly yellowish crystals were obtained, mp. 178° C. (D).

IR (KBr): 1712.7 (urethane/urea-CO), 1637.5 (amide-CO) cm$^{-1}$ c) (R)-N$^2$-(diphenylacetyl)-N$^7$-(methylaminocarbonyl)-N-[[4-(methylaminocarbonyloxy)phenyl]methyl]-argininamide acetate A solution of 0.7 g (1.107 mmol) of (R)-N$^2$-(diphenylacetyl)-N$^7$-(methylaminocarbonyl)-N-[[4-(methylaminocarbonyloxy)-phenyl]methyl]-N$^{7'}$-nitro-argininamide in 70 ml of 80% aqueous acetic acid was hydrogenated in the presence of 0.1 g of palladium black at 40° C. and 5 bars of hydrogen pressure until the hydrogen uptake ceased. The catalyst was filtered off, the filtrate evaporated down in vacuo and the residue triturated with acetone/diethylether 5/1 (v/v). The residue was suction fltered and after drying 240 mg (40% of theory) of colourless crystals were obtained, mp. 122–124° C. and $R_f$ 0.62 (variant B).

IR (KBr): 1712.7 (urethane-CO), 1637.5 broad (amide/urea-CO) cm$^{-1}$

ESI-MS: (M + H)$^+$ = 588
(M + Na)$^+$ = 610
(M + K)$^+$ = 626

EXAMPLE 2

(R)-N-[[4-(aminocarbonylaminomethyl)phenyl]methyl]-N$^7$-(butylaminocarbonyl)-N$^2$-(diphenylacetyl)-argininamide-acetate a) (R)-N-[[4-(aminocarbonylaminomethyl)phenyl]methyl]-N$^7$-(butylaminocarbonyl)-N$^2$-(diphenylacetyl)-N$^{7'}$-nitro-argininamide Prepared analogously to Example 1a), but using acetonitrile/dimethylformamide=2/1 (v/v) as solvent, from (R)-N-[[4-(aminocarbonylaminomethyl)phenyl]methyl]-N$^2$-(diphenylacetyl)-N$^7$-nitro-argininamide and n-butylisocyanate in a yield of 50% of theory. Pale yellow crystals (acetonitrile/diethylether=1/1 (v/v)).

ESI-MS: (M + H)$^+$ = 674
(M + Na)$^+$ = 696
(M + NH$_4$)$^+$ = 691 b) (R)-N-[[4-(aminocarbonylaminomethyl)phenyl]methyl]-N$^7$-(butylaminocarbonyl)-N$^2$-(diphenylacetyl)-argininamide-acetate Prepared analogously to Example 1c) by catalytic hydrogenation of (R)-N-[[4-(aminocarbonylaminomethyl)phenyl]methyl]-N$^7$-(butylaminocarbonyl)-N$^2$-(diphenylacetyl)-N$^{7'}$-nitro-argininamide in the presence of palladium black and 80% aqueous acetic acid in a yield of 18% of theory. Colourless crystals, mp. 183° C. and R$_f$ 0.62 (variant B).

IR (KBr): 1641.3 (amide/urea-CO) cm$^{-1}$

ESI-MS: (M + H)$^+$ = 629
(M + Na)$^+$ = 651
(M + K)$^+$ = 667

EXAMPLE 3

(R)-N$^2$-(diphenylacetyl)-N-[(4-hydroxyphenyl)methyl]-N$^7$-(methylaminocarbonyl)-argininamide-acetate a) (R)-N$^2$-(diphenylacetyl)-N-[(4-hydroxyphenyl)methyl]-N$^7$-(methylaminocarbonyl)-N$^{7'}$-nitro-argininamide The solution of 0.95 g (1.502 mmol) of (R)-N$^2$-(diphenylacetyl)-N$^7$-(methylaminocarbonyl)-N-[[4-(methylaminocarbonyloxy)phenyl]-methyl]-N$^{7'}$-nitro-argininamide in 100 ml of methanol was mixed dropwise with 2.25 ml of 2N sodium hydroxide solution and stirred for 30 minutes at ambient temperature. The solvent was eliminated in vacuo, the residue dissolved in 150 ml of water, extracted once with 100 ml of diethylether and then acidified by careful addition of 12% hydrochloric acid. The colourless precipitate was suction filtered, washed thoroughly with water and dried at 40° C. in the circulating air drier. 470 mg (54% of theory) of crystals were obtained, mp. 185° C.

b) (R)-N$^2$-(diphenylacetyl)-N-[(4-hydroxyphenyl)methyl]-N$^7$-(methylaminocarbonyl)-argininamide-acetate Prepared analogously to Example 1c) by catalytic hydrogenation of (R)-N$^2$-(diphenylacetyl)-N-[(4-hydroxyphenyl)methyl]-N$^7$-(methylaminocarbonyl)-N$^{7'}$-nitro-argininamide in the presence of palladium black and 80% aqueous acetic acid in a yield of 72% of theory. Colourless crystals, mp. 191–193° C. (Z.) and R$_f$ 0.65 (variant B).

IR (KBr): 1681.8 (guanidine), 1643.3 (amide-CO) cm$^{-1}$

ESI-MS: (M + H)$^+$ = 531
(M + Na)$^+$ = 553
(M + K)$^+$ = 569

EXAMPLE 4

(R)-N$^7$-(butylaminocarbonyl)-N$^2$-(diphenylacetyl)-N-[(4-hydroxyphenyl)methyl]-argininamide-acetate a) (R)-N$^7$-(butylaminocarbonyl)-N-[[4-(butylaminocarbonyloxy)phenyl]methyl]-N$^2$-(diphenylacetyl)-N$^{7'}$-nitro-argininamide Prepared analogously to Example 1a), but using tetrahydrofuran as solvent and 4-(dimethylamino)-pyridine as the base, from (R)-N$^2$-(diphenylacetyl)-N-[(4-hydroxyphenyl)methyl]-N$^7$-nitro-argininamide and butylisocyanate. The product was used without further purification in the following step.

b) (R)-N$^7$-(butylaminocarbonyl)-N$^2$-(diphenylacetyl)-N-[(4-hydroxyphenyl)methyl]-N$^{7'}$-nitro-argininamide Prepared analogously to Example 3a) from (R)-N$^7$-(butylaminocarbonyl)-N-[[4-(butylaminocarbonyloxy)phenyl]-methyl]-N$^2$-(diphenylacetyl)-N$^{7'}$-nitro-argininamide by saponification with aqueous-methanolic sodium hydroxide solution in a total yield over the two steps a) and b) of 28% of theory. Colourless crystals, mp. 190° C. (acetonitrile).

IR (KBr): 1712.7 (urea-CO), 1633.3 (amide-CO) cm$^{-1}$

ESI-MS: (M + H)$^+$ = 618
(M + Na)$^+$ = 640
(M + K)$^+$ = 656 c) (R)-N$^7$-(butylaminocarbonyl)-N$^2$-(diphenylacetyl)-N-[(4-hydroxyphenyl)methyl]-argininamide-acetate Prepared analogously to Example 1c), but using 80% acetic acid/methanol 5/1 (v/v) as solvent, by catalytic hydrogenation of (R)-N$^7$-(butylaminocarbonyl)-N$^2$-(diphenylacetyl)-N-[(4-hydroxyphenyl)methyl]-N$^{7'}$-nitro-argininamide in the presence of palladium black in a yield of 74% of theory. Colourless crystals, mp. 178–180° C. and R$_f$ 0.75 (variant B).

IR (KBr): 1701.1 (urea-CO), 1679.9 (guanidine), 1641.3 (amide-CO) cm$^{-1}$

ESI-MS: (M + H)$^+$ = 573
(M + Na)$^+$ = 595

EXAMPLE 5

(R)-N-[[4-(aminocarbonylaminomethyl)phenyl]
methyl]-N$^2$-(diphenylacetyl)-N$^7$-
(methylaminocarbonyl)-argininamide-acetate a) (R)-N-[[4-(aminocarbonylaminomethyl)phenyl]methyl]-N$^2$-(diphenylacetyl)-N$^7$-(methylaminocarbonyl)-N$^{7'}$-nitro-argininamide Prepared analogously to Example 1a), but using diisopropylethylamine as catalyst and acetonitrile as solvent, from (R)-N-[[4-aminocarbonylaminomethyl)phenyl]-methyl]-N$^2$-(diphenylacetyl)-N$^7$-nitro-argininamide and methylisocyanate in a yield of 89% of theory. Colourless crystals, mp. 183° C. (acetonitrile).

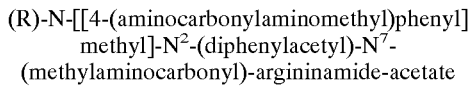

ESI-MS: $(M + H)^+ = 632$
$(M + Na)^+ = 654$
$(M - H)^- = 630$ b) (R)-N-[[4-(aminocarbonylaminomethyl)phenyl]methyl]-N$^2$-(diphenylacetyl)-N$^7$-(methylaminocarbonyl)-argininamide-acetate Prepared analogously to Example 1c) from (R)-N-[[4-(aminocarbonyl-aminomethyl)phenyl]methyl]-N$^2$-(diphenylacetyl)-N$^7$-(methylaminocarbonyl)-N$^{7'}$-nitro-argininamide by catalytic hydrogenation in the presence of palladium black in a yield of 69% of theory. Colourless crystals, mp. 182–184° C. and R$_f$ 0.55 (variant B).

IR (KBr): 1652.9 broad (amide/urea-CO) cm$^{-1}$

ESI-MS: $(M + H)^+ = 587$
$(M + Na)^+ = 609$
$(M + K)^+ = 625$

EXAMPLE 6

(R)-N-[[4-(aminocarbonylaminomethyl)phenyl]
methyl]-N$^2$-(diphenylacetyl)-N$^7$-
(ethylaminocarbonyl)-argininamide-acetate a) (R)-N-[[4-(aminocarbonylaminomethyl)phenyl]methyl]-N$^2$-(diphenylacetyl)-N$^7$-(ethylaminocarbonyl)-N$^{7'}$-nitro-argininamide Prepared analogously to Example 5a), from (R)-N-[[4-aminocarbonyl-aminomethyl)phenyl]methyl]-N$^2$-(diphenylacetyl)-N$^7$-nitro-argininamide and methylisocyanate in a yield of 86% of theory. Colourless crystals, mp. 171° C. (acetonitrile).

ESI-MS: $(M + H)^+ = 646$
$(M + Na)^+ = 668$
$(M - H)^- = 644$ b) (R)-N-[[4-(aminocarbonylaminomethyl)phenyl]methyl]-N$^2$-(diphenylacetyl)-N$^7$-(ethylaminocarbonyl)-argininamide-acetate Prepared analogously to Example 1c) from (R)-N-[[4-(aminocarbonyl-aminomethyl)phenyl]methyl]-N$^2$-(diphenylacetyl)-N$^7$-(ethyl-aminocarbonyl)-N$^{7'}$-nitro-argininamide by catalytic hydrogenation in the presence of palladium black in a yield of 71% of theory. Colourless crystals, mp. 176–177° C. and R$_f$ 0.60 (variant B).

IR (KBr): 1639.4 broad (amide/urea-CO, guanidine) cm$^{-1}$

ESI-MS: $(M + H)^+ = 601$
$(M + Na)^+ = 623$

EXAMPLE 7

(R)-N$^2$-(diphenylacetyl)-N$^7$-(ethylaminocarbonyl)-
N-[(4-hydroxyphenyl)methyl]-argininamide-acetate a) (R)-N$^2$-(diphenylacetyl)-N$^7$-(ethylaminocarbonyl)-N-[[4-(ethylaminocarbonyloxy)phenyl]methyl]-N$^{7'}$-nitro-argininamide Prepared analogously to Example 1a), but using acetonitrile as solvent and 4-(dimethylamino)-pyridine as base, from (R)-N$^2$-(diphenylacetyl)-N-[(4-hydroxyphenyl)-methyl]-N$^7$-nitro-argininamide and ethylisocyanate in a yield of 81% of theory. Colourless crystals, mp. 175° C. (D.) (acetonitrile).

IR (KBr): 1708.8 (urethane/urea-CO), 1637.5 (amide-CO) cm$^{-1}$

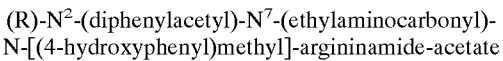

ESI-MS: $(M + H)^+ = 661$
$(M + Na)^+ = 683$
$(M + K)^+ = 699$ b) (R)-N$^2$-(diphenylacetyl) -N$^7$-(ethylaminocarbonyl)-N-[(4-hydroxyphenyl)methyl]-N$^{7'}$-nitro-argininamide Prepared analogously to Example 3a) from (R)-N$^2$-(diphenylacetyl)-N$^7$-(ethylaminocarbonyl)-N-[[4-(ethylaminocarbonyloxy)-phenyl]methyl]-N$^{7'}$-nitro-argininamide by saponification with aqueous-methanolic sodium hydroxide solution in a yield of 88% of theory. Colourless crystals, mp. 177° C.

c) (R)-N$^2$-(diphenylacetyl)-N$^7$-(ethylaminocarbonyl)-N-[(4-hydroxyphenyl)methyl]-argininamide-acetate Prepared analogously to Example 1c) by catalytic hydrogenation of (R)-N$^2$-(diphenylacetyl)-N$^7$-(ethylaminocarbonyl)-N-[(4-hydroxyphenyl)methyl]-N$^{7'}$-nitro-argininamide in the presence of palladium black and 80% aqueous acetic acid in a yield of 76% of theory. Colourless crystals, mp. 180° C. (D.) and R$_f$ 0.68 (variant B).

IR (KBr): 1679.9 (guanidine), 1643.3 (amide-CO) cm$^{-1}$

ESI-MS: $(M + H)^+ = 545$
$(M + Na)^+ = 567$

EXAMPLE 8

(R)-N-[[4-(aminocarbonylmethyl)phenyl]methyl]-
N$^2$-(diphenylacetyl)-N$^7$-[(methylethyl)
aminocarbonyl]-argininamide-acetate a) (R)-N-[[4-(aminocarbonylmethyl)phenyl]methyl]-N$^2$-(diphenylacetyl)-N$^7$-[(methylethyl)aminocarbonyl]-N$^{7'}$-nitro-argininamide Prepared analogously to Example 2a), but using diisopropylethylamine as base, from (R)-N-[[4-(aminocarbonylmethyl)phenyl]methyl]-N$^2$-(diphenylacetyl)-N$^7$ -nitro-argininamide and isopropylisocyanate in a yield of 64% of theory. Colourless crystalline substance.

IR (KBr) : 1662.5, 1637.5 (urea-/amide-CO) cm$^{-1}$

ESI-MS: (M + H)$^+$ = 645
(M + Na)$^+$ = 667 b) (R)-N-[[4-(aminocarbonylmethyl)phenyl]methyl]-N$^2$-(dipheylacetyl)-N$^7$-[(methylethyl)aminocarbonyl]-argininamide-acetate Prepared analogously to Example 1c) by catalytic hydrogenation of (R)-N-[[4-(aminocarbonylmethyl)phenyl]methyl]-N$^2$-(dipheylacetyl)-N$^7$-[(methylethyl)aminocarbonyl]-N$^{7'}$-nitro-argininamide in the presence of palladium black and 80% aqueous acetic acid in a yield of 26% of theory. Colourless amorphous substance, R$_f$ 0.57 (variant B).

IR (KBr): 1656.8, 1637.5 (urea-/amide-CO) cm$^{-1}$

ESI-MS: (M + H)$^+$ = 600
(M + Na)$^+$ = 622

EXAMPLE 9

(R)-N$^2$-(diphenylacetyl)-N-[(4-hydroxyphenyl)methyl]-N$^7$-[(phenylmethyl)aminocarbonyl]-argininamide-acetate a) (R)-N$^2$-(diphenylacetyl)-N$^7$-nitro-N$^{7'}$-[(phenylmethyl)-aminocarbonyl]-N-[[4-[(phenylmethyl)aminocarbonyloxy])-phenyl]methyl]-argininamide Prepared analogously to Example 7a) from (R)-N$^2$-(diphenylacetyl)-N-[(4-hydroxyphenyl)methyl]-N$^7$-nitro-argininamide and benzylisocyanate in a yield of 95% of theory. The product was used in the next step without further purification.

b) (R)-N$^2$-(diphenylacetyl)-N-[(4-hydroxyphenyl)methyl]-N$^7$-nitro-N$^{7'}$-[(phenylmethyl)aminocarbonyl]-argininamide Prepared analogously to Example 3a) from (R)-N$^2$-(diphenylacetyl)-N$^7$-nitro-N$^{7'}$-[(phenylmethyl)aminocarbonyl]-N-[[4-[(phenyl-methyl)aminocarbonyloxy])phenyl]methyl]-argininamide by saponification with aqueous-methanolic sodium hydroxide solution in a yield of 17% of theory. Colourless amorphous substance, which was used in the following step without further purification.

c) (R)-N$^2$-(diphenylacetyl)-N-[(4-hydroxyphenyl)methyl]-N$^7$-[(phenylmethyl)aminocarbonyl]-argininamide-acetate Prepared analogously to Example 1c) by catalytic hydrogenation of (R)-N$^2$-(diphenylacetyl)-N-[(4-hydroxyphenyl)methyl]-N$^7$-nitro-N$^{7'}$-[(phenylmethyl)aminocarbonyl]-argininamide in the presence of palladium black and 80% aqueous acetic acid in a yield of 25% of theory. Colourless amorphous substance, R$_f$ 0.75 (variant B).

IR (KBr): 1681.8 (guanidine; urea-CO), 1641.3 (amide-CO) cm$^{-1}$

ESI-MS: (M + H)$^+$ = 607
(M + Na)$^+$ = 629
(M + K)$^+$ = 645

EXAMPLE 10

(R)-N$^2$-(diphenylacetyl)-N-[(4-hydroxyphenyl)methyl]-N$^7$-(methoxycarbonyl)-argininamide-acetate A mixture of 1.0 g (2.319 mmol) of (R)-N$^2$-(diphenylacetyl)-N-[(4-hydroxyphenyl)methyl]-ornithinamide, 0.53 g (4.013 mmol) of O-methyl-N-(methoxycarbonyl)-isourea and 1 ml of glacial acetic acid was heated for 2 hours to 70° C. After the addition of a further 0.5 g (3.786 mmol) of O-methyl-N-(methoxycarbonyl)-isourea the mixture was kept for a further 2 hours at a reaction temperature of 70° C., the solvent was eliminated in vacua, the residue was taken up in a little acetonitrile, stirred for 30 minutes at ambient temperature and the precipitate formed was suction filtered. The amorphous product obtained was dried overnight in the air and then purified by column chromatography on silica gel (Baker, 30–60 μm) using dichloromethane/methanol/cyclohexane/conc. aqueous ammonia=70/15/15/2 (v/v/v/v) as eluant. Working up the suitable eluates yielded 300 mg (22% of theory) of a colourless, amorphous substance, Rf value 0.64 (variant B).

IR (KBr): 1737.8 (urethane-CO), 1645.2 (amide-CO) cm$^{-1}$

ESI-MS: (M + H)$^+$ = 532
(M + Na)$^+$ = 554
(M + K)$^+$ = 570

EXAMPLE 11

(R,S)-N$^2$-(diphenylacetyl)-N-[(4-methoxyphenyl)methyl]-N$^7$-(methylaminocarbonyl)-argininamide Prepared analogously to Example 10 from (R,S)-N$^2$-(diphenylacetyl)-N-[(4-methoxyphenyl)methyl]-ornithinamide and O-methyl-N-(methylaminocarbonyl)-isourea in a yield of 7% of theory. Colourless, amorphous substance, Rf 0.64 (variant B).

IR (KBr): 1649.0 broad (urea/amide-CO) cm–1

ESI-MS: (M + H)$^+$ = 545
(M + Na)$^+$ = 567

EXAMPLE 12

(R)-N-[[4-(aminocarbonylmethyl)phenyl]methyl]-N$^2$-(diphenylacetyl)-N$^7$-(methylaminocarbonyl)-argininamide a) (R)-N-((4-(aminocarbonylmethyl)phenyl]methyl]-N$^2$-(diphenylacetyl)-N$^7$-(methylaminocarbonyl)-N$^{7'}$-nitro-argininamide Prepared analogously to Example 8a) from (R)-N-[[4-(aminocarbonyl-methyl)phenyl]methyl]-N$^2$-(diphenylacetyl)-N$^7$-nitro-argininamide and methylisocyanate in a yield of 78% of theory. Colourless crystals.

IR (KBr): 1706.9 (urea-CO), 1664.5, 1629.8 (amide-CO) cm$^{-1}$

ESI-MS: (M + H)$^+$ = 617
(M + Na)$^+$ = 639
(M + NH$_4$)$^+$ = 634 b) (R)-N-[[4-(aminocarbonylmethyl)phenyl]methyl]-N$^2$-(diphenylacetyl)-N$^7$-(methylaminocarbonyl)-argininamide Prepared analogously to Example 1c) by catalytic hydrogenation of (R)-N-[[4-(aminocarbonylmethyl)phenyl]methyl]-N$^2$-(diphenylacetyl)-N$^7$-(methylaminocarbonyl)-

$N^{7'}$-nitro-argininamide in the presence of palladium black and 80% aqueous acetic acid in a yield of 8% of theory. Colourless amorphous substance, Rf 0.55 (variant B).

IR (KBr): 1652.9, 1640 (broad, amide/urea-CO) cm$^{-1}$

ESI-MS: $(M + H)^+$ = 572
$(M + Na)^+$ = 594

EXAMPLE 13

(R)-N-[[4-(aminocarbonylaminomethyl)phenyl]methyl]-$N^2$-(diphenylacetyl)-$N^7$-[(phenylmethyl)aminocarbonyl]-argininamide-acetate a) (R)-N-[[4-(aminocarbonylaminomethyl)phenyl]methyl]-$N^2$-(diphenylacetyl)-$N^7$-[(phenylmethyl)aminocarbonyl]-$N^{7'}$-nitro-argininamide Prepared analogously to Example Ba) from (R)-N-[[4-(aminocarbonyl-aminomethyl)phenyl]methyl]-$N^2$-(diphenylacetyl)-$N^7$-nitro-argininamide and benzylisocyanate in a yield of 35% of theory. Colourless crystals, mp. 175° C. (acetonitrile).

IR (KBr): 1705.0 (urea-CO), 1643.3 (urea/amide-CO) cm$^{-1}$

ESI-MS: $(M - H)^-$ = 706
$(M + Na)^+$ = 730 b) (R)-N-[[4-(aminocarbonylaminomethyl)phenyl]methyl]-$N^2$-(diphenylacetyl)-$N^7$-[(phenylmethyl)aminocarbonyl]-argininamide-acetate Prepared analogously to Example 1c) by catalytic hydrogenation of (R)-N-[[4-(aminocarbonylaminomethyl)phenyl]methyl]-$N^2$-(diphenylacetyl)-$N^7$-[(phenylmethyl)aminocarbonyl]-$N^{7'}$-nitro-argininamide in the presence of palladium black and 80% aqueous acetic acid in a yield of 55% of theory. Colourless crystals, mp. 134–136° C. and $R_f$ 0.75 (variant B).

IR (KBr): 1652.9 (urea/amide-CO) cm$^{-1}$

ESI-MS: $(M + H)^+$ = 663
$(M + Na)^+$ = 685

EXAMPLE 14

(R)-$N^7$-(aminocarbonyl)-$N^2$-(diphenylacetyl)-N-[(4-hydroxyphenyl)methyl]-$N^{7'}$-(phenylmethyl)-argininamide-trifluoracetate a) (R)-$N^5$-[(Cyanoimino)phenoxymethyl]-$N^2$-(diphenylacetyl)-N-[(4-hydroxyphenyl)methyl]-ornithinamide The mixture of 5.3 g (12.3 mmol) of (R)-$N^2$-(diphenylacetyl)-N-[(4-hydroxyphenyl)methyl]-ornithinamide, 3.0 g (12.6 mmol) of diphenyl cyanocarbimidate and 250 ml of 2-propanol was stirred at ambient temperature for 2 hours. The solvent was distilled off in vacuo, the residue divided between ethyl acetate and water, the ethyl acetate phase was dried over sodium sulphate and again evaporated down. After recrystallisation from ethyl acetate 6.3 g (89% of theory) of colourless crystals were obtained, mp. 110–112° C.

b) (R)-$N^7$-Cyano-$N^2$-(diphenylacetyl)-N-[(4-hydroxyphenyl)-methyl]-$N^{7'}$-(phenylmethyl)-argininamide The mixture of 1.0 g (1.738 mmol) of (R)-$N^5$-[(cyanoimino)phenoxymethyl]-$N^2$-(diphenylacetyl)-N-[(4-hydroxyphenyl)methyl]-ornithinamide, 0.2 g (1.87 mmol) of benzylamine and 20 ml of 2-propanol was refluxed for 5 days. The residue remaining after elimination of the solvent was purified by column chromatography on silica gel (Baker, 30–60 μm) using first cyclohexane/ethyl acetate=1/1 (v/v), then ethyl acetate. 0.5 g (49% of theory) of a colourless, non-crystallising substance were obtained.

IR (KBr): 2165.9 (C≡N), 1652.9 (amide-CO) cm$^{-1}$ c) (R)-$N^7$-(aminocarbonyl)-$N^2$-(diphenylacetyl)-N-[(4-hydroxyphenyl)methyl]-$N^{7'}$-(phenylmethyl)-argininamide-trifluoroacetate The solution of 0.5 g (0.85 mmol) of (R)-$N^7$-cyano-$N^2$-(diphenyl-acetyl)-N-[(4-hydroxyphenyl)methyl]-$N^{7'}$-(phenylmethyl)-argininamide in 30 ml of tetrahydrofuran was mixed with 10 ml of trifluoroacetic acid and 5 ml of water and stirred for 1 hour at a reaction temperature of 40° C. The solvent was eliminated in vacuo, the oily residue remaining was purified by column chromatography on silica gel (Baker, 30–60 μm) using ethyl acetate as eluant. After the evaporation of the relevant fractions 0.5 g (97% of theory) of a colourless, amorphous substance was obtained, Rf 0.66 (variant B).

IR (KBr): 1728.1 (trifluoroacetate), 1649.0 (urea/amide-CO) cm$^{-1}$

ESI-MS: $(M + H)^+$ = 607
$(M + Na)^+$ = 629

EXAMPLE 15

(R)-$N^7$-(aminocarbonyl)-$N^2$-(diphenylacetyl)-N-[(4-hydroxyphenyl)methyl]-argininamide a) (R)-$N^7$-Cyano-$N^2$-(diphenylacetyl)-N-[(4-hydroxyphenyl)-methyl]-argininamide Prepared analogously to Example 14b), but carrying out the reaction in a steel autoclave, from (R)-$N^5$-[(cyanoimino)phenoxymethyl]-$N^2$-(diphenylacetyl)-N-[(4-hydroxyphenyl)-methyl]-ornithinamide and ammonia in a quantitative yield. The product was used without further purification in the following step.

b) (R)-$N^7$-(aminocarbonyl)-$N^2$-(diphenylacetyl)-N-[(4-hydroxyphenyl)methyl]-argininamide Prepared analogously to Example 14c) from (R)-$N^7$-cyano-$N^2$-(diphenyl-acetyl)-N-[(4-hydroxyphenyl)methyl]-argininamide by hydration in the presence of trifluoroacetic acid in a yield of 33% of theory. Colourless crystals, mp. 136–138° C. (acetonitrile) and $R_f$ 0.64 (variant B).

IR (KBr): 1639.4 (broad, urea/amide-CO) cm$^{-1}$

ESI-MS: $(M + H)^+$ = 517
$(M + Na)^+$ = 539
$(M + K)^+$ = 555

EXAMPLE 16

(R)-N⁷-(aminocarbonyl)-N²-(diphenylacetyl)-N-[(4-hydroxyphenyl)methyl]-N⁷'-methyl-argininamide a) (R)-N⁷-Cyano-N²-(diphenylacetyl)-N-[(4-hydroxyphenyl)methyl]-N⁷'-methyl-argininamide Prepared analogously to Example 15a) from (R)-N⁵-[(cyanoimino)-phenoxymethyl]-N²-(diphenylacetyl)-N-[(4-hydroxyphenyl)-methyl]ornithinamide and methylamine in a quantitative yield. The product was used in the following step without further purification.

IR (KBr): 2167.9 (C=N—C≡N), 1652.9 (amide-CO) cm⁻¹ b) (R)-N⁷-(aminocarbonyl)-N²-(diphenylacetyl)-N-[(4-hydroxyphenyl)methyl]-N⁷'-methyl-argininamide Prepared analogously to Example 14c) from (R)-N⁷-cyano-N²-(diphenyl-acetyl)-N-[(4-hydroxyphenyl)methyl]-N⁷'-methyl-argininamide by hydration in the presence of trifluoroacetic acid in a yield of 38% of theory. Colourless crystals, mp. 142° C. (acetonitrile) and R$_f$ 0.53 (variant B).

IR (KBr): 1639.4 (urea/amide-CO) cm⁻¹

ESI-MS: (M + H)⁺ = 531
(M + Na)⁺ = 553

EXAMPLE 17

(R)-N⁷-(butoxycarbonyl)-N²-(diphenylacetyl)-N-[(4-hydroxyphenyl)methyl]-argininamide Prepared analogously to Example 10 from (R)-N²-(diphenylacetyl)-N-[(4-hydroxyphenyl)methyl]-ornithinamide and O-methyl-N-(butoxycarbonyl)-isourea in a yield of 34% of theory. Colourless, amorphous substance, Rf 0.74 (variant B).

IR (KBr): 1647.1, broad (amide-CO) cm⁻¹

ESI-MS: (M + H)⁺ = 574
(M + Na)⁺ = 596
(M + K)⁺ = 612

EXAMPLE 18

(R)-N²-(diphenylacetyl)-N-[(4-hydroxyphenyl)methyl]-N⁷-(phenylmethoxycarbonyl)-argininamide-acetate Prepared analogously to Example 10 from (R)-N²-(diphenylacetyl)-N-[(4-hydroxyphenyl)methyl]-ornithinamide and O-methyl-N-(phenylmethoxycarbonyl)-isourea in a yield of 36% of theory. Colourless, crystalline substance, Rf 0.76 (variant B).

IR (KBr): 1724.3 (urethane-CO), 1641.3 (amide-CO) cm⁻¹

ESI-MS: (M + H)⁺ = 608
(M + Na)⁺ = 630
(M + K)⁺ = 646

EXAMPLE 19

(R)-N-[[4-(aminocarbonylaminomethyl)phenyl]methyl]-N²-(diphenylacetyl)-N⁷-[[2-(ethoxycarbonyl)ethyl]aminocarbonyl]-argininamide-acetate a) (R)-N-[[4-(aminocarbonylaminomethyl)phenyl]methyl]-N²-(diphenylacetyl)-N⁷-[[2-(ethoxycarbonyl)ethyl]-aminocarbonyl]-N⁷'-nitro-argininamide Prepared analogously to Example 5a) from (R)-N-[[4-(aminocarbonyl-aminomethyl)phenyl]methyl]-N²-(diphenylacetyl)-N⁷-nitro-argininamide and ethyl 3-isocyanatopropionate in a yield of 39% of theory. Colourless crystals.

IR (KBr): 1726.2 (ester-CO), 1705.0 (urea-CO), 1633.6 (amide-CO) cm⁻¹

ESI-MS: (M + H)⁺ = 718
(M − H)⁻ = 716
(M + Na)⁺ = 740
(M + NH₄)⁺ = 735 b) (R)-N-[[4-(aminocarbonylaminomethyl)phenyl]methyl]-N²-(diphenylacetyl)-N⁷-[[2-(ethoxycarbonyl)ethyl]aminocarbonyl]-argininamide-acetate Prepared analogously to Example 1c) by catalytic hydrogenation of (R)-N-[[4-(aminocarbonylaminomethyl)phenyl]methyl]-N²-(diphenylacetyl)-N⁷-[[2-(ethoxycarbonyl)ethyl]aminocarbonyl]-N⁷'-nitro-argininamide in the presence of palladium black and 80% aqueous acetic acid in a yield of 40% of theory. Colourless crystals, R$_f$ 0.76 (variant B).

IR (KBr): 1728.1 (ester-CO), 1637.5 broad (urea/amide-CO) cm⁻¹

ESI-MS: (M + H)⁺ = 673
(M + Na)⁺ = 695
(M + K)⁺ = 711

EXAMPLE 20

(R)-N-[[4-(aminocarbonylaminomethyl)phenyl]methyl]-N⁷-[[2-(carboxy)ethyl]aminocarbonyl]-N²-(diphenylacetyl)-argininamide Prepared analogously to Example 3a) from (R)-N-[[4-(aminocarbonyl-aminomethyl)phenyl]methyl]-N²-(diphenylacetyl)-N⁷-[[2-(ethoxy-carbonyl)ethyl]aminocarbonyl]-argininamide-acetate by saponification with methanolic sodium hydroxide solution in a yield of 4% of theory. Colourless, crystalline substance, Rf 0.68 (variant B).

ESI-MS: (M + H)⁺ = 645
(M + Na)⁺ = 667

EXAMPLE 21

(R)-N²-(diphenylacetyl)-N-(phenylmethyl)-N⁷-(methoxycarbonyl)-argininamide

Prepared analogously to Example 10, but using isopropanol/glacial acetic acid=20/1 as solvent, from (R)-N²-(di-phenylacetyl)-N-(phenylmethyl)-ornithinamide and O-methyl-N-(methoxycarbonyl)-isourea in a yield of 38% of theory. Colourless crystals, mp. 132–134° C. and $R_f$ 0.65 (variant B).

IR (KBr): 1641.3 (broad, amide-CO) cm$^{-1}$

ESI-MS: $(M+H)^+$ = 516
$(M+Na)^+$ = 538

EXAMPLE 22

(R)-N$^2$-(diphenylacetyl)-N$^7$-(methylaminocarbonyl)-N-(phenylmethyl)-argininamide Prepared analogously to Example 21 from (R)-N$^2$-(diphenylacetyl)-N-(phenylmethyl)-ornithinamide and O-methyl-N-(methylaminocarbonyl)-isourea in a yield of 26% of theory. Colourless, amorphous compound, $R_f$ 0.66 (variant B).

IR (KBr): 1649 (broad, urea/amide-CO) cm$^{-1}$

ESI-MS: $(M+H)^+$ = 515
$(M+Na)^+$ = 537

EXAMPLE 23

(R)-N$^2$-(diphenylacetyl)-N-(phenylmethyl)-N$^7$-[(phenylmethyl)-aminocarbonyl]-argininamide Prepared analogously to Example 21 from (R)-N$^2$-(diphenylacetyl)-N-(phenylmethyl)-ornithinamide and O-methyl-N-[(phenylmethyl)-aminocarbonyl]-isourea in a yield of 9% of theory. Colourless crystals, mp. 142° C. and $R_f$ 0.77 (variant B).

IR (KBr): 1639.4 (broad, urea/amide-CO) cm$^{-1}$

ESI-MS: $(M+H)^+$ = 591
$(M+Na)^+$ = 613
$(M+K)^+$ = 629

EXAMPLE 24

(R)-N-[[4-(aminocarbonylaminomethyl)phenyl]methyl]-N$^2$-[(1H-indol-3-yl)acetyl]-N$^7$-(methylaminocarbonyl)-argininamide a) (R)-N-[[4-(aminocarbonylmethyl)phenyl]methyl]-N$^2$-[(1H-indol-3-yl)acetyl]-N$^7$-(methylaminocarbonyl)-N$^{7'}$-nitro-argininamide Prepared analogously to Example 1a), but using diisopropylethylamine as base and dimethylformamide as solvent, from (R)-N-[[4-(aminocarbonylmethyl)phenyl]methyl]-N$^2$-[(1H-indol-3-yl)acetyl]-N$^7$-nitro-argininamide and methylisocyanate in a yield of 34% of theory. Colourless crystalline substance.

IR (KBr): 1712.7 (urea-CO), 1631.7 (amide-CO) cm$^{-1}$

ESI-MS: $(M-H)^-$ = 593
$(M+Na)^+$ = 617 b) R)-N-[[4-(aminocarbonylaminomethyl)phenyl]methyl]-N$^2$-[(1H-indol-3-yl)acetyl]-N$^7$-(methylaminocarbonyl)-argininamide Prepared analogously to Example 1c) by catalytic hydrogenation of (R)-N-[[4-(aminocarbonylmethyl)phenyl]methyl]-N$^2$-[(1H-indol-3-yl)acetyl]-N$^7$-(methylaminocarbonyl)-N$^{7'}$-nitro-argininamide in the presence of palladium black and 80% aqueous acetic acid in a yield of 29% of theory. Colourless amorphous substance, Rf 0.49 (variant B).

IR (KBr): 1656.8, 1631.7 (broad, urea/amide-CO) cm$^{-1}$

ESI-MS: $(M+H)^+$ = 550
$(M+Na)^+$ = 572

EXAMPLE 25

(R)-N$^7$-(dimethylaminocarbonyl)-N$^2$-(diphenylacetyl)-N-[(4-hydroxyphenyl)methyl]-argininamide a) (R)-N$^7$-(dimethylaminocarbonyl)-N$^2$-(diphenylacetyl)-N-[(4-hydroxyphenyl)methyl]-N$^{7'}$-nitro-argininamide Prepared analogously to Example 1a), but using tetrahydrofuran as solvent, from (R)-N$^2$-(diphenylacetyl)-[(4-hydroxyphenyl)methyl]-N$^7$-nitro-argininamide and dimethylcarbamoylchloride in a yield of 22% of theory. Colourless crystalline substance.

ESI-MS: $(M+H)^+$ = 590
$(M+Na)^+$ = 612 b) (R)-N$^7$-(dimethylaminocarbonyl)-N$^2$-(diphenylacetyl)-N-[(4-hydroxyphenyl)methyl]-argininamide Prepared analogously to Example 1c) by catalytic hydrogenation of (R)-N$^7$-(dimethylaminocarbonyl)-N$^2$-(diphenylacetyl)-N-[(4-hydroxyphenyl)methyl]-N$^{7'}$-nitro-argininamide in the presence of palladium black and 80% aqueous acetic acid in a yield of 13% of theory. Colourless amorphous substance, Rf 0.58 (variant B).

IR (KBr): 1705.0 (urea-CO), 1656.8 (amide-CO) cm$^{-1}$
ESI-MS: $(M+H)^+$=545

EXAMPLE 26

(R)-N$^2$-[(1H-indol-3-yl)acetyl]-N-[(4-methoxyphenyl)methyl]-N$^7$-(methylaminocarbonyl)-argininamide Prepared analogously to Example 10 from (R)-N$^2$-[(1H-indol-3-yl)acetyl]-N-[(4-methoxyphenyl)methyl]-ornithinamide and O-methyl-N-(methylaminocarbonyl)-isourea in a yield of 8% of theory. Colourless amorphous substance, Rf 0.61 (variant B).

IR (KBr): 1647.1 (broad, amide-CO) cm$^{-1}$
ESI-MS: $(M+H)^+$=508

EXAMPLE 27

(R)-N$^2$-[(1H-indol-3-yl)acetyl]-N-[(4-methoxyphenyl)methyl]-N$^7$-[(3-phenylpropyl)aminocarbonyl]-argininamide Prepared analogously to Example 10 from (R)-N$^2$-[(1H-indol-3-yl)acetyl]-N-[(4-methoxyphenyl)methyl]-ornithinamide and O-methyl-N-[(3-phenylpropyl)

aminocarbonyl]-isourea in a yield of 2% of theory. Colourless amorphous substance, Rf 0.73 (variant B).

IR (KBr): 1652.9 (broad, urea/amide-CO) cm$^{-1}$
ESI-MS: (M+H)$^+$=612

EXAMPLE 28

(R)-N$^2$-(diphenylacetyl)-N-[(4-hydroxyphenyl) methyl]-N-methyl-N$^7$-(methylaminocarbonyl)-argininamide Prepared analogously to Example 21 from (R)-N$^2$-(diphenylacetyl)-N-[(4-hydroxyphenyl)methyl]-N-methyl-ornithinamide and O-methyl-N-(methylaminocarbonyl)-isourea in a yield of 1.2% of theory. Colourless, amorphous substance, Rf 0.66 (variant B).

ESI-MS: (M + H)$^+$ = 545
(M + Na)$^+$ = 567

EXAMPLE 29

(R)-N$^2$-(diphenylacetyl)-N-[(4-hydroxyphenyl) methyl]-N-methyl-N$^7$-[(phenylmethyl) aminocarbonyl]-argininamide Prepared analogously to Example 21 from (R)-N$^2$-(diphenylacetyl)-N-[(4-hydroxyphenyl)methyl]-N-methyl-ornithinamide and O-methyl-N-[(phenylmethyl) aminocarbonyl]-isourea in a yield of 4% of theory. Colourless crystals, mp. 167° C. and R$_f$ 0.76 (variant B).

IR (KBr): 1629.8 (broad, (urea/amide-CO) cm$^{-1}$

ESI-MS: (M + H)$^+$ = 621
(M + Na)$^+$ = 643

EXAMPLE 30

(R)-N$^2$-(diphenylacetyl)-N$^7$-(methoxycarbonyl)-N-[(4-methoxy-phenyl)methyl]-argininamide-hydrochloride Prepared analogously to Example 21 from (R)-N$^2$-(diphenylacetyl)-N-[(4-methoxyphenyl)methyl]-ornithinamide and O-methyl-N-(methoxycarbonyl)-isourea in a yield of 3% of theory. The product was converted into the hydrochloride with ethereal hydrogen chloride solution. Colourless crystals, mp. 145° C. and R$_f$ 0.68 (variant B).

IR (KBr): 1685.7 (guanidine), 1654.8 (broad, amide-CO) cm$^{-1}$

ESI-MS: (M + H)$^+$ = 546
(M + Na)$^+$ = 568

EXAMPLE 31

(R)-N$^2$-(diphenylacetyl)-N-[(4-methoxyphenyl) methyl]-N$^7$-[(phenylmethyl)aminocarbonyl]-argininamide Prepared analogously to Example 21 from (R)-N$^2$-(diphenylacetyl)-N-[(4-methoxyphenyl)methyl]-ornithinamide and O-methyl-N-[(phenylmethyl) aminocarbonyl]-isourea in a yield of 11% of theory. Colourless amorphous substance, Rf 0.77 (variant B).

IR (KBr): 1685.7 (guanidine), 1649.0 (broad, amide-CO) cm$^{-1}$

ESI-MS: (M + H)$^+$ = 546
(M + Na)$^+$ = 568

EXAMPLE 32

(R)-N-[(4-hydroxyphenyl)methyl]-N$^2$-[(6-methoxy-2-naphthyl)-acetyl]-N$^7$-(methylaminocarbonyl)-argininamide a) (R)-N-[(4-hydroxyphenyl)methyl]-N$^7$-(methylaminocarbonyl)-N$^2$-[(6-methoxy-2-naphthyl) acetyl]-N$^{7'}$-nitro-argininamide Prepared analogously to Example 5a) from (R)-N-[(4-hydroxyphenyl)-methyl]-N$^2$-[(6-methoxy-2-naphthyl) acetyl]-N$^7$-nitro-argininamide and methylisocyanate in a yield of 45% of theory. Colourless, amorphous substance.

IR (KBr): 1693.4 (urea-CO), 1635.5 (amide-CO) cm$^{-1}$

ESI-MS: (M + Na)$^+$ = 602
(M + NH$_4$)$^+$ = 590 b) (R)-N-[(4-hydroxyphenyl)methyl]-N$^2$-[(6-methoxy-2-naphthyl)acetyl]-N$^7$-(methylaminocarbonyl)-argininamide Prepared analogously to Example 1c) by catalytic hydrogenation of (R)-N-[(4-hydroxyphenyl)methyl]-N$^2$-[(6-methoxy-2-naphthyl)acetyl]-N$^7$-(methylaminocarbonyl)-N$^{7'}$-nitro-argininamide in the presence of palladium black and 80% aqueous acetic acid in a yield of 39% of theory. Colourless, amorphous substance, Rf 0.64 (variant B).

IR (KBr): 1635.5 (broad, urea/amide-CO) cm$^{-1}$
ESI-MS: (M+H)$^+$=535

EXAMPLE 33

(R)-N$^2$-(diphenylacetyl)-N-[(4-hydroxyphenyl) methyl]-N$^7$-[[4-(4-methoxyphenyl)butyl] aminocarbonyl]-argininamide-acetate a) (R)-N$^2$-(diphenylacetyl)-N$^7$-[[4-(4-methoxyphenyl) butyl]-aminocarbonyl]-N$^{7'}$-nitro-arginine Prepared analogously to Example 24a) from (R)-N$^2$-(diphenylacetyl)-N$^7$-nitro-arginine-sodium salt and 4-(4-methoxyphenyl)butyl-isocyanate in a yield of 19% of theory. Colourless, amorphous substance.

IR (KBr): 1705.0 (urea/carboxylic acid-CO) 1650(amide-CO) cm$^{-1}$ b) (R)-N$^2$-(diphenylacetyl)-N-[(4-hydroxyphenyl)methyl]-N$^7$-[[4-(4-methoxyphenyl)butyl]aminocarbonyl]-N$^{7'}$-nitro-argininamide To a solution of 0.6 g (0.97 mmol) of (R)-N$^2$-(diphenylacetyl)-N$^7$-[[4-(4-methoxyphenyl)butyl] aminocarbonyl]-N$^{7'}$-nitro-arginine in 20 ml of dimethylformamide were added successively 1 ml of diisopropylethylamine, 135 mg (1 mmol) of HOBT, 321 mg (1 mmol) of TBTU and 160 mg (1 mmol) of 4-hydroxybenzene-methanamine-hydrochloride and the mixture was stirred for 1 hour at ambient temperature. The mixture was stirred into 150 ml of water and then exhaustively extracted with ethyl acetate. The combined ethyl acetate extracts were dried over sodium sulphate and freed from solvent in vacuo. 670 mg (95% of theory) of a colourless, non-crystallising product were obtained, which was used in the following step without further purification.

IR (KBr): 1718.0 (urea-CO), 1646.9 (amide-CO) cm$^{-1}$ c) (R)-N$^2$-(diphenylacetyl)-N-[(4-hydroxyphenyl)methyl]-N$^7$-[[4-(4-methoxyphenyl)butyl]aminocarbonyl]-argininamide-acetate Prepared analogously to Example 1c) by catalytic hydrogenation of (R)-N$^2$-(diphenylacetyl)-N-[(4-hydroxyphenyl)methyl]-N$^7$-[[4-(4-methoxyphenyl)butyl]aminocarbonyl]-N$^{7'}$-nitro-argininamide in the presence of palladium black and 80% aqueous acetic acid in a yield of 38% of theory. Colourless crystals, R$_f$ 0.78 (variant B).

IR (KBr): 1679.9 (guanidine), 1643.3 (amide-CO) cm$^{-1}$

ESI-MS: (M + H)$^+$ = 679
(M + Na)$^+$ = 701

EXAMPLE 34

(R)-N$^2$-(diphenylacetyl)-N$^7$-[(3,3-diphenylpropyl)aminocarbonyl]-N-[(4-hydroxyphenyl)methyl]-argininamide-acetate a) (R)-N$^2$-(diphenylacetyl)-N$^7$-[(3,3-diphenyl-propyl)aminocarbonyl]-N$^{7'}$-nitro-arginine Prepared analogously to Example 4a) from (R)-N$^2$-(diphenylacetyl)-N$^7$-nitro-arginine-sodium salt and 3,3-diphenylpropylisocyanate in a yield of 35% of theory. Colourless, amorphous substance.

IR (KBr): 1705.0 (urea/carboxylic acid-CO), 1652.9 (amide-CO) cm$^{-1}$ b) (R)-N$^2$-(diphenylacetyl)-N$^7$-[(3,3-diphenylpropyl)aminocarbonyl]-N-[(4-hydroxyphenyl)methyl]-N$^{7'}$-nitro-arginine Prepared analogously to Example 33b) from (R)-N$^2$-(diphenylacetyl)-N$^7$-[(3,3-diphenylpropyl)aminocarbonyl]-N$^{7'}$-nitro-arginine and 4-hydroxybenzenemethanamine-hydrochloride in the presence of TBTU in a yield of 61% of theory. Colourless, amorphous substance, which was used in the following step without further purification.

c) (R)-N$^2$-(diphenylacetyl)-N$^7$-[(3,3-diphenylpropyl)aminocarbonyl]-N-[(4-hydroxyphenyl)methyl]-argininamide-acetate Prepared analogously to Example 1c) by catalytic hydrogenation of (R)-N$^2$-(diphenylacetyl)-N-[(4-hydroxyphenyl)methyl]-N$^7$-[(3,3-diphenylpropyl)aminocarbonyl]-N$^{7'}$-nitro-argininamide in the presence of palladium black and 80% aqueous acetic acid in a yield of 26% of theory. Colourless, amorphous substance, Rf 0.82 (variant B).

IR (KBr): 1652.9 (broad, urea/amide-CO) cm$^{-1}$

ESI-MS: (M + H)$^+$ = 711
(M + Na)$^+$ = 733

EXAMPLE 35

(R)-N$^7$-(cyclohexylaminocarbonyl)-N$^2$-(diphenylacetyl)-N-[(4-hydroxyphenyl)methyl]-argininamide-acetate a) (R)-N$^7$-(cyclohexylaminocarbonyl)-N$^2$-(diphenylacetyl)-N$^{7'}$-nitro-arginine Prepared analogously to Example 4a) from (R)-N$^2$-(diphenylacetyl)-N$^7$-nitro-arginine-sodium salt and cyclohexylisocyanate in a yield of 18% of theory. Colourless crystals, mp. 145–147° C.

IR (KBr): 1701.1 (urea/carboxylic acid-CO), 1647.1 (amide-CO) cm$^{-1}$

ESI-MS: (M + H)$^+$ = 539
(M + Na)$^+$ = 561
(M + NH$_4$)$^+$ = 556
(M − H + 2Na)$^+$ = 583 b) (R)-N$^7$-(cyclohexylaminocarbonyl)-N$^2$-(diphenylacetyl)-N-[(4-hydroxyphenyl)methyl]-N$^{7'}$-nitro-argininamide Prepared analogously to Example 33b) from (R)-N$^7$-(cyclohexylamino-carbonyl)-N$^2$-(diphenylacetyl)-N$^{7'}$-nitro-arginine and 4-hydroxybenzenemethanamine-hydrochloride in the presence of TBTU in a yield of 62% of theory. Colourless crystals, mp. 184° C., which were used in the following step without further purificationn.

IR (KBr): 1693.4 (urea-CO), 1639.4 (amide-CO) cm$^{-1}$ c) (R)-N$^7$-(cyclohexylaminocarbonyl)-N$^2$-(diphenylacetyl)-N-[(4-hydroxyphenyl)methyl]-argininamide-acetate Prepared analogously to Example 1c) by catalytic hydrogenation of (R)-N$^7$-(cyclohexylaminocarbonyl)-N$^2$-(diphenylacetyl)-N-[(4-hydroxyphenyl)methyl]-N$^{7'}$-nitro-argininamide in the presence of palladium black and 80% aqueous acetic acid in a yield of 63% of theory. Colourless, amorphous substance, Rf 0.78 (variant B).

IR (KBr): 1678.0 (guanidine; urea-CO) 1641.3 (amide-CO) cm$^{-1}$

ESI-MS: (M + H)$^+$ = 599
(M + Na)$^+$ = 621

EXAMPLE 36

(R)-N$^2$-(diphenylacetyl)-N-[(4-hydroxyphenyl)methyl]-N$^7$-(phenylaminocarbonyl)-argininamide-acetate a) (R)-N$^2$-(diphenylacetyl)-N$^7$-nitro-N$^{7'}$-(phenylaminocarbonyl)-arginine Prepared analogously to Example 4a) from (R)-N$^2$-(diphenylacetyl)-N$^7$-nitro-arginine-sodium salt and phenylisocyanate in a yield of 9% of theory. Colourless crystals.

IR (KBr): 1712.7 (urea/carboxylic acid-CO), 1652.9 (amide-CO) cm$^{-1}$

ESI-MS: (M + H)$^+$ = 533
(M + Na)$^+$ = 555
(M + NH$_4$)$^+$ = 550
(M − H + 2Na)$^+$ = 577 b) (R)-N$^2$-(diphenylacetyl)-N-[(4-hydroxyphenyl)methyl]-N$^7$-nitro-N$^{7'}$-(phenylaminocarbonyl)-argininamide Prepared analogously to Example 33b) from (R)-N$^2$-(diphenylacetyl)-N$^7$-nitro-N$^{7'}$-(phenylaminocarbonyl)-arginine and 4-hydroxybenzenemethanamine-hydrochloride in the presence of TBTU in a yield of 60% of theory. Colourless crystals, mp. 158–160° C., which were used in the following step without further purification.

IR (KBr): 1716.5 (urea-CO), 1635.5 (amide-CO) cm$^{-1}$

ESI-MS: (M − H)$^-$ = 636
(M + Na)$^+$ = 660 c) (R)-N$^2$-(diphenylacetyl)-N-[(4-hydroxyphenyl)methyl]-N$^{7\prime}$-(phenylaminocarbonyl)-argininamide-acetate Prepared analogously to Example 1c) by catalytic hydrogenation of (R)-N$^2$-(diphenylacetyl)-N-[(4-hydroxyphenyl)methyl]-N$^7$-nitro-N$^{7\prime}$-(phenylaminocarbonyl)-argininamide in the presence of palladium black and 80% aqueous acetic acid in a yield of 27% of theory. Colourless, amorphous substance, Rf 0.81 (variant B).

IR (KBr): 1652.9 (broad, urea/amide-CO, guanidine) cm$^{-1}$

ESI-MS: (M + H)$^+$ = 593
(M + Na)$^+$ = 615
(M + K)$^+$ = 631

EXAMPLE 37

(R)-N$^2$-(diphenylacetyl)-N-[(4-hydroxyphenyl)methyl]-N$^7$-[(2-naphthylmethyl)aminocarbonyl]-argininamide-acetate a) (R)-N$^2$-(diphenylacetyl)-N$^7$-[(2-naphthylmethyl)aminocarbonyl]-N$^{7\prime}$-nitro-arginine Prepared analogously to Example 4a) from (R)-N$^2$-(diphenylacetyl)-N$^7$-nitro-arginine-sodium salt and 2-naphthylmethylisocyanate in a yield of 10% of theory. Colourless, amorphous substance.

b) (R)-N$^2$-(diphenylacetyl)-N-[(4-hydroxyphenyl)methyl]-N$^7$-[(2-naphthylmethyl)aminocarbonyl]-N$^{7\prime}$-nitro-argininamide Prepared analogously to Example 33b) from (R)-N$^2$-(diphenylacetyl)-N$^7$-[(2-naphthylmethyl)aminocarbonyl]-N$^{7\prime}$-nitro-arginine and 4-hydroxybenzenemethanamine-hydrochloride in the presence of TBTU in a quantitative yield. Colourless, amorphous substance, which was used in the following step without further purification.

c) (R)-N$^2$-(diphenylacetyl)-N-[(4-hydroxyphenyl)methyl]-N$^7$-[(2-naphthylmethyl)aminocarbonyl]-argininamide-acetate Prepared analogously to Example 1c) by catalytic hydrogenation of (R)-N$^2$-(diphenylacetyl)-N-[(4-hydroxyphenyl)methyl]-N$^7$-[(2-naphthylmethyl)aminocarbonyl]-N$^{7\prime}$-nitro-argininamide in the presence of palladium black and 80% aqueous acetic acid in a yield of 1% of theory. Colourless, amorphous substance, R$_f$ 0.79 (variant B).

IR (KBr): 1654.8 (urea/amide-CO, guanidine) cm$^{-1}$

ESI-MS: (M + H)$^+$ = 657
(M − H)$^-$ = 655
(M + Na)$^+$ = 679

EXAMPLE 38

(R,S)-N$^2$-(diphenylacetyl)-N-[(4-hydroxyphenyl)methyl]-N$^5$-methyl-N$^7$-(methylaminocarbonyl)-argininamide Prepared analogously to Example 3a) from (R,S)-N$^2$-(diphenylacetyl)-N$^5$-methyl-N$^7$-(methylaminocarbonyl)-N-[[4-(methylaminocarbonyloxy)phenyl]methyl]-argininamide by saponification with ethanolic sodium hydroxide solution in a yield of 80% of theory. Colourless, amorphous substance, Rf 0.53 (variant B).

IR (KBr): 1647.1 (urea/amide-CO) cm$^{-1}$

ESI-MS: (M+H)$^+$=545

EXAMPLE 39

(R,S)-N$^2$-(diphenylacetyl)-N$^5$-methyl-N$^7$-(methylaminocarbonyl)-N-[[4-(methylaminocarbonyloxy)phenyl]methyl]-argininamide Prepared analogously to Example 1a) from (R,S)-N$^2$-(diphenylacetyl)-N-[(4-hydroxyphenyl)methyl]-N$^5$-methylargininamide and methylisocyanate in a yield of 54% of theory. Colourless, amorphous substance, Rf 0.45 (variant B).

IR (KBr): 1730.0 (ester-CO), 1652.9 (amide-CO) cm$^{-1}$

ESI-MS: (M + H)$^+$ = 602
(M − H)$^-$ = 600
(M + Na)$^+$ = 624

EXAMPLE 40

(R)-N$^2$-(diphenylacetyl)-N-[(4-methylphenyl)methyl]-N$^7$-(5-methyl-2-thiazolyl)-argininamide The mixture of 430 mg (1 mmol) of (R)-N$^2$-(diphenylacetyl)-N-[(4-methylphenyl)methyl]-ornithinamide, 158 mg (0.5 mmol) of S-methyl-N-(5-methyl-2-thiazolyl)-thiuroniumiodide and 20 ml of ethanol was refluxed for 72 hours. The solvent was eliminated in vacuo, the residue was purified by column chromatography on silica gel (Baker, 30–60 μm) using ethyl acetate/methanol 95/5 (v/v) as eluant. Working up the corresponding fractions yielded 90 mg (32% of theory) of a colourless, amorphous substance, Rf 0.60 (variant A).

IR (KBr): 1649.0 (amide-CO) cm$^{-1}$

ESI-MS: (M+H)$^+$=569

EXAMPLE 41

(R)-N$^2$-(diphenylacetyl)-N-[(4-hydroxyphenyl)methyl]-N$^7$-(5-methyl-2-thiazolyl)-argininamide Prepared analogously to Example 40 from (R)-N$^2$-(diphenylacetyl)-N-[(4-hydroxyphenyl)methyl]-ornithinamide and S-methyl-N-(5-methyl-2-thiazolyl)-thiuronium iodide in a yield of 7% of theory. Colourless, amorphous substance, Rf 0.45 (variant A).

IR (KBr): 1645.2 (amide-CO) cm$^{-1}$

ESI-MS: (M + H)$^+$ = 571
(M − H)$^-$ = 569
(M + Na)$^+$ = 593

EXAMPLE 42

(R)-N$^2$-(diphenylacetyl)-N-[(4-hydroxyphenyl)methyl]-N$^7$-phenyl-argininamide-acetate Prepared analogously to Example 40, but using dimethylformamide as solvent, from (R)-N$^2$-(diphenylacetyl)-N-

[(4-hydroxyphenyl)methyl]-ornithinamide and S-methyl-N-phenyl-thiuronium iodide in a yield of 10% of theory. Colourless, amorphous substance, Rf 0.76 (variant B).

IR (KBr): 1654.8 (amide-CO) cm$^{-1}$

ESI-MS: (M+H)$^+$=550

EXAMPLE 43

(R)-N-[[4-(aminocarbonylaminomethyl)phenyl]methyl]-N$^2$-(diphenylacetyl)-N$^7$-(2-pyridinyl)-argininamide-diacetate Prepared analogously to Example 42 from (R)-N$^2$-(diphenylacetyl)-N-[[4-(aminocarbonylaminomethyl)phenyl]methyl]-ornithinamide and S-methyl-N-(2-pyridinyl)-thiuronium iodide in a yield of 8% of theory. Colourless, amorphous substance, Rf 0.60 (variant B).

IR (KBr): 1639.4 (broad, amide-CO) cm$^{-1}$

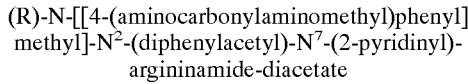

EXAMPLE 44

(R)-N$^2$-(diphenylacetyl)-N-[(4-hydroxyphenyl)methyl]-N$^7$-(4-methyl-2-thiazolyl)-argininamide Prepared analogously to Example 40 from (R)-N$^2$-(diphenylacetyl)-N-[(4-hydroxyphenyl)methyl]-ornithinamide and S-methyl-N-(4-methyl-2-thiazolyl)-thiuronium iodide in a yield of 4% of theory. Colourless, amorphous substance, Rf 0.43 (variant A).

IR (KBr): 1645.2 (amide-CO) cm–1

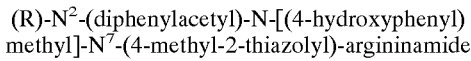

EXAMPLE 45

(R)-N$^2$-(diphenylacetyl)-N-[(4-methylphenyl)methyl]-N$^7$-(4-methyl-2-thiazolyl)-argininamide Prepared analogously to Example 40 from (R)-N$^2$-(diphenylacetyl)-N-[(4-methylphenyl)methyl]-ornithinamide and S-methyl-N-(4-methyl-2-thiazolyl)-thiuronium iodide in a yield of 3% of theory. Colourless, amorphous substance, Rf 0.76 (variant B).

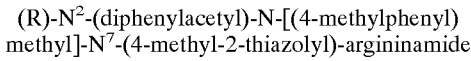

EXAMPLE 46

(R)-N$^2$-(diphenylacetyl)-N-[(4-methylphenyl)methyl]-N$^7$-(5-methyl-2-pyridinyl)-argininamide-hydriodide Prepared analogously to Example 40 from (R)-N$^2$-(diphenylacetyl)-N-[(4-methylphenyl)methyl]-ornithinamide and S-methyl-N-(5-methyl-2-pyridinyl)-thiuronium iodide in a yield of 10% of theory. Colourless, amorphous substance, Rf 0.84 (variant B).

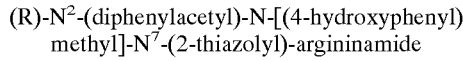

EXAMPLE 47

(R)-N$^2$-(diphenylacetyl)-N-[(4-hydroxyphenyl)methyl]-N$^7$-(2-thiazolyl)-argininamide Prepared analogously to Example 42 from (R)-N$^2$-(diphenylacetyl)-N-[(4-hydroxyphenyl)methyl]-ornithinamide and S-methyl-N-(2-thiazolyl)-thiuronium iodide in a yield of 2% of theory. Colourless, amorphous substance, Rf 0.45 (variant A).

IR (KBr): 1652.9 (amide-CO) cm$^{-1}$

ESI-MS: (M+H)$^+$=557

EXAMPLE 48

(R)-N$^2$-(diphenylacetyl)-N-[(4-hydroxyphenyl)methyl]-N$^7$-(5-methyl-2-pyridinyl)-argininamide-hydriodide Prepared analogously to Example 40 from (R)-N$^2$-(diphenylacetyl)-N-[(4-hydroxyphenyl)methyl]-ornithinamide and S-methyl-N-(5-methyl-2-pyridinyl)-thiuronium iodide in a yield of 9% of theory. Colourless, amorphous substance, Rf 0.85 (variant B).

IR (KBr): 1647.1 (amide-CO) cm$^{-1}$

ESI-MS: (M+H)$^+$=565

EXAMPLE 49

(R)-N$^2$-(diphenylacetyl)-N-methyl-N$^7$-(4-methyl-2-thiazolyl)-N-(phenylmethyl)-argininamide-acetate Prepared analogously to Example 42 from (R)-N$^2$-(diphenylacetyl)-N-methyl-N-(phenylmethyl)-ornithinamide and S-methyl-N-(4-methyl-2-thiazolyl)-thiuronium iodide in a yield of 2% of theory. Colourless, amorphous substance, Rf 0.51 (variant A).

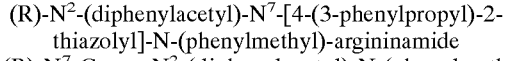

EXAMPLE 50

(R)-N$^2$-(diphenylacetyl)-N$^7$-[4-(3-phenylpropyl)-2-thiazolyl]-N-(phenylmethyl)-argininamide a) (R)-N$^7$-Cyano-N$^2$-(diphenylacetyl)-N-(phenylmethyl)-argininamide The mixture of 3.5 g (8.43 mmol) of (R)-N$^2$-(diphenylacetyl)-N-(phenylmethyl)-ornithinamide, 2.0 g (8.4 mmol) of diphenyl cyanocarbimidate and 30 ml of dimethylformamide was stirred for 2 hours at ambient temperature. Then dry ammonia gas was piped in till saturation point was reached and the mixture was kept for 4 days at ambient temperature. The solvent was distilled off in vacuo, the residue was carefully stirred with ether, the ether phase was discarded and the residue was again evaporated down in vacuo. 4.0 g (99% of theory) of a colourless, amorphous product were obtained, which was used in the following step without further purification.

IR (KBr): 2171.7 (C≡N), 1651.0 (amide-CO) cm$^{-1}$

ESI-MS: (M + H)$^+$ = 483
(M + Na)$^+$ = 505
(M + NH$_4$)$^+$ = 500 b) (R)-N$^7$-(aminothiocarbonyl)-N$^2$-(diphenylacetyl)-N-(phenylmethyl)-argininamide A solution of 4.0 g (8.293 mmol) of (R)-N$^7$-cyano-N$^2$-(diphenylacetyl)-N-(phenylmethyl)-argininamide in 50 ml of anhydrous pyridine saturated with hydrogen sulphide was heated to 50° C. for 20 hours in a bomb tube. The mixture was evaporated down in vacuo, the residual product was purified by column chromatography on silica gel (Baker, 30–60 μm) using ethyl acetate/methanol 1/1 (v/v) as eluant. Working up the corresponding fractions yielded 1.1 g (26% of theory) of a colourless, amorphous resin.

IR (KBr): 1649.0 (amide-CO) cm$^{-1}$

ESI-MS: (M + H)$^+$ = 517
(M + Na)$^+$ = 539
(M + K)$^+$ = 555 c) R)-N$^2$-(diphenylacetyl)-N$^7$-[4-(3-phenylpropyl)-2-thiazolyl]-N-(phenylmethyl)-argininamide The mixture of 775 mg (1.5 mmol) of (R)-N$^7$-(aminothiocarbonyl)-N$^2$-(diphenylacetyl)-N-(phenylmethyl)-argininamide, 398 mg (2.0 mmol) of 1-chlor-5-phenyl-2-pentanone and 20 ml of acetone was refluxed for 5 hours. The solvent was distilled off, the residue purified on silica gel (Baker, 30–60 μm) using ethyl acetate/methanol 1/1 (v/v) as eluant. Working up the corresponding fractions yielded 250 mg (25% of theory) of a colourless, amorphous substance, Rf 0.70 (variant A).

IR (KBr): 1645.2 (amide-CO) cm–1

ESI-MS: (M + H)$^+$ = 659
(M + Na)$^+$ = 681

EXAMPLE 51

(R)-N$^2$-(diphenylacetyl)-N$^7$-[4-(2-phenylethyl)-2-thiazolyl]-N-(phenylmethyl)-argininamide Prepared analogously to Example 50c) from (R)-N$^7$-(aminothiocarbonyl)-N$^2$-(diphenylacetyl)-N-(phenylmethyl)-argininamide and 1-chloro-4-phenyl-2-butanone in a yield of 22% of theory. Colourless, amorphous substance, Rf 0.64 (variant A).

ESI-MS: (M + H)$^+$ = 645
(M + Na)$^+$ = 667
(M + K)$^+$ = 683

EXAMPLE 52

(R)-N$^2$-(diphenylacetyl)-N-[(4-hydroxyphenyl) methyl]-N$^7$-methyl-argininamide-diacetate Prepared analogously to Example 42 from (R)-N$^2$-(diphenylacetyl)-N-[(4-hydroxyphenyl)methyl]-ornithinamide and S,N-dimethyl-thiuronium iodide in a yield of 19% of theory. Colourless, amorphous substance, Rf 0.54 (variant B).

IR (KBr): 1652.9 (broad, guanidine, amide-CO) cm$^{-1}$

ESI-MS: (M+H)$^+$=488

EXAMPLE 53

(R)-N$^2$-(diphenylacetyl)-N$^7$-[4-(2-phenylethyl)-2-thiazolyl]-N-[[4-(phenylmethoxy)phenyl]methyl]-argininamide a) (R)-N$^7$-Cyano-N$^2$-(diphenylacetyl)-N-[[4-(phenylmethoxy)-phenyl]methyl]-argininamide Prepared analogously to Example 50a) from (R)-N$^2$-diphenylacetyl)-N-[[4-(phenylmethoxy)phenyl]methyl]-ornithinamide and diphenyl cyanocarbimidate and ammonia in a quantitative yield. Colourlesss, amorphous resin.

IR (KBr): 2173.6 (C≡N), 1652.9 (amide-CO) cm$^{-1}$

ESI-MS: (M + H)$^+$ = 589
(M + Na)$^+$ = 611
(M + K)$^+$ = 627
(M − H)$^-$ = 587 b) (R)-N$^7$-(aminothiocarbonyl)-N$^2$-(diphenylacetyl)-N-[[4-(phenylmethoxy)phenyl]methyl]-argininamide Prepared analogously to Example 50b) from (R)-N$^7$-Cyano-N$^2$-(diphenylacetyl)-N-[[4-(phenylmethoxy)phenyl]methyl]-argininamide and hydrogen sulphide in a yield of 31% of theory. Colourless, amorphous substance.

IR (KBr): 1637.5 (broad, amide-CO) cm$^{-1}$

ESI-MS: (M + H)$^+$ = 623
(M + Na)$^+$ = 645 c) (R)-N$^2$-(diphenylacetyl)-N$^7$-[4-(2-phenylethyl)-2-thiazolyl]-N-[[4-(phenylmethoxy)phenyl]methyl]-argininamide Prepared analogously to Example 50c) from (R)-N$^7$-(aminothiocarbonyl)-N$^2$-(diphenylacetyl)-N-[[4-(phenylmethoxy)phenyl]methyl]-argininamide and 1-chloro-4-phenyl-2-butanone in a yield of 17% of theory. Colourless, amorphous substance, Rf 0.82 (variant A).

IR (KBr): 1641.3 broad (amide-CO) cm$^{-1}$

ESI-MS: (M + H)$^+$ = 751
(M + Na)$^+$ = 773

EXAMPLE 54

(R)-N$^2$-(diphenylacetyl)-N-[[4-(phenylmethoxy) phenyl]methyl]-N$^7$-[4-(3-phenylpropyl)-2-thiazolyl]-argininamide Prepared analogously to Example 50c) from (R)-N$^7$-(aminothiocarbonyl)-N$^2$-(diphenylacetyl)-N-[[4-(phenylmethoxy)phenyl]methyl]-argininamide and 1-chloro-5-phenyl-2-pentanone in a yield of 52% of theory. Colourless, amorphous substance, Rf 0.83 (variant A).

IR (KBr): 1645.2 broad (amide-CO) cm$^{-1}$

ESI-MS: (M + H)$^+$ = 765
(M + Na)$^+$ = 787
(M − H)$^-$ = 763

EXAMPLE 55

(R)-N$^2$-(diphenylacetyl)-N$^7$-(4-methyl-2-thiazolyl)-N-[[4-(phenylmethoxy)phenyl]methyl]-argininamide Prepared analogously to Example 50c) from (R)-N$^7$-(aminothiocarbonyl)-N$^2$-(diphenylacetyl)-N-[[4-(phenylmethoxy)phenyl]methyl]-argininamide and chloroacetone in a yield of 39% of theory. Colourless, amorphous substance, Rf 0.65 (variant A).

IR (KBr): 1645.2 (broad, amide-CO) cm$^{-1}$

ESI-MS: (M + H)$^+$ = 661
(M + Na)$^+$ = 683
(M + K)$^+$ = 699

EXAMPLE 56

(R,S)-N$^2$-(diphenylacetyl)-N-[(4-hydroxyphenyl)methyl]-N$^7$-[3-(methoxycarbonyl)-1-oxopropyl]-argininamide Prepared analogously to Example 21 from (R)-N$^2$-(diphenylacetyl)-N-[(4-hydroxyphenyl)methyl]-ornithinamide and O-methyl-N-[3-(methoxycarbonyl)-1-oxopropyl]-isourea in a yield of 14% of theory. Colourless, amorphous compound, R$_f$ 0.68 (variant B).

IR (KBr): 1735.8 (carboxylic acid ester-CO), 1668.3, 1635.5 (amide-CO) cm$^{-1}$ ESI-MS: (M + H)$^+$ = 588
(M + Na)$^+$ = 610

EXAMPLE 57

(R)-N$^2$-(diphenylacetyl)-N-[(4-hydroxyphenyl)methyl]-N$^7$-[(4-pyridinyl)carbonyl]-argininamide The mixture of 800 mg (1.63 mmol) of (R)-N$^2$-(diphenylacetyl)-N-[(4-hydroxyphenyl)methyl]-argininamide-hydrate, 283 mg (2.0 mmol) of 4-pyridinecarboxylic acid chloride, 150 ml of tetrahydrofuran and 1 ml of triethylamine was refluxed for 18 hours. The solvent was distilled off, the residue divided between water and ethyl acetate, the ethyl acetate phase was dried over sodium sulphate and again evaporated down. The residue remaining was purified by column chromatography on silica gel (Macherey-Nagel, 0.063-0.2 mm) using first dichloromethane/methanol=9/1 (v/v), then dichloromethane/methanol/conc. aqueous ammonia=9/1/0,3 (v/v/v) as eluant. By working up the corresponding fractions 80 mg (8.5% of theory) of the desired compound were obtained in the form of a colourless, amorphous substance R$_f$ 0.48 (variant A).

IR (KBr): 1652.9 (amide-CO) cm$^{-1}$

ESI-MS: (M + H)$^+$ = 579
(M + Na)$^+$ = 601
(M − H)$^-$ = 577

EXAMPLE 58

(R,S)-N-[[4-(aminocarbonylmethyl)phenyl]methyl]-N$^2$-(diphenylacetyl)-N$^5$-methyl-N$^7$-(methylaminocarbonyl)-argininamide Prepared analogously to Example 1a) from (R,S)-N-[[4-(aminocarbonylmethyl)phenyl]methyl]-N$^2$-(diphenylacetyl)-N$^5$-methyl-argininamide and methylisocyanate in a yield of 31% of theory. Colourless crystals, mp. 185–192° C. and R$_f$ 0.38 (variant B).

IR (KBr): 1635.5 broad (amide-CO) cm$^{-1}$

ESI-MS: (M + H)$^+$ = 586
(M + Na)$^+$ = 608

EXAMPLE 59

(R)-N$^2$-(diphenylacetyl)-N$^7$-(4-methyl-2-thiazolyl)-N-methyl-N-[[4-(phenylmethoxy)phenyl]methyl]-argininamide a) (R)-N$^5$-(tert.-butoxycarbonyl)-N$^2$-(9-fluorenylmethoxycarbonyl)-N-methyl-N-[[4-(phenylmethoxy)phenyl]methyl]-ornithinamide Prepared analogously to Example 33b) from (R)-N$^5$-(tert.-butoxy-carbonyl)-N$^2$-(9-fluorenylmethoxycarbonyl)-ornithine and N-methyl-4-(phenylmethoxy)benzenemethanamine in the presence of TBTU in a quantitative yield. Colourless, highly viscous oil, which was used in the following step without further purification.

b) (R)-N$^5$-(tert.-butoxycarbonyl)-N-methyl-N-[[4-(phenylmethoxy)phenyl]methyl]-ornithinamide The solution of 9.3 g (14.02 mmol) of (R)-N$^5$-(tert.-butoxycarbonyl)-N$^2$-(9-fluorenylmethoxycarbonyl)-N-methyl-N-[[4-(phenylmethoxy)phenyl]methyl]-ornithinamide in 200 ml of tetrahydrofuran was mixed with 10 ml of diethylamine and stirred overnight at ambient temperature. The residue remaining after evaporation of the solvent was purified by column chromatography on silica gel(Baker, 30–60 μm). 4.6 g (74% of theory) of a colourless, highly viscous, non-crystallising oil were obtained.

IR (KBr): 1706.9 (urethane-CO), 1641.3 (amide-CO) cm$^{-1}$

MS: M$^+$–441 c) (R)-N$^5$-(tert.-butoxycarbonyl)-N$^2$-(diphenylacetyl)-N-methyl-N-[[4-(phenylmethoxy)phenyl]methyl]-ornithinamide Prepared analogously to Example 33b) from diphenylacetic acid and (R)-N$^5$-(tert.-butoxycarbonyl)-N-methyl-N-[[4-(phenylmethoxy)-phenyl]methyl]-ornithinamide in the presence of TBTU in a yield of 91% of theory. Colourless, amorphous substance.

IR (KBr): 1710.8 (urethane-CO), 1674.1 (amide-CO) cm$^{-1}$ d) (R)-N$^2$-(diphenylacetyl)-N-methyl-N-[[4-(phenylmethoxy)-phenyl]methyl]-ornithinamide Prepared analogously to Example 1b) from (R)-N$^5$-(tert.-butoxy-carbonyl)-N$^2$-(diphenylacetyl)-N-methyl-N-[[4-

(phenylmethoxy)-phenyl]methyl]-ornithinamide and trifluoroacetic acid in a yield of 91% of theory. Colourless, amorphous substance.

IR (KBr): 1674.1 (amide-CO), 1631.7 (amide-CO; C=C) cm$^{-1}$

ESI-MS: (M+H)$^+$ = 536
(M+Na)$^+$ = 558 e) (R)-N$^7$-Cyano-N$^2$-(diphenylacetyl)-N-methyl-N-[[4-(phenylmethoxy)phenyl]methyl]-argininamide Prepared analogously to Example 50a) from (R)-N$^2$-(diphenylacetyl)-N-methyl-N-[[4-(phenylmethoxy)phenyl]methyl]-ornithinamide and diphenyl cyanocarbimidate and ammonia in a yield of 74% of theory. Colourless, amorphous substance.

f) (R)-N$^7$-(aminothiocarbonyl)-N$^2$-(diphenylacetyl)-N-methyl-N-[[4-(phenylmethoxy)phenyl]methyl]-argininamide Prepared analogously to Example 50b) from (R)-N$^7$-cyano-N$^2$-(diphenyl-acetyl)-N-methyl-N-[[4-phenylmethoxy)phenyl]methyl]-argininamide and hydrogen sulphide in a yield of 57% of theory. Colourless, amorphous, foamy substance.

IR (KBr): 2171.7 (C=N—C≡N), 1625.9 (broad, amide-CO; C=C) cm$^{-1}$

ESI-MS: (M+H)$^+$ = 637
(M+Na)$^+$ = 659 g) (R)-N$^2$-(diphenylacetyl)-N-methyl-N$^7$-(4-methyl-2-thiazolyl)-N-[[4-(phenylmethoxy)phenyl]methyl]-argininamide Prepared analogously to Example 50c) from (R)-N$^7$-(aminothiocarbonyl)-N$^2$-(diphenylacetyl)-N-methyl-N-[[4-(phenylmethoxy)phenyl]methyl]-argininamide and chloroacetone in a yield of 47% of theory. Colourless, amorphous substance, Rf 0.73 (variant A).

IR (KBr): 1629.8 (broad, amide-CO; C=C) cm$^{-1}$

ESI-MS: (M+H)$^+$ = 675
(M+Na)$^+$ = 697

We claim:

1. A compound of the formula

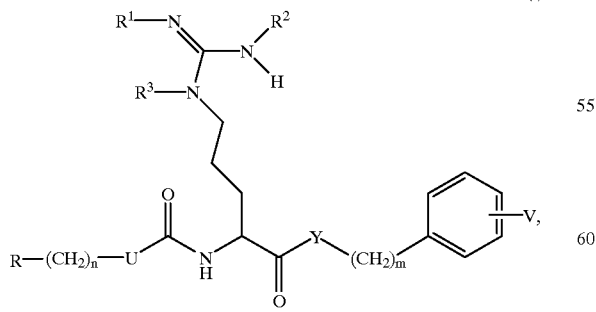

(I)

wherein
R denotes a phenyl, 1-naphthyl or 2-naphthyl, a 5-membered heteroaromatic ring linked via a carbon atom and containing a nitrogen, oxygen or sulphur atom or a nitrogen atom and an oxygen, a sulphur or further nitrogen atom, wherein a nitrogen atom of an imino group of said 5-membered heteroaromatic ring is optionally substituted by an alkyl, alkoxycarbonylalkyl, carboxyalkyl, dialkylaminoalkyl, aminocarbonyl, alkylaminocarbonyl, dialkylaminocarbonyl or alkoxycarbonyl, or a 6-membered heteroaromatic ring linked via a carbon atom, containing 1, 2 or 3 nitrogen atoms, wherein a 1,4-butadienylene group is optionally attached both to the 5-membered or to the 6-membered heteroaromatic rings via two adjacent carbon atoms to form bicyclic heteroaromatic rings which are optionally bound via a carbon atom of the 1,4-butadienylene group, wherein the groups mentioned for R hereinbefore, including the mono- and bicyclic heteroaromatic rings in their carbon skeleton, are optionally mono-, di- or at most trisubstituted by fluorine, chlorine, bromine, alkyl, cycloalkyl groups with 3 to 8 carbon atoms, alkoxy, phenyl, phenylalkoxy, trifluoromethyl, alkoxycarbonylalkyl, carboxyalkyl, dialkylaminoalkyl, hydroxy, amino, acetylamino, propionylamino, benzoyl, benzoylamino, benzoylmethylamino, aminocarbonyl, alkylaminocarbonyl, dialkylaminocarbonyl, alkanoyl, cyano, trifluoromethoxy, trifluoromethylthio, trifluoromet[ ]hylsulphynyl or trifluoromethylsulphonyl, wherein the substituents are identical or different and the ab)ovementioned benzoyl, benzoylamino and benzoylmethylamino groups are optionally substituted in the phenyl moiety by fluorine, chlorine, bromine, alkyl, trifluoromethyl, amino or acetylamino, or R is a diphenylmethyl group, wherein
the phenyl groups independently of one another are optionally mono- or disubstituted by fluorine, chlorine, bromine, methyl, methoxy, hydroxycarbonylmethoxy, alkoxycarbonylmethoxy, hydroxy or trifluoromethyl, wherein the substituents in each case are identical or different;

n denotes the numbers 0, 1 or 2,
U denotes a single bond, a oxygen atom or an —NH— group,
R$^1$ denotes a branched or unbranched aliphatic alkylcarbonyl containing 2 to 5 carbon atoms optionally substituted in the alkyl moiety by an alkoxycarbonyl, phenylalkoxycarbonyl, phenyl or by a 5- or 6-membered heteroaromatic ring linked via a carbon atom or a benzoyl group wherein the phenyl moiety is optionally replaced by a 5- or 6-membered heteroaromatic ring linked via a carbon atom, wherein the 5-membered heteroaromatic rings mentioned hereinbefore contain a nitrogen, an oxygen or sulphur atom or a nitrogen atom and an additional oxygen, sulphur or further nitrogen atom and are optionally substituted by an alkyl group at a nitrogen atom, the 6-membered heteroaromatic rings contain 1, 2 or 3 nitrogen atoms; wherein phenyl groups and 5- or 6-membered heteroaromatic rings in their carbon skeleton mentioned hereinbefore are optionally mono-, di- or tri- substituted by fluorine, chlorine, bromine, alkyl, cycloalkyl groups with 3 to 8 carbon atoms, alkoxy, trifluoromethyl, alkoxycarbonylalkyl, carboxyalkyl, hydroxy, amino, acetylamino, propionylamino, aminocarbonyl, alkylaminocarbonyl, dialkylaminocarbonyl, alkanoyl, cyano, trifluoromethoxy, trifluoromethylthio, trifluoromethylsulphynyl or trifluoromethylsulphonyl, wherein the substituents are identical or different, the aminocarbonyl group in this subparagraph is optionally mono- or disubstituted at the nitrogen atom by alkyl, phenylalkyl, (1-naphthyl)alkyl, (2-naphthyl)alkyl, alkoxycarbonylalkyl, phenylalkoxycarbonylalkyl, phenoxycarbonylalkyl, carboxyalkyl, diphenylalkyl, phenyl, cycloalkyl or cycloalkylalkyl groups with 3 to 8 carbon atoms in the ring in each case, the substituents are identical or different and the abovementioned phenyl groups are optionally independently mono- or disubstituted by fluorine, chlorine, bromine, methyl, methoxy, hydroxycarbonylmethoxy, alkoxycarbonylmethoxy, hydroxy or trifluoromethyl;

or $R^1$ is an alkoxycarbonyl or phenylalkoxycarbonyl, wherein the phenyl moiety is optionally mono- or disubstituted by fluorine, chlorine, bromine, methyl, methoxy, hydroxycarbonylmethoxy, alkoxycarbonylmethoxy, hydroxy or trifluoromethyl wherein the substituents in each case are identical or different, or $R^1$ is phenyl, a five-membered heteroaromatic ring bound via a carbon atom which contains a nitrogen, oxygen or sulphur atom or a nitrogen atom and an oxygen, sulphur or further nitrogen atom, wherein a nitrogen atom of an imino group of said five-membered heteroaromatic ring is optionally substituted by an alkyl, or a 6-membered heteroaromatic ring linked via a carbon atom, which contains 1, 2 or 3 nitrogen atoms, wherein the phenyl group and 5- and 6-membered heteroaromatic rings in their carbon skeleton are optionally mono-, di- or at most trisubstituted, by fluorine, chlorine, bromine, alkyl, cycloalkyl groups with 3 to 8 carbon atoms, phenylalkyl, alkoxy, trifluoromethyl, alkoxycarbonylalkyl, carboxyalkyl, hydroxy, amino, acetylamino, propionylamino, aminocarbonyl, alkylaminocarbonyl, dialkylaminocarbonyl, alkanoyl, cyano, trifluoromethoxy, trifluoromethylthio, trifluoromethylsulphinyl or trifluoromethylsulphonyl and wherein the substituents are identical or different;

or, if $R^2$ denotes a hydrogen atom, $R^1$ is optionally methyl;

$R^2$ denotes a hydrogen atom, an alkyl or phenylalkyl optionally mono- or disubstituted in the phenyl moiety by fluorine, chlorine, bromine, alkyl, trifluoromethyl, amino or acetylamino, wherein the substituents are identical or different;

$R^3$ denotes a hydrogen atom or an alkyl;

Y denotes an oxygen atom or —NR$^4$— wherein
$R^4$ denotes a hydrogen atom, a branched or unbranched alkyl with 1 to 6 carbon atoms or a phenylmethyl group;

m denotes the number 1 or 2 and

V denotes a hydrogen atom, fluorine, chlorine, bromine, iodine, cyano, alkyl, hydroxy, alkoxy, phenylalkoxy-, alkylcarbonyl, dialkylamino, hydroxymethyl, hydroxyethyl, hydroxypropyl, hydroxybutyl, trifluoromethyl, trifluoromethoxy, trifluoromethylthio or the group —(CH$_2$)$_o$—Y$^1$—W'Y$^2$, wherein o denotes the number 0, 1 or 2, W denotes the —SO$_2$— group or the group >C=X wherein
X denotes an oxygen atom or one of the divalent groups =N—CONH$_2$ or =N—CN, Y1 denotes a single bond, an oxygen atom or —NR$^5$— wherein
$R^5$ denotes a hydrogen atom or a straight-chained or branched alkyl with 1 to 6 carbon atoms or
$R^5$ together with the group Y$^2$, the enclosed nitrogen atom and the enclosed group >C=X forms a saturated heterocyclic ring with 5 to 7 ring members, Y$^2$ denotes a straight-chained or branched alkyl with 1 to 10 carbon atoms optionally substituted by a hydroxy, alkoxycarbonyl, aminocarbonyl, a cycloalkyl group with 4 to 10 carbon atoms, a straight-chained or branched alkoxy with 1 to 5 carbon atoms, an aminoalkyl, alkylaminoalkyl, dialkylaminoalkyl, phenylmethoxy, 2-phenylethoxy, phenyl or phenylalkyl with 1 to 3 carbon atoms in the alkyl moiety optionally mono-, di- or trisubstituted in the phenyl moiety by fluorine, chlorine, bromine, methyl, trifluoromethyl, cyano, amino, hydroxy, methoxy, acetyl, acetylamino, aminocarbonyl, methylaminocarbonyl or dimethylaminocarbonyl, wherein the substituents are identical or different; or Y2 is —NR$^6$R$^7$ wherein:
$R^6$ denotes a hydrogen atom, a straight-chained or branched alkyl with 1 to 6 carbon atoms optionally substituted by a hydroxy, carboxy, alkoxycarbonyl or dialkylamino with the proviso that the hydroxy is not bound in the 1-position of the alkyl, a cycloalkyl group with 4 to 8 carbon atoms, or $R^6$ is phenyl, phenylmethyl, 2-phenylethyl or 3-phenylpropyl optionally mono-, di- or trisubstituted in the phenyl moiety by fluorine, chlorine, bromine, methyl, trifluoromethyl, hydroxy, methoxy, amino, acetylamino, aminocarbonyl, methylaminocarbonyl, dimethylaminocarbonyl or cyano, wherein the substituents are identical or different, or $R^6$ is an alkanoyl, benzoyl, phenylalkanoyl, alkoxycarbonyl or aminocarbonyl; and $R^7$ has the meanings given for $R^6$ with the exception of a phenyl, alkanoyl, benzoyl, phenylalkanoyl, alkoxycarbonyl or aminocarbonyl or $R^6$ and $R^7$ together denote an n-alkylene group with 4 to 6 carbon atoms or $R^7$ together with the group $R^5$ of the group —NR$^5$— mentioned for Y$^1$ hereinbefore denotes an unbranched alkylene group or oxoalkylene group with 2 to 4 carbon atoms;

wherein all the abovementioned alkyl, cycloalkylalkyl, alkoxy, phenoxycarbonylalkyl, phenylalkoxy, phenylalkoxycarbonyl, phenylalkoxycarbonylalkyl, phenylalkanoyl, phenylalkyl, diphenylalkyl, naphthylalkyl, alkoxycarbonylalkyl, alkoxycarbonylmethoxy, carboxyalkyl, aminoalkyl, monoalkylamino, dialkylamino, alkylaminoalkyl, dialkylaminomethyl, dialkylaminoalkyl, alkylaminocarbonyl, dialkylaminocarbonyl, alkanoyl and alkoxycarbonyl, unless otherwise stated, each contain 1 to 5 carbon atoms in the alkyl and alkoxy moieties, or a tautomer, diastereomer, enantiomer or physiologically acceptable salt thereof.

2. A compound of the formula I according to claim 1, wherein

R, n, U, $R^1$, $R^2$, $R^3$ and m are defined as in claim 1,

Y denotes an oxygen atom or $-NR^4$ wherein
$R^4$ denotes a hydrogen atom, methyl or ethyl, and V is bound in the 3- or 4-position of the benzene ring and denotes a hydrogen, fluorine, chlorine, bromine, iodine, cyano, alkyl, hydroxy, alkoxy, phenylalkoxy, alkylcarbonyl, dialkylamino, hydroxymethyl, hydroxyethyl, hydroxypropyl, hydroxybutyl, trifluoromethyl, trifluoromethoxy, trifluoromethylthio or the group $-(CH_2)_o-Y^1-W-Y^2$ wherein
o, $Y^1$ and $Y^2$ are as hereinbefore defined and
W denotes carbonyl, or a tautomer, diastereomer, enantiomer or physiologically acceptable salt thereof.

3. A compound of the formula I according to claim 1 wherein

R denotes a phenyl, 1-naphthyl or 2-naphthyl group, a 5-membered heteroaromatic ring linked via a carbon atom, which contains a nitrogen, oxygen or sulphur atom or two nitrogen atoms, wherein a nitrogen atom of an imino group of said 5-membered heteroaromatic ring is optionally substituted by alkyl, or a 6-membered heteroaromatic ring linked via a carbon atom, which contains 1, 2 or 3 nitrogen atoms, Wherein a 1,4-butadienylene group is optionally attached both to the 5-membered or to the 6-membered heteroaromatic rings via two adjacent carbon atoms to form a bicyclic heteroaromatic rings which are optionally bound via a carbon atom of the 1,4-butadienylene group and the groups mentioned for P hereinbefore, including the mono- and bicyclic heteroaromatic rings in their carbon skeleton, are optionally substituted by a fluorine, chlorine, bromine, aikyl, a cycloalkyl group with 4 to 7 carbon atoms, an alkoxy, phenyl or trifluoromethyl, or R is a diphenylmethyl group wherein the phenyl groups are optionally mono- or disubstituted independently of one another by fluorine, chlorine, bromine, methyl, methoxy, hydroxycarbonylmethoxy, alkoxycarbonylmethoxy, hydroxy or trifluoromethyl, wherein the substituents in each case are identical or different;

n denotes the numbers 0, 1 or 2,

U denotes a single bond, $R^1$ denotes a branched or unbranched aliphatic alkylcarbonyl containing 2 to 5 carbon atoms optionally substituted in the alkyl moiety by alkoxycarbonyl, phenylalkoxycarbonyl, phenyl, benzoyl or pyridinylcarbonyl, wherein the phenyl and pyridinyl moieties in the abovementioned groups are optionally substituted by a fluorine, chlorine, bromine, alkyl, a cycloalkyl group with 4 to 7 carbon atoms, alkoxy or trifluoromethyl, the aminocarbonyi group in this subparagraph, is optionally mono- or disubstituted at the nitrogen atom by alkyl, phenylalkyl, (1-naphthyl)alkyl, (2-naphthyl)alkyl, alkoxycarbonylalkyl, carboxyalkyl, ω,ω-diphenylalkyl, phenyl, cycloalkyl or cycloalkylalkyl groups each with 3 to 8 carbon atoms in the ring, wherein the substituents are identical or different and the phenyl groups in the abovementioned groups are optionally substituted by a fluorine, chlorine, bromine, methyl, methoxy, hydroxy or trifluoromethyl;

or $R^1$ is an alkoxycarbonyl or phenylalkoxycarbonyl optionally substituted in the phenyl moiety by a fluorine, chlorine, bromine, methyl, methoxy, hydroxy or trifluoromethyl;

or $R^1$ is phenyl or a five-membered heteroaromatic ring bound via a carbon atom which contains a nitrogen, oxygen or sulphur atom or a nitrogen atom and an oxygen, sulphur or further nitrogen atom, wherein a nitrogen atom of an imino group of said 5-membered heteroaromatic ring is optionally substituted by an alkyl, or a 6-membered heteroaromatic ring linked via a carbon atom, which contains 1, 2 or 3 nitrogen atoms, wherein the phenyl group and the 5- and 6-membered heteroaromatic rings in their carbon skeleton are optionally substituted by a fluorine, chlorine, bromine, alkyl, by a cycloalkyl group with 3 to 6 carbon atoms, phenylalkyl, alkoxy, trifluoromethyl, hydroxy or amino;

or, if $R^2$ denotes a hydrogen atom, $R^1$ is optionally methyl;

$R^2$ denotes a hydrogen atom, an alkyl or phenylalkyl the phenyl group of which is optionally substituted by a fluorine, chlorine, bromine, alkyl, trifluoromethyl, amino or acetylamino;

$R^3$ denotes a hydrogen atom or methyl;

Y denotes $-NR^4-$ wherein
$R^4$ denotes a hydrogen atom, methyl or ethyl;

m denotes the numbers 1 or 2 and

V, which is bound in the 4 position of the benzene ring, denotes a hydrogen atom, fluorine, chlorine, bromine, cyano, alkyl, hydroxy, alkoxy, phenylalkoxy, hydroxymethyl, hydroxyethyl, trifluoromethyl or the group $-(CH_2)_o-Y^1-W-Y^2$ wherein
o denotes the numbers 0, 1 or 2,
W denotes carbonyl,
Y1 denotes a single bond, an oxygen atom or the group $-NR^5$, wherein
$R^5$ denotes a hydrogen atom or a straight-chained or branched alkyl with 1 to 4 carbon atoms or
$Y^2$ denotes a straight-chained or branched alkyl with 1 to 5 carbon atoms optionally substituted by a hydroxy, alkoxycarbonyl, aminocarbonyl, alkoxy with 1 to 3 carbon atoms, aminoalkyl, alkylaminoalkyl, dialkylaminoalkyl, phenyl or phenylalkyl group with 1 to 3 carbon atoms in the alkyl moiety optionally substituted in the phenyl moiety by a fluorine, chlorine, bromine, methyl, trifluoromethyl, cyano, amino, hydroxy or methoxy or $Y^2$ is $-NR^6R^7$ wherein
$R^6$ denotes a hydrogen atom, a straight-chained or branched alkyl with 1 to 6 carbon atoms, a cycloalkyl group with 4 to 6 carbon atoms or a phenyl group optionally substituted by a fluorine, chlorine, bromine, methyl, trifluoromethyl, hydroxy or methoxy, and
$R^7$ has the meanings given for $R^6$ with the exception of a phenyl group;

wherein all the abovementioned alkyl, alkoxy, phenylalkoxy, alkoxycarbonylalkyl, carboxyalkyl, dialkylaminoalkyl, alkylaminocarbonyl, dialkylaminocarbonyl, alkanoyl and alkoxycarbonyl groups, unless otherwise stated, contain 1 to 5 carbon atoms in the alkyl and alkoxy moieties;

or a tautomer, diastereomer, enantiomer or physiologically acceptable salt thereof.

4. A compound of the formula I according to claim 1 wherein

R denotes a 1-naphthyl, 2-naphthyl, 1H-pyrrol-2-yl, 1H-pyrrol-3-yl, 1H-indol-2-yl or 1H-indol-3-yl group optionally substituted in the carbon skeleton by an alkyl or an alkoxy with 1 to 3 carbon atoms or a diphenylmethyl group wherein the phenyl groups independently of one another are optionally substituted by a fluorine, chlorine, bromine, hydroxy, methoxy or methyl;

n denotes the numbers 0 or 1,

U denotes a single bond, $R^1$ denotes a branched or unbranched aliphatic alkylcarbonyl containing 2 to 5 carbon atoms, optionally substituted by alkoxycarbonyl with 1 to 4 carbon atoms in the alkoxy moiety, an aminocarbonyl group optionally substituted at the nitrogen atom by one or two alkyl groups each with 1 to 5 carbon atoms, phenylalkyl group with 1 to 5 carbon atoms in the alkyl moiety, alkoxyphenylalkyl with 1 to 3 carbon atoms in the alkoxy and 1 to 5 car-bon atoms in the alkyl moiety, (1-naphthyl)alkyl or (2-naphthyl)alkyl group with 1 to 3 carbon atoms in the alkyl moiety, alkoxycarbonylalkyl with 1 to 3 carbon atoms in the alkoxy and alkyl moieties, carboxyalkyl with 1 to 3 carbon atoms in the alkyl moiety, ω,ω-diphenylalkyl group with 1 to 5 carbon atoms in the alkyl moiety, a phenyl, cycloalkyl group with 4 to 7 carbon atoms in the ring, alkoxycarbonyl with 1 to 5 carbon atoms in the alkoxy moiety or a phenylalkoxycarbonyl with 1 to 3 carbon atoms in the alkoxy moiety, or $R^1$ is phenyl, pyridinyl or thiazolyl, each optionally substituted by alkyl with 1 to 3 carbon atoms or a phenylalkyl with 1 to 5 carbon atoms in the alkyl moiety;

or, if $R^2$ denotes a hydrogen atom, $R^1$ is optionally methyl;

$R^2$ denotes a hydrogen atom or alkyl with 1 to 3 carbon atoms optionally terminally substituted by phenyl;

$R^3$ denotes a hydrogen atom or methyl;

Y denotes an oxygen atom or —$NR^4$ wherein
$R^4$ denotes a hydrogen atom, methyl or ethyl, m denotes the number 1 and V is bound in the 4 position of the benzene ring and denotes a hydrogen atom, alkyl with 1 to 3 carbon atoms, hydroxy, alkoxy with 1 to 3 carbon atoms or the group —$(CH_2)_o$—$Y^1$—W—$Y^2$ wherein
o denotes the numbers C or 1,
W denotes a carbonyl;
Y1 denotes a single bond, an oxygen atom or —$NR^5$, wherein
$R^5$ denotes a hydrogen atom or methyl,
$Y^2$ denotes —$NR^6R^7$ wherein
$R^6$ denotes a hydrogen atom or alkyl with 1 to 3 carbon atoms and
$R^7$ denotes a hydrogen atom;

or a tautomer, diastereomer, enantiomer or physiologically acceptable salt thereof.

5. A compound selected from the group consisting of:
(R)-$N^2$-(diphenylacetyl)-$N^7$-(methylaminocarbonyl)-N-[[4-(methylaminocarbonyloxy)phenyl]methyl]-argininamide

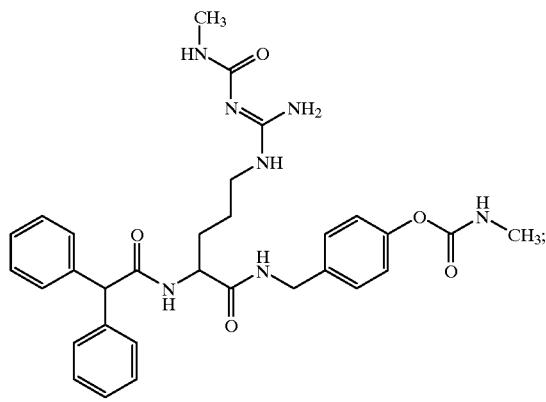

(R)-$N^2$-(diphenylacetyl)-N-[(4-hydroxyphenyl)methyl]-$N^7$-(methylaminocarbonyl)-argininamide

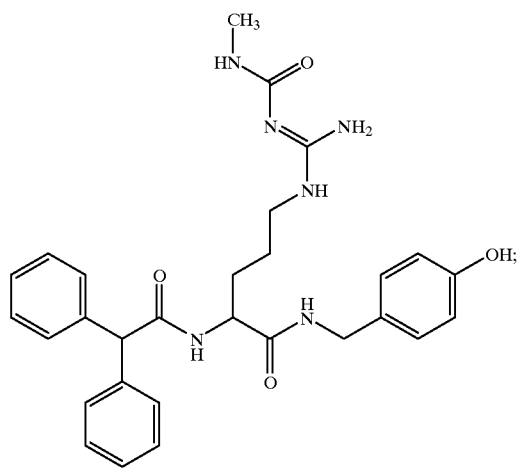

(R)-$N^7$-(butylaminocarbonyl)-$N^2$-(diphenylacetyl)-N-[(4-hydroxyphenyl)methyl]-argininamide;

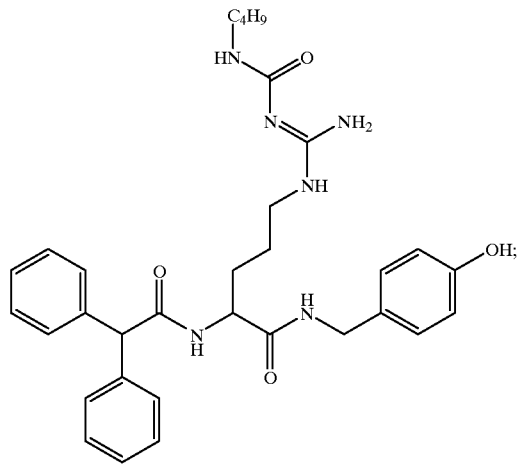

67

(R)-N-[[4-(aminocarbonylaminomethyl)phenyl]methyl]-N²-(diphenylacetyl)-N⁷-(methylaminocarbonyl)-argininamide

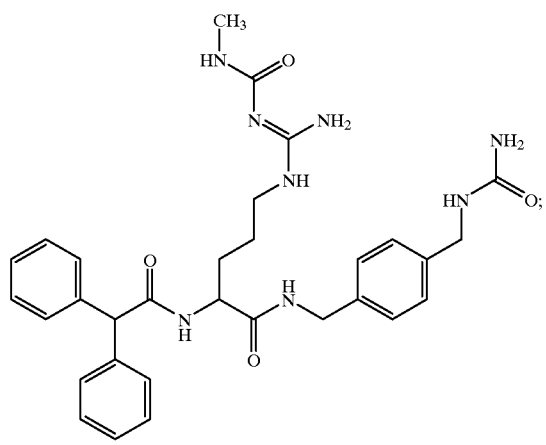

(R)-N-[[4-(aminocarbonylaminomethyl)phenyl]methyl]-N²-(diphenylacetyl)-N⁷-(ethylaminocarbonyl)-argininamide

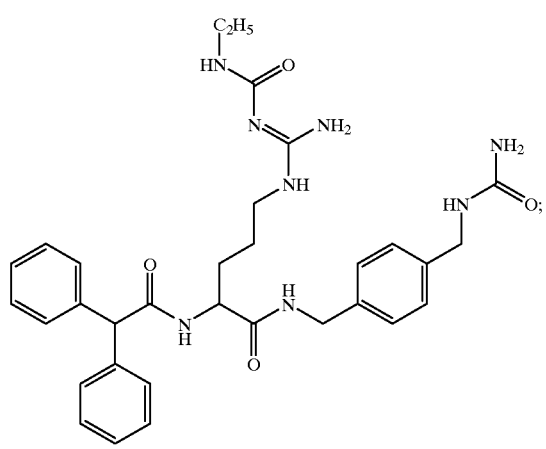

68

(R)-N²-(diphenylacetyl)-N⁷-(ethylaminocarbonyl)-N-[(4-hydroxyphenyl)methyl]-argininamide

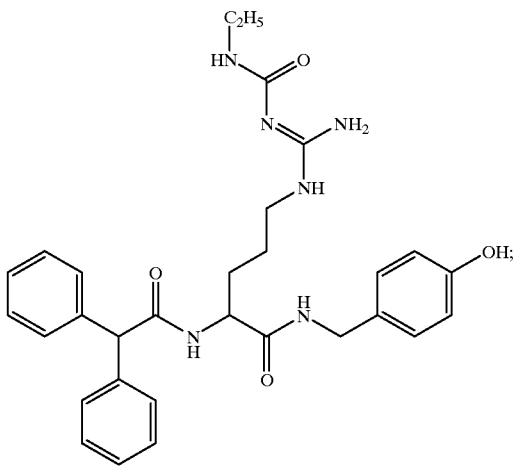

(R)-N²-(diphenylacetyl)-N-[(4-hydroxyphenyl)methyl]-N⁷-[(phenylmethyl)aminocarbonyl]-argininamide

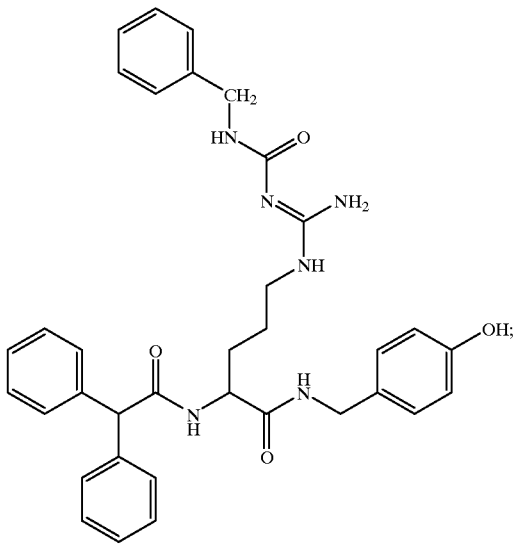

69

(R)-N²-(diphenylacetyl)-N-[(4-hydroxyphenyl)methyl]-N⁷-(methoxycarbonyl)-argininamide

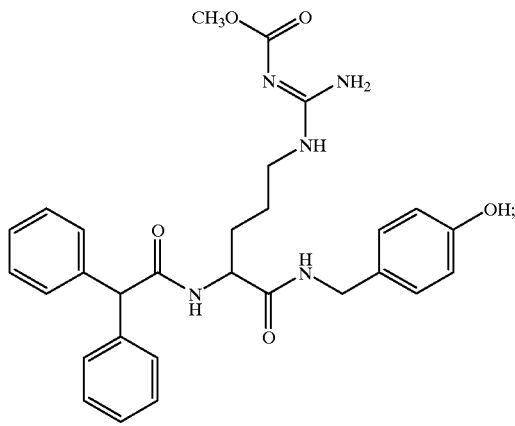

(R)-N⁷-(aminocarbonyl)-N²-(diphenylacetyl)-N-[(4-hydroxyphenyl)methyl]-argininamide

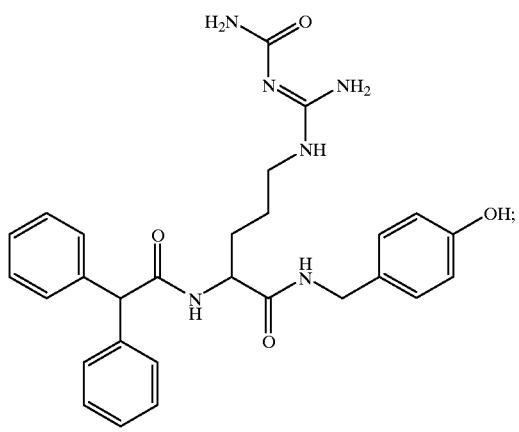

(R)-N-[[4-(aminocarbonylaminomethyl)phenyl]methyl]-N²-(diphenylacetyl)-N⁷-[[2-(ethoxycarbonyl)ethyl]aminocarbonyl]-argininamide

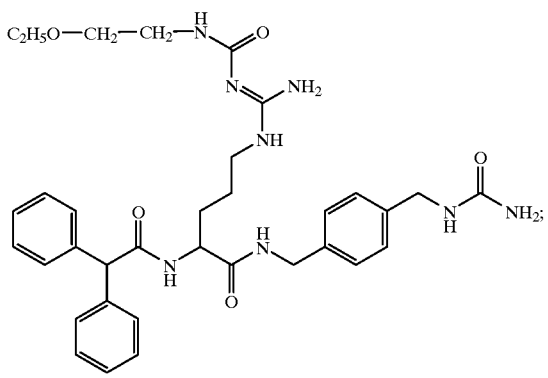

70

(R)-N²-(diphenylacetyl)-N-[(4-hydroxyphenyl)methyl]-N-methyl-N⁷-(methylaminocarbonyl)-argininamide

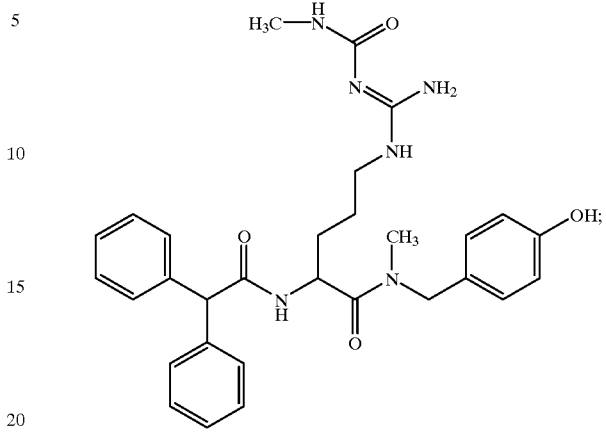

(R,S)-N²-(diphenylacetyl)-N-[(4-hydroxyphenyl)methyl]-N⁷[3-(methoxycarbonyl)-1-oxopropyl]-argininamide

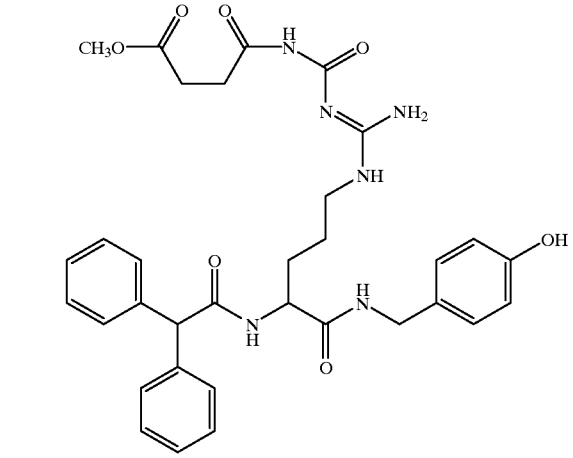

and a physiologically acceptable salt thereof.

6. A method of treating obesity said method comprises administering a therapeutically amount of a compound according to claim 1,2,3,4 or 5.

7. A pharmaceutical composition comprising as an active substance a compound according to claims 1,2,3,4,5,6 together with one or more inert carriers and/or diluents.

* * * * *